US012734232B2

(12) United States Patent
Yamasaki et al.

(10) Patent No.: US 12,734,232 B2
(45) Date of Patent: Sep. 15, 2026

(54) FOLLICULAR HELPER T (TFH) CELLS SPECIFIC TO SARS-COV-2 VIRUS

(71) Applicant: The University of Osaka, Osaka (JP)

(72) Inventors: Sho Yamasaki, Osaka (JP); Xiuyuan Lu, Osaka (JP); Yuki Hosono, Osaka (JP); Shigenari Ishizuka, Osaka (JP); Kazuo Yamashita, Osaka (JP); Nicolas Claude Paul Sax, Osaka (JP)

(73) Assignee: THE UNIVERSITY OF OSAKA, Osaka (JP)

( * ) Notice: Subject to any disclaimer, the term of this patent is extended or adjusted under 35 U.S.C. 154(b) by 351 days.

(21) Appl. No.: 18/282,385

(22) PCT Filed: Mar. 15, 2022

(86) PCT No.: PCT/JP2022/011707

§ 371 (c)(1),
(2) Date: Sep. 15, 2023

(87) PCT Pub. No.: WO2022/196699

PCT Pub. Date: Sep. 22, 2022

(65) Prior Publication Data

US 2024/0309051 A1 Sep. 19, 2024

(30) Foreign Application Priority Data

Mar. 16, 2021 (JP) ................................ 2021-042666

(51) Int. Cl.

| | |
|---|---|
| ***A61K 38/00*** | (2006.01) |
| ***A61K 35/26*** | (2015.01) |
| ***A61K 39/00*** | (2006.01) |
| ***A61K 39/12*** | (2006.01) |
| ***A61K 39/215*** | (2006.01) |
| ***C07K 14/005*** | (2006.01) |
| ***C07K 14/165*** | (2006.01) |
| ***C07K 16/104*** | (2026.01) |
| ***C07K 16/28*** | (2006.01) |

(52) U.S. Cl.

CPC ............ *A61K 39/12* (2013.01); *C07K 14/005* (2013.01); *C07K 16/104* (2026.01); *C07K 16/2809* (2013.01); *A61K 38/00* (2013.01); *A61K 2039/572* (2013.01); *C12N 2770/20022* (2013.01); *C12N 2770/20034* (2013.01)

(58) Field of Classification Search

CPC ...... A61K 39/12; A61K 39/215; A61K 38/00; A61K 2039/57; A61K 2039/572

See application file for complete search history.

(56) References Cited

FOREIGN PATENT DOCUMENTS

| | | | |
|---|---|---|---|
| JP | 2018-538280 | A | 12/2018 |
| JP | 2021-501167 | A | 1/2021 |
| WO | 2017/091729 | A1 | 6/2017 |
| WO | 2019/086540 | A1 | 5/2019 |
| WO | 2019/162043 | A1 | 8/2019 |
| WO | WO-2022/023727 | A1 | 2/2022 |
| WO | WO-2022/120216 | A1 | 6/2022 |

OTHER PUBLICATIONS

Sahin et al., "COVID-19 vaccine BNT162b1 elicits human antibody and Th1 T cell responses", Nature, Sep. 30, 2020, 586: pp. 594-599 (Supp. pp. 1-13).*

Bettini, SARS-CoV-2 mRNA Vaccines: Immunological Mechanism and Beyond, Vaccines, 9, 147:1-18 (2021).

Chour et al., Shared Antigen-specific CD8+ T Cell Responses Against the SARS-COV-2 Spike Protein in HLA A*02:01 COVID-19 Participants, medRxiv., doi: https://doi.org/ 10.1101/2020.05 .04.20085779 (2020).

Holenya et al., Peptide microarray-based analysis of antibody responses to SARS-COV-2 identifies unique epitopes with potential for diagnostic test development, medRxiv., doi: https://doi.org/10.I 101/2020.11.24.20216663 (2020).

Karimai et al., Analysis of Th1 response using KN7, an anti-idiotype antibody that recognizes the TCR of Peptide-25-specific T cell clones derived from *Mycobacterium tuberculosis* protein Ag85B, Proceed. J. Societ. Immun., 34:3-F-W41-27-P (2004).

Lu et al., Identification of conserved SARS-COV-2 spike epitopes that expand public cTfh clonotypes in mild COVID-19 patients, J. Exp. Med., 218(12):e20211327:1-13 (2021).

Peng et al., Broad and strong memory CD4+ and CD8+ T cells induced by SARS-CoV-2 in UK convalescent individuals following COVID-19, Nat. Immunol., 21(11):1336-1345 (2020).

Stamatakis et al., Generation of SARS-CoV-2 S1 Spike Glycoprotein Putative Antigenic Epitopes in Vitro by Intracellular Aminopeptidases, J. Proteome. Res., 19(11):4398-4406 (2020).

Zhang et al., Mapping the Immunodominance Landscape of SARS-CoV-2 Spike Protein for the Design of Vaccines against COVID-19, bioRxiv., pp. 1-23, doi: https://doi.org/10.1101/2020.04.23.056853 (2020).

Mateus et al., Selective and cross-reactive SARS-CoV-2 T cell epitopes in unexposed humans, Science, 370(6512): 89-94 (Oct. 2020).

Nelde et al., SARS-CoV-2-derived peptides define heterologous and COVID-19-induced T cell recognition, Nat. Immunol., 22(1): 74-85 (Jan. 2021).

(Continued)

*Primary Examiner* — Barry A Chestnut

(74) *Attorney, Agent, or Firm* — MARSHALL, GERSTEIN & BORUN LLP

(57) ABSTRACT

Follicular helper T cells specific to SARS-CoV-2 virus are provided. The present disclosure is based on the finding of public TfhTCR specific to spike (S) protein common to various patients, and has identified for the first time a public TCR specific to the SARS-CoV-2 virus and its MHC and antigenic epitopes to promote efficient immune responses, particularly those of B cells that produce neutralizing antibodies. For example, the present disclosure provides a composition containing an epitope specific to SARS-CoV-2 virus for inducing a follicular T cell.

19 Claims, 15 Drawing Sheets

Specification includes a Sequence Listing.

(56) References Cited

OTHER PUBLICATIONS

Braun et al., SARS-CoV-2-reactive T cells in healthy donors and patients with COVID-19, Nature, 587(7833): 270-274 (Nov. 2020).
Tarke et al., Comprehensive analysis of T cell immunodominance and immunoprevalence of SARS-CoV-2 epitopes in COVID-19 cases, Cell Rep. Med., 2(2): 100204 (Feb. 2021).
Worzner et al., Adjuvanted SARS-CoV-2 spike protein elicits neutralizing antibodies and CD4 T cell responses after a single immunization in mice, eBiomed., 63: 103197 (Jan. 2021).
Cooper et al., Rapid GMP-compliant expansion of SARS-CoV-2-specific T cells from convalescent donors for use as an allogenic cell therapy for COVID-19, Front. Immunol., 11: 598402 (Jan. 2021).

* cited by examiner

A
Clone 1
Clone 2
Counts
Inactivated virus
Recombinant S protein
S peptide pool
M+N peptide pool
CD69
Unstimulated
Stimulated
B
Clone 1
Clone 2
Counts
Inactivated virus
Recombinant S protein
S peptide pool
M+N peptide pool
CD69
Unstimulated
Stimulated C
Clone 1
Clone 2
Counts
CD69
S peptide pool #1
S peptide pool #2
9.69
69.4
9.66
40.8
D
Clone 1
Clone 2
S peptide pool #2
S peptide pool PepTivator®
73.2
12.6
24.2
5.73
E
Clone 1 P#4 APC
Clone 2 P#3 APC
S peptide pool #2
57.3
54.1

C

| Position | Peptides | DRB1*15:01 |
|---|---|---|
| 698 | SLGAENSVAYSNNSI | |
| 699 | LGAENSVAYSNNSIA | LGAENSVAYSNNSIA |
| 700 | GAENSVAYSNNSIAI | GAENSVAYSNNSIAI |
| 701 | AENSVAYSNNSIAIP | AENSVAYSNNSIAIP |
| 702 | ENSVAYSNNSIAIPT | ENSVAYSNNSIAIPT |
| 703 | NSVAYSNNSIAIPTN | |
| 707 | YSNNSIAIPTNFTIS | |
| 708 | SNNSIAIPTNFTISV | SNNSIAIPTNFTISV |
| 709 | NNSIAIPTNFTISVT | NNSIAIPTNFTISVT |
| 710 | NSIAIPTNFTISVTI | |
| 766 | ALTGIAVEQDKNTQE | |
| 767 | LTGIAVEQDKNTQEV | LTGIAVEQDKNTQEV |
| 768 | TGIAVEQDKNTQEVF | |
| 780 | EVFAQVKQIYKTPPI | |
| 781 | VFAQVKQIYKTPPIK | VFAQVKQIYKTPPIK |
| 782 | FAQVKQIYKTPPIKD | FAQVKQIYKTPPIKD |
| 783 | AQVKQIYKTPPIKDF | AQVKQIYKTPPIKDF |
| 784 | QVKQIYKTPPIKDFG | QVKQIYKTPPIKDFG |
| 785 | VKQIYKTPPIKDFGG | |
| 800 | FNFSQILPDPSKPSK | |
| 801 | NFSQILPDPSKPSKR | NFSQILPDPSKPSKR |
| 802 | FSQILPDPSKPSKRS | FSQILPDPSKPSKRS |
| 803 | SQILPDPSKPSKRSF | SQILPDPSKPSKRSF |
| 804 | QILPDPSKPSKRSFI | |
| 828 | LADAGFIKQYGDCLG | |
| 829 | ADAGFIKQYGDCLGD | ADAGFIKQYGDCLGD |
| 830 | DAGFIKQYGDCLGDI | DAGFIKQYGDCLGDI |
| 831 | AGFIKQYGDCLGDIA | AGFIKQYGDCLGDIA |
| 832 | GFIKQYGDCLGDIAA | GFIKQYGDCLGDIAA |
| 833 | FIKQYGDCLGDIAAR | |
| 863 | PLLTDEMIAQYTSAL | |
| 864 | LLTDEMIAQYTSALL | LLTDEMIAQYTSALL |
| 865 | LTDEMIAQYTSALLA | LTDEMIAQYTSALLA |
| 866 | TDEMIAQYTSALLAG | TDEMIAQYTSALLAG |
| 867 | DEMIAQYTSALLAGT | DEMIAQYTSALLAGT |
| 868 | EMIAQYTSALLAGTI | EMIAQYTSALLAGTI |
| 869 | MIAQYTSALLAGTIT | MIAQYTSALLAGTIT |
| 870 | IAQYTSALLAGTITS | |

D

| Peptide | Sequence |
|---|---|
| $S_{828-846}$ | LADAGFIKQYGDCLGDIAA |
| $S_{864-882}$ | LLTDEMIAQYTSALLAGTI |

E

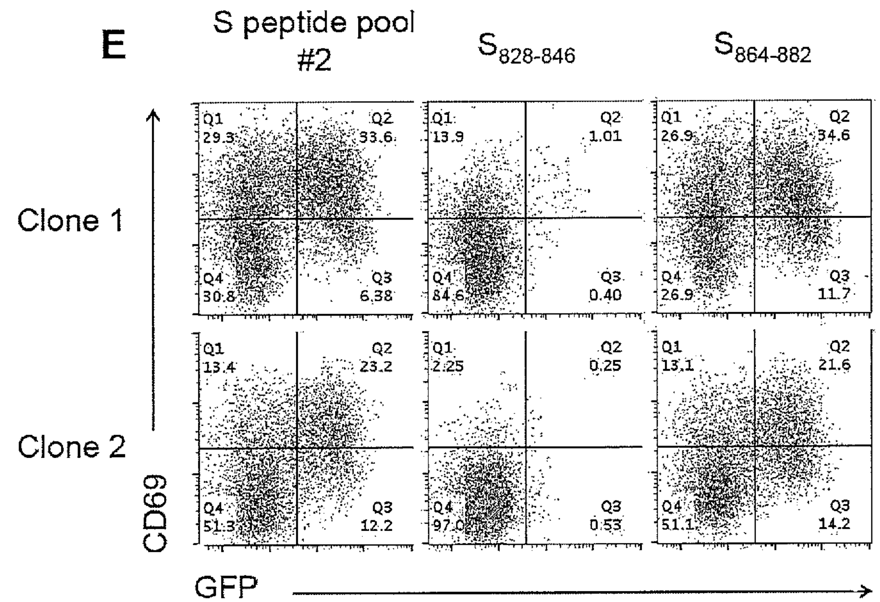

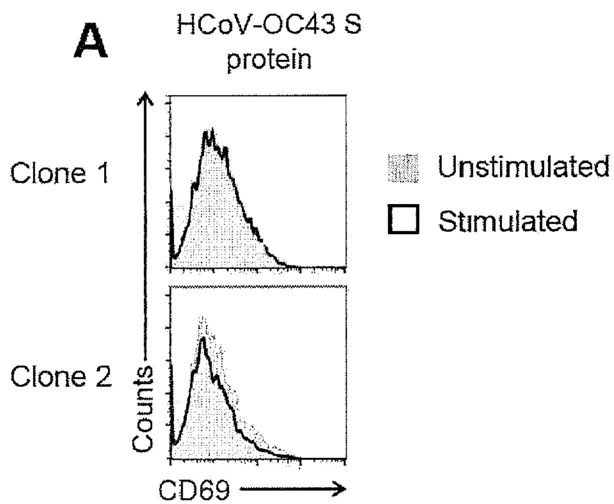

B

```
SARS-CoV2    LLTDEMIAQYTSALLAGTI
SARS-CoV     LLTDDMIAAYTAALVSGTA
MERS-CoV     LMDVNMEAAYTSSLLGSIA
HCoV-NL63    VADAERMAMYTGSLIGGMV
HCoV-OC43    LLSENQISGYTLAATSASL
HCoV-HKU1    ILSESQISGYTTAATVAAM
HCoV-229E    VADAERMAMYTGSLIGGIA
             :    .  : ** :    .
```

C

| Position | Peptide | DRB1*15:01 | DRB1*15:02 |
|---|---|---|---|
| 863 | PLLTDEMIAQYTSAL | | |
| 864 | LLTDEMIAQYTSALL | LLTDEMIAQYTSALL | LLTDEMIAQYTSALL |
| 865 | LTDEMIAQYTSALLA | LTDEMIAQYTSALLA | LTDEMIAQYTSALLA |
| 866 | TDEMIAQYTSALLAG | TDEMIAQYTSALLAG | TDEMIAQYTSALLAG |
| 867 | DEMIAQYTSALLAGT | DEMIAQYTSALLAGT | DEMIAQYTSALLAGT |
| 868 | EMIAQYTSALLAGTI | EMIAQYTSALLAGTI | EMIAQYTSALLAGTI |
| 869 | MIAQYTSALLAGTIT | MIAQYTSALLAGTIT | MIAQYTSALLAGTIT |
| 870 | IAQYTSALLAGTITS | | |

D
Clone 1
Clone 2
$S_{828-846}$
$S_{864-882}$
Counts
CD69
Unstimulated
Stimulated
E
Healthy
convalescent COVID-19
17%
24%
p=0.0028
log10(FRACTION)
-3.5
-4.0
-4.5
-5.0
-5.5
-6.0
Healthy
convalescent COVID-19

| A | B | C | D | E | F | G | H | I | | J | | K | |
|---|---|---|---|---|---|---|---|---|---|---|---|---|---|
| Clonotype | Donor | TRBV | CDR3β | TRBJ | TRAV | CDR3α | TRAJ | β occurrence (%) | | β expansion | | αβ occurrence (%) Healthy (pre-pandemic) | |
| | | | | | | | | Healthy | COVID | C/H | p-value | α | β |
| 1 # | Ts-018 | 7-3 | CASSLAGGSTDTQYF | 2-3 | 8-2 | CVVSRTGGGNKLTF | 10 | 14.5 | 21.9 | 2.3 | 2.4e-8* | 14.8 | 25.9 |
| | Ts-009 | 7-3 | CASSQAGGSTDTQYF | 2-3 | 2 | CAALNAGNMLTF | 39 | | | | | | |
| 2 | Ts-009 | 6-1 | CASSEGASNQPQHF | 1-5 | 12-1 | CVVNKGSSASKIIF | 3 | 3.1 | 13.8 | 5.9 | 5.0e-7* | 11.1 | 3.7 |
| 3 # | Ts-018 | 20-1 | CSARAGVQETQYF | 2-5 | 12-3 | CAMTYSGGYQKVTF | 13 | 6.0 | 15.1 | 2.0 | 0.0001* | 22.2 | 18.5 |
| | Ts-025 | 20-1 | CSARAGVQETQYF | 2-5 | 12-3 | CAMTPSGGYQKVTF | 13 | | | | | | |
| 4 | Ts-025 | 20-1 | CSARDWREETQYF | 2-5 | 8-4 | CAVSDQGRDDKIIF | 30 | 2.0 | 16.6 | 3.0 | 0.0003* | 3.7 | 0.0 |
| 5 # | Ts-017 | 11-2 | CASSQTYEQYF | 2-7 | 12-1 | CVVNRGSSYKLIF | 12 | 17.1 | 24.1 | 1.4 | 0.003* | 14.8 | 33.3 |
| (TCR-017/018) | Ts-018 | 11-2 | CASSPTYEQYF | 2-7 | 12-1 | CVVNRGSSYKLIF | 12 | | | | | | |
| 6 | Ts-002 | 20-1 | CSAKTSGRGETQYF | 2-5 | 13-2 | CAENSGGSNYKLTF | 53 | 1.5 | 8.8 | 2.6 | 0.006* | 96.3 | 0.0 |
| 7 # | Ts-010 | 7-9 | CASSSREDTQYF | 2-3 | 23 | CAATLYSGAGSYQLTF | 28 | 1.7 | 3.1 | 3.1 | 0.01* | 7.4 | 3.7 |
| | Ts-013 | 7-9 | CASSSREDTQYF | 2-3 | 23 | CAATSYSGAGSYQLTF | 28 | | | | | | |
| 8 | Ts-013 | 29-1 | CSVYRGLDEKLFF | 1-4 | 23 | CAASPPSYGGSQGNLIF | 42 | 0.3 | 0.1 | 2.7 | 0.02* | 0.0 | 0.0 |
| 9 | Ts-025 | 20-1 | CSARDWRGETQYF | 2-5 | 9-2 | CALSGGNRDDKIIF | 30 | 1.9 | 10.3 | 1.9 | 0.02* | 7.4 | 3.7 |
| 10 # | Ts-013 | 11-2 | CASSHGTGGRYEQYF | 2-7 | 13-1 | CAAQYALNF | 41 | 1.5 | 2.6 | 2.0 | 0.03* | 0.0 | 3.7 |
| | Ts-025 | 11-2 | CASSLGTSGRYEQYF | 2-7 | 13-1 | CAAGYALNF | 41 | | | | | | |

FOLLICULAR HELPER T (TFH) CELLS SPECIFIC TO SARS-COV-2 VIRUS

CROSS REFERENCE TO RELATED APPLICATIONS

This application is a U.S. national stage of International Patent Application No. PCT/JP2022/011707, filed Mar. 15, 2022, which claims the benefit of Japanese Patent Application No. 2021-042666, filed Mar. 16, 2021, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "59560_Seqlisting.txt." The Sequence Listing was created on Sep. 14, 2023, and is 15,765 bytes in size. The subject matter of the Sequence Listing is incorporated by reference herein in its entirety.

TECHNICAL FIELD

The present disclosure relates to follicular helper T cells (Tfh) specific to SARS-CoV-2 virus.

BACKGROUND ART

There are many unidentified points about acquired immune responses to the SARS-CoV-2 virus that causes the COVID-19 pandemic. Therefore, understanding the acquired immune response to SARS-CoV-2 infection becomes a key to prediction of long-term immunity and provision of information to vaccine design.

SUMMARY OF INVENTION

Solution to Problem

The present inventors found, based on the spike (S) protein, an amino acid sequence common to various patients, and found that this is related to specific public TfhTCR. By reconstituting the TCR α and β chains, the present inventors confirmed that the $S_{864-882}$ peptide presented by the frequent alleles DRB1*15:01/15:02 are T cell epitopes. The present inventors found that this TCR clonotype is widely detected among people worldwide, and the frequency of detection in each individual increases significantly upon SARS-CoV-2 infection.

Therefore, the present disclosure provides the following.

(Item 1)

A composition comprising a SARS-CoV-2 protein or a part thereof, or a functional equivalent thereof, for inducing a follicular T cell reactive with SARS-CoV-2.

(Item 2)

The composition of any of the above-mentioned items, wherein the aforementioned follicular T cell is also reactive with a coronavirus other than SARS-CoV-2.

(Item 3)

The composition of any of the above-mentioned items, wherein the aforementioned follicular T cell is specific to SARS-CoV-2.

(Item 4)

A composition comprising a SARS-CoV-2 protein or a part thereof, or a functional equivalent thereof, for inducing a follicular T cell reactive with at least one coronavirus.

(Item 5)

The composition of any of the above-mentioned items, wherein the aforementioned composition preferentially induces a follicular T cell.

(Item 6)

The composition of any of the above-mentioned items, wherein the aforementioned composition induces a follicular T cell in an HLA type-specific manner.

(Item 7)

The composition of any of the above-mentioned items, wherein the aforementioned SARS-CoV-2 protein or a part thereof comprises a sequence of a spike protein expressed by SARS-CoV-2 or a part thereof.

(Item 8)

The composition of any of the above-mentioned items, wherein the aforementioned SARS-CoV-2 protein or a part thereof comprises SEQ ID NO: 5 wherein $X_1$ is I, V, A, L, P, W, F, M or G,
$X_2$ is A, V, I, L, P, W, F, M or G,
$X_3$ is Q,
$X_4$ is Y, G, S, T, N, Q, C or F,
$X_5$ is T,
$X_6$ is S, Y, G, N, Q, C, For T,
$X_7$ is A, L, I, V, P, W, F, M or G,
$X_8$ is L, A, I, V, P, W, F, M or G, and
$X_9$ is L, A, I, V, P, W, F, M or G.

(Item 9)

The composition of any of the above-mentioned items, wherein the aforementioned SARS-CoV-2 protein or a part thereof comprises SEQ ID NO: 5 wherein $X_1$ is I, V, A, L or G,
$X_2$ is A, V, I, L or G,
$X_3$ is Q,
$X_4$ is Y or F,
$X_5$ is T,
$X_6$ is S or T,
$X_7$ is A, L, I, V or G,
$X_9$ is L, A, I, V or G, and
$X_9$ is L, A, I, V or G.

(Item 10)

The composition of any of the above-mentioned items, wherein the aforementioned SARS-CoV-2 protein or a part thereof comprises SEQ ID NO: 6, SEQ ID NO: 7, SEQ ID NO: 8, SEQ ID NO: 9, SEQ ID NO: 10, SEQ ID NO: 11, or SEQ ID NO: 12.

(Item 11)

The composition of any of the above-mentioned items, wherein the aforementioned SARS-CoV-2 protein or a part thereof comprises the amino acid sequence shown in SEQ ID NO: 1.

(Item 12)

The composition of any of the above-mentioned items, wherein the aforementioned SARS-CoV-2 protein or a part thereof comprises up to 20 amino acids.

(Item 13)

The composition of any of the above-mentioned items, wherein the aforementioned SARS-CoV-2 protein or a part thereof consists of the amino acid sequence shown in SEQ ID NO:1.

(Item 14)

The composition of any of the above-mentioned items, wherein the aforementioned SARS-CoV-2 protein or a part thereof comprises the amino acid sequence shown in SEQ ID NO: 13, SEQ ID NO: 38, SEQ ID NO: 39, SEQ ID NO:

40, SEQ ID NO: 41, SEQ ID NO: 42, or SEQ ID NO: 43, and is at least 9 amino acids long.

(Item 15)

The composition of any of the above-mentioned items, wherein the aforementioned SARS-CoV-2 protein or a part thereof consists of the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43.

(Item 16)

The composition of any of the above-mentioned items, wherein the aforementioned follicular T cell is a public follicular T cell.

(Item 17)

The composition of any of the above-mentioned items, wherein the aforementioned follicular T cell has a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

(Item 18)

A polypeptide for presenting a SARS-CoV-2 protein or a part thereof to HLA.

(Item 19)

The polypeptide of any of the above-mentioned items, wherein the aforementioned SARS-CoV-2 protein or a part thereof comprises the sequence of the spike protein expressed by SARS-CoV-2 or a part thereof.

(Item 20)

The polypeptide of any of the above-mentioned items, wherein the aforementioned SARS-CoV-2 protein or a part thereof comprises SEQ ID NO: 5 wherein $X_1$ is I, V, A, L, P, W, F, M or G,
$X_2$ is A, V, I, L, P, W, F, M or G,
$X_3$ is Q,
$X_4$ is Y, G, S, T, N, Q, C or F,
$X_5$ is T,
$X_6$ is S, Y, G, N, Q, C, F or T,
$X_7$ is A, L, I, V, P, W, F, M or G,
$X_8$ is L, A, I, V, P, W, F, M or G, and
$X_9$ is L, A, I, V, P, W, F, M or G.

(Item 21)

The polypeptide of any of the above-mentioned items, wherein the aforementioned SARS-CoV-2 protein or a part thereof comprises SEQ ID NO: 5 wherein $X_1$ is I, V, A, L or G,
$X_2$ is A, V, I, L or G,
$X_3$ is Q,
$X_4$ is Y or F,
$X_5$ is T,
$X_6$ is S or T,
$X_7$ is A, L, I, V or G,
$X_8$ is L, A, I, V or G, and
$X_9$ is L, A, I, V or G.

(Item 22)

The polypeptide of any of the above-mentioned items, wherein the aforementioned SARS-CoV-2 protein or a part thereof comprises SEQ ID NO: 6, SEQ ID NO: 7, SEQ ID NO: 8, SEQ ID NO: 9, SEQ ID NO: 10, SEQ ID NO: 11, or SEQ ID NO: 12.

(Item 23)

The polypeptide of any of the above-mentioned items, wherein the aforementioned SARS-CoV-2 protein or a part thereof comprises the amino acid sequence shown in SEQ ID NO:1.

(Item 24)

The polypeptide of any of the above-mentioned items, wherein the aforementioned SARS-CoV-2 protein or a part thereof comprises up to 20 amino acids.

(Item 25)

The polypeptide of any of the items 18 to 24, wherein the aforementioned SARS-CoV-2 protein or a part thereof consists of the amino acid sequence shown in SEQ ID NO:1.

(Item 26)

The polypeptide of any of the above-mentioned items, wherein the aforementioned SARS-CoV-2 protein or a part thereof comprises the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43, and is at least 9 amino acids long.

(Item 27)

The polypeptide of any of the above-mentioned items, wherein the aforementioned SARS-CoV-2 protein or a part thereof consists of the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43.

(Item 28)

An antibody that specifically binds to a TCR that interacts with a SARS-CoV-2 protein or a part thereof.

(Item 29)

The antibody of any of the above-mentioned items, wherein the aforementioned SARS-CoV-2 protein or a part thereof comprises the sequence of the spike protein expressed by SARS-CoV-2 or a part thereof.

(Item 30)

The antibody of any of the above-mentioned items, wherein the aforementioned SARS-CoV-2 protein or a part thereof comprises SEQ ID NO: 5 wherein $X_1$ is I, V, A, L, P, W, F, M or G,
$X_2$ is A, V, I, L, P, W, F, M or G,
$X_3$ is Q,
$X_4$ is Y, G, S, T, N, Q, C or F,
$X_5$ is T,
$X_6$ is S, Y, G, N, Q, C, F or T,
$X_7$ is A, L, I, V, P, W, F, M or G,
$X_8$ is L, A, I, V, P, W, F, M or G, and
$X_9$ is L, A, I, V, P, W, F, M or G.

(Item 31)

The antibody of any of the above-mentioned items, wherein the aforementioned SARS-CoV-2 protein or a part thereof comprises SEQ ID NO: 5 wherein $X_1$ is I, V, A, L or G,
$X_2$ is A, V, I, L or G,
$X_3$ is Q,
$X_4$ is Y or F,
$X_5$ is T,
$X_6$ is S or T,
$X_7$ is A, L, I, V or G,
$X_8$ is L, A, I, V or G, and
$X_9$ is L, A, I, V or G.

(Item 32)

The antibody of any of the above-mentioned items, wherein the aforementioned SARS-CoV-2 protein or a part thereof comprises SEQ ID NO: 6, SEQ ID NO: 7, SEQ ID NO: 8, SEQ ID NO: 9, SEQ ID NO: 10, SEQ ID NO: 11, or SEQ ID NO: 12.

(Item 33)

The antibody of any of the above-mentioned items, wherein the aforementioned SARS-CoV-2 protein or a part thereof comprises the amino acid sequence shown in SEQ ID NO:1.

(Item 34)

The antibody of any of the above-mentioned items, wherein the aforementioned SARS-CoV-2 protein or a part thereof comprises up to 20 amino acids.

(Item 35)

The antibody of any of the above-mentioned items, wherein the aforementioned SARS-CoV-2 protein or a part thereof consists of the amino acid sequence shown in SEQ ID NO:1.

(Item 36)

The antibody of any of the above-mentioned items, wherein the aforementioned SARS-CoV-2 protein or a part thereof comprises the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43, and is at least 9 amino acids long.

(Item 37)

The antibody of any of the above-mentioned items, wherein the aforementioned SARS-CoV-2 protein or a part thereof consists of the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43.

(Item 38)

A composition for enhancing immunity acquisition against SARS-CoV-2, comprising a follicular T cell reactive with SARS-CoV-2.

(Item 39)

The composition of any of the above-mentioned items, wherein the aforementioned follicular T cell is also reactive with a coronavirus other than SARS-CoV-2.

(Item 40)

The composition of any of the above-mentioned items, wherein the aforementioned follicular T cell is specific to SARS-CoV-2.

(Item 41)

The composition of any of the above-mentioned items, wherein the aforementioned follicular T cell is a public follicular T cell.

(Item 42)

The composition of any of the above-mentioned items, wherein the aforementioned follicular T cell has a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

The present disclosure further provides the following items.

(Item A1)

A method for inducing a follicular T cell reactive with SARS-CoV-2, comprising a step of administering SARS-CoV-2 protein or a part thereof, or a functional equivalent thereof to a test subject.

(Item A2)

The method of any of the above-mentioned items, wherein the aforementioned follicular T cell is also reactive with a coronavirus other than SARS-CoV-2.

(Item A3)

The method of any of the above-mentioned items, wherein the aforementioned follicular T cell is specific to SARS-CoV-2.

(Item A4)

A method for inducing a follicular T cell reactive with at least one coronavirus, comprising a step of administering a SARS-CoV-2 protein or a part thereof, or a functional equivalent thereof to a test subject.

(Item A5)

The method of any of the above-mentioned items, wherein the aforementioned SARS-CoV-2 protein or a part thereof, or a functional equivalent thereof preferentially induces a follicular T cell.

(Item A6)

The method of any of the above-mentioned items, wherein the aforementioned SARS-CoV-2 protein or a part thereof, or a functional equivalent thereof induces a follicular T cell in an HLA type-specific manner.

(Item A7)

The method of any of the above-mentioned items, wherein the aforementioned SARS-CoV-2 protein or a part thereof comprises the sequence of the spike protein expressed by SARS-CoV-2 or a part thereof.

(Item A8)

The method of any of the above-mentioned items, wherein the aforementioned SARS-CoV-2 protein or a part thereof comprises SEQ ID NO: 5 wherein $X_1$ is I, V, A, L, P, W, F, M or G, $X_2$ is A, V, I, L, P, W, F, M or G, $X_3$ is Q, $X_4$ is Y, G, S, T, N, Q, C or F, $X_5$ is T, $X_6$ is S, Y, G, N, Q, C, F or T, $X_7$ is A, L, I, V, P, W, F, M or G, $X_8$ is L, A, I, V, P, W, F, M or G, and $X_9$ is L, A, I, V, P, W, F, M or G.

(Item A9)

The method of any of the above-mentioned items, wherein the aforementioned SARS-CoV-2 protein or a part thereof comprises SEQ ID NO: 5 wherein $X_1$ is I, V, A, L or G, $X_2$ is A, V, I, L or G, $X_3$ is Q, $X_4$ is Y or F, $X_5$ is T, $X_6$ is S or T, $X_7$ is A, L, I, V or G, $X_8$ is L, A, I, V or G, and $X_9$ is L, A, I, V or G.

(Item A10)

The method of any of the above-mentioned items, wherein the aforementioned SARS-CoV-2 protein or a part thereof comprises SEQ ID NO: 6, SEQ ID NO: 7, SEQ ID NO: 8, SEQ ID NO: 9, SEQ ID NO: 10, SEQ ID NO: 11, or SEQ ID NO: 12.

(Item A11)

The method of any of the above-mentioned items, wherein the aforementioned SARS-CoV-2 protein or a part thereof comprises the amino acid sequence shown in SEQ ID NO:1.

(Item A12)

The method of any of the above-mentioned items, wherein the aforementioned SARS-CoV-2 protein or a part thereof comprises up to 20 amino acids.

(Item A13)

The method of any of the above-mentioned items, wherein the aforementioned SARS-CoV-2 protein or a part thereof consists of the amino acid sequence shown in SEQ ID NO:1.

(Item A14)

The method of any of the above-mentioned items, wherein the aforementioned SARS-CoV-2 protein or a part thereof comprises the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43, and is at least 9 amino acids long.

(Item A15)

The method of any of the above-mentioned items, wherein the aforementioned SARS-CoV-2 protein or a part thereof consists of the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43.

(Item A16)

The method of any of the above-mentioned items, wherein the aforementioned follicular T cell is a public follicular T cell.

(Item A17)

The method of any of the above-mentioned items, wherein the aforementioned follicular T cell has a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

(Item A18)

Use of a SARS-CoV-2 protein or a part thereof, or a functional equivalent thereof in the production of a medicament for inducing a follicular T cell reactive with SARS-CoV-2.

(Item A19)

The use of any of the above-mentioned items, wherein the aforementioned follicular T cell is also reactive with a coronavirus other than SARS-CoV-2.

(Item A20)

The use of any of the above-mentioned items, wherein the aforementioned follicular T cell is specific to SARS-CoV-2.

(Item A21)

Use of a SARS-CoV-2 protein or a part thereof, or a functional equivalent thereof in the production of a medicament for inducing a follicular T cell reactive with at least one coronavirus.

(Item A22)

The use of any of the above-mentioned items, wherein the aforementioned SARS-CoV-2 protein or a part thereof, or a functional equivalent thereof preferentially induces a follicular T cell.

(Item A235)

The use of any of the above-mentioned items, wherein the aforementioned SARS-CoV-2 protein or a part thereof, or a functional equivalent thereof induces a follicular T cell in an HLA type-specific manner.

(Item A24)

The use of any of the above-mentioned items, wherein the aforementioned SARS-CoV-2 protein or a part thereof comprises the sequence of the spike protein expressed by SARS-CoV-2 or a part thereof.

(Item A25)

The use of any of the above-mentioned items, wherein the aforementioned SARS-CoV-2 protein or a part thereof comprises SEQ ID NO: 5 wherein $X_1$ is I, V, A, L, P, W, F, M or G,
$X_2$ is A, V, I, L, P, W, F, M or G,
$X_3$ is Q,
$X_4$ is Y, G, S, T, N, Q, C or F,
$X_5$ is T,
$X_6$ is S, Y, G, N, Q, C, F or T,
$X_7$ is A, L, I, V, P, W, F, M or G,
$X_8$ is L, A, I, V, P, W, F, M or G, and
$X_9$ is L, A, I, V, P, W, F, M or G.

(Item A26)

The use of any of the above-mentioned items, wherein the aforementioned SARS-CoV-2 protein or a part thereof comprises SEQ ID NO: 5 wherein $X_1$ is I, V, A, L or G,
$X_2$ is A, V, I, L or G,
$X_3$ is Q,
$X_4$ is Y or F,
$X_5$ is T,
$X_6$ is S or T,
$X_7$ is A, L, I, V or G,
$X_8$ is L, A, I, V or G, and
$X_9$ is L, A, I, V or G.

(Item A27)

The use of any of the above-mentioned items, wherein the aforementioned SARS-CoV-2 protein or a part thereof comprises SEQ ID NO: 6, SEQ ID NO: 7, SEQ ID NO: 8, SEQ ID NO: 9, SEQ ID NO: 10, SEQ ID NO: 11, or SEQ ID NO: 12.

(Item A28)

The use of any of the above-mentioned items, wherein the aforementioned SARS-CoV-2 protein or a part thereof comprises the amino acid sequence shown in SEQ ID NO:1.

(Item A29)

The use of any of the above-mentioned items, wherein the aforementioned SARS-CoV-2 protein or a part thereof comprises up to 20 amino acids.

(Item A30)

The use of any of the above-mentioned items, wherein the aforementioned SARS-CoV-2 protein or a part thereof consists of the amino acid sequence shown in SEQ ID NO: 1.

(Item A31)

The use of any of the above-mentioned items, wherein the aforementioned SARS-CoV-2 protein or a part thereof comprises the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43, and is at least 9 amino acids long.

(Item A32)

The use of any of the above-mentioned items, wherein the aforementioned SARS-CoV-2 protein or a part thereof consists of the amino acid sequence shown in SEQ ID NO: 13, SEQ ID NO: 38, SEQ ID NO: 39, SEQ ID NO: 40, SEQ ID NO: 41, SEQ ID NO: 42, or

SEQ ID NO: 43.

(Item A33)

The use of any of the above-mentioned items, wherein the aforementioned follicular T cell is a public follicular T cell.

(Item A34)

The use of any of the above-mentioned items, wherein the aforementioned follicular T cell has a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

(Item A35)

A SARS-CoV-2 protein or a part thereof, or a functional equivalent thereof, for inducing a follicular T cell reactive with SARS-CoV-2.

(Item A36)

The SARS-CoV-2 protein or a part thereof, or a functional equivalent thereof of any of the above-mentioned items, wherein the aforementioned follicular T cell is also reactive with a coronavirus other than SARS-CoV-2.

(Item A37)

The SARS-CoV-2 protein or a part thereof, or a functional equivalent thereof of any of the above-mentioned items, wherein the aforementioned follicular T cell is specific to SARS-CoV-2.

(Item A38)

A SARS-CoV-2 protein or a part thereof, or a functional equivalent thereof, for inducing a follicular T cell reactive with at least one coronavirus.

(Item A39)

The SARS-CoV-2 protein or a part thereof, or a functional equivalent thereof of any of the above-mentioned items, wherein the aforementioned SARS-CoV-2 protein or a part thereof, or a functional equivalent thereof preferentially induces a follicular T cell.

(Item A40)

The SARS-CoV-2 protein or a part thereof, or a functional equivalent thereof of any of the above-mentioned items, wherein the aforementioned SARS-CoV-2 protein or a part thereof, or a functional equivalent thereof induces a follicular T cell in an HLA type-specific manner.

(Item A41)

The SARS-CoV-2 protein or a part thereof, or a functional equivalent thereof of any of the above-mentioned items, wherein the aforementioned SARS-CoV-2 protein or a part thereof comprises the sequence of the spike protein expressed by SARS-CoV-2 or a part thereof.

(Item A42)

The SARS-CoV-2 protein or a part thereof, or a functional equivalent thereof of any of the above-mentioned items, wherein the aforementioned SARS-CoV-2 protein or a part thereof comprises SEQ ID NO: 5 wherein $X_1$ is I, V, A, L, P, W, F, M or G,
$X_2$ is A, V, I, L, P, W, F, M or G,
$X_3$ is Q,
$X_4$ is Y, G, S, T, N, Q, C or F,
$X_5$ is T,
$X_6$ is S, Y, G, N, Q, C, F or T,
$X_7$ is A, L, I, V, P, W, F, M or G,
$X_8$ is L, A, I, V, P, W, F, M or G, and
$X_9$ is L, A, I, V, P, W, F, M or G.

(Item A43)

The SARS-CoV-2 protein or a part thereof, or a functional equivalent thereof of any of the above-mentioned items, wherein the aforementioned SARS-CoV-2 protein or a part thereof comprises SEQ ID NO: 5 wherein $X_1$ is I, V, A, L or G,
$X_2$ is A, V, I, L or G,
$X_3$ is Q,
$X_4$ is Y or F,
$X_5$ is T,
$X_6$ is S or T,
$X_7$ is A, L, I, V or G,
$X_8$ is L, A, I, V or G, and
$X_9$ is L, A, I, V or G.

(Item A44)

The SARS-CoV-2 protein or a part thereof, or a functional equivalent thereof of any of the above-mentioned items, wherein the aforementioned SARS-CoV-2 protein or a part thereof comprises SEQ ID NO: 6, SEQ ID NO: 7, SEQ ID NO: 8, SEQ ID NO: 9, SEQ ID NO: 10, SEQ ID NO: 11, or SEQ ID NO: 12.

(Item A45)

The SARS-CoV-2 protein or a part thereof, or a functional equivalent thereof of any of the above-mentioned items, wherein the aforementioned SARS-CoV-2 protein or a part thereof comprises the amino acid sequence shown in SEQ ID NO: 1.

(Item A46)

The SARS-CoV-2 protein or a part thereof, or a functional equivalent thereof of any of the above-mentioned items, wherein the aforementioned SARS-CoV-2 protein or a part thereof comprises up to 20 amino acids.

(Item A47)

The SARS-CoV-2 protein or a part thereof, or a functional equivalent thereof of any of the above-mentioned items, wherein the aforementioned SARS-CoV-2 protein or a part thereof consists of the amino acid sequence shown in SEQ ID NO: 1.

(Item A48)

The SARS-CoV-2 protein or a part thereof, or a functional equivalent thereof of any of the above-mentioned items, wherein the aforementioned SARS-CoV-2 protein or a part thereof comprises the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43, and is at least 9 amino acids long.

(Item A49)

The SARS-CoV-2 protein or a part thereof, or a functional equivalent thereof of any of the above-mentioned items, wherein the aforementioned SARS-CoV-2 protein or a part thereof consists of the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43.

(Item A50)

The SARS-CoV-2 protein or a part thereof, or a functional equivalent thereof of any of the above-mentioned items, wherein the aforementioned follicular T cell is a public follicular T cell.

(Item A51)

The SARS-CoV-2 protein or a part thereof, or a functional equivalent thereof of any of the above-mentioned items, wherein the aforementioned follicular T cell has a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO:

30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

(Item A52)

A method for enhancing immunity acquisition against SARS-CoV-2, comprising a step of administering a follicular T cell reactive with SARS-CoV-2.

(Item A53)

The method of any of the above-mentioned items, wherein the aforementioned follicular T cell is also reactive with a coronavirus other than SARS-CoV-2.

(Item A54)

The method of any of the above-mentioned items, wherein the aforementioned follicular T cell is specific to SARS-CoV-2.

(Item A55)

The method of any of the above-mentioned items, wherein the aforementioned follicular T cell is a public follicular T cell.

(Item A56)

The method of any of the above-mentioned items, wherein the aforementioned follicular T cell has a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

(Item A57)

Use of a follicular T cell reactive with SARS-CoV-2, in the production of a medicament for enhancing immunity acquisition against SARS-CoV-2.

(Item A58)

The use of any of the above-mentioned items, wherein the aforementioned follicular T cell is also reactive with a coronavirus other than SARS-CoV-2.

(Item A59)

The use of any of the above-mentioned items, wherein the aforementioned follicular T cell is specific to SARS-CoV-2.

(Item A60)

The use of any of the above-mentioned items, wherein the aforementioned follicular T cell is a public follicular T cell.

(Item A61)

The use of any of the above-mentioned items, wherein the aforementioned follicular T cell has a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

(Item A62)

A follicular T cell reactive with SARS-CoV-2, for enhancing immunity acquisition against SARS-CoV-2.

(Item A63)

The follicular T cell of any of the above-mentioned items, which is also reactive with a coronavirus other than SARS-CoV-2.

(Item A64)

The follicular T cell of any of the above-mentioned items, which is specific to SARS-CoV-2.

(Item A65)

The follicular T cell of any of the above-mentioned items, which is a public follicular T cell.

(Item A66)

The follicular T cell of any of the above-mentioned items, which has a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

The present disclosure is intended so that one or more of the aforementioned features can be provided not only as the explicitly disclosed combinations, but also as other combinations. Additional embodiments and advantages of the present disclosure are recognized by those skilled in the art by reading and understanding the following detailed description, as needed.

Advantageous Effects of Invention

The present disclosure is based on the finding of public TfhTCR specific to spike (S) protein common to various patients, and provides a follicular helper T cell (Tfh) specific to a composition containing an epitope specific to SARS-CoV-2 virus for inducing a follicular T cell.

BRIEF DESCRIPTION OF DRAWINGS

FIG. 3 is a diagram showing that TCR cloned from Tfh cells of patients is reactive with peptides derived from the SARS-CoV-2 S protein. Clones 1 and 2 were stimulated with S peptide pools #1 and #2 (1 μg/ml per peptide) for 20 hr in the presence of APC of the same origin (FIG. 3C). Clones 1 and 2 were stimulated with S-peptide pool #2 and S-peptide pool PepTivator (registered trademark) (both 0.3 μg/ml per peptide) for 20 hr in the presence of APC of the same origin, and then stained for CD69 (FIG. 3D). Clones 1 and 2 were stimulated with S-peptide pool #2 (1 μg/ml per peptide) for 20 hr in the presence of APCs derived from different donors and then analyzed for CD69 expression (FIG. 3E).

[FIG. 5-2]

FIG. 5 is a diagram showing the identified HLA and S protein peptides recognized by S protein-responsive TCRs. Possible peptides (red: strong binding peptide, gray: weak binding peptide) presented by DRB1*15:01 to a part of S protein containing epitopes of clones 1 and 2 predicted by NetMHC (FIG. 5C). Sequences of two strong binding peptides synthesized (FIG. 5D). Clones 1 and 2 were left unstimulated (filled histograms) or stimulated with S peptide pool #2 (0.3 μg/ml/peptide) and a single peptide (1 μg/ml) (open histograms), each for 20 hr in the presence of APC of different origin, and then stained for CD69 (FIG. 5E).

[FIG. 6-1]

FIG. 6 shows that $S_{864-882}$ is a SARS-CoV-2-specific peptide that is widely recognized by healthy populations and convalescent COVID-19 patients. T-cell hybridomas expressing TCRs of clonotype 1/2 (clone 1 and clone 2, respectively) were co-cultured with peptide pools derived from APC and HCoV-OC43 S protein (0.3 μg/ml per peptide) (FIG. 6A). Sequence alignment of the corresponding region of $S_{864-882}$ human coronavirus to SARS-CoV-2 (FIG. 6B). Binding capacity of peptide $S_{864-882}$ to DRB1*15:01 and *15:02 predicted by NetMHC4.0 server (red: strong binding peptide, gray: weak binding peptide) (FIG. 6C).

[FIG. 6-2]

FIG. 6 shows that $S_{864-882}$ is a SARS-CoV-2-specific peptide that is widely recognized by healthy populations and convalescent COVID-19 patients. Clones 1 and 2 were stimulated with a single peptide in the presence of APC with DRB1*15:02 and analyzed for CD69 expression (FIG. 6D). Distribution of clonotype 1/2 in public databases of healthy donors and convalescent COVID-19 patients. Upper panel, percentage of individuals with clonotype 1/2 in both groups, lower panel, increase in clonotype 1/2 in each individual in both groups (FIG. 6E).

FIG. 7 shows that a mixture of CD4-positive cells and patient-derived B cells immortalized by EBV infection which is stimulated with SARS-CoV-2 $S_{864-882}$ peptide have higher IL-21 concentrations in the medium compared to unstimulated cells.

[FIG. 8-1]

FIG. 8 shows the results of stimulation of cells that underwent reconstitution of TCRαβ pairs, with a polypeptide consisting of an amino acid sequence obtained by replacing each amino acid in the amino acid sequence of SEQ ID NO: 13 with alanine.

[FIG. 8-2]

FIG. 8 shows the results of stimulation of cells that underwent reconstitution of TCRαβ pairs, with a polypeptide consisting of an amino acid sequence obtained by replacing each amino acid in the amino acid sequence of SEQ ID NO: 13 with alanine.

FIG. 9 shows the results of stimulation of cells that underwent reconstitution of TCRαβ pairs, with a polypeptide consisting of the amino acid sequences of SEQ ID NO: 44-56.

[FIG. 10-1]

FIG. 10 shows TCRα pairs of public Tfhs and epitopes they recognize. (A) Clonotypes detected in multiple donors of the sample pool are shown as column A. Clonotypic occurrence was calculated based on public databases including a dataset (columns K and I) of a pre-pandemic cohort of healthy donors (n=27), and healthy donors (n=786) and convalescent COVID-19 patients (n=1, 413). For clonotypes containing different TCRα or TCRβ sequences, the occurrence was calculated using pooled different sequences (columns K and I). Magnification is shown as COVID-19/Healthy (C/H) (column J, left). Clonotypes are listed in the order of magnitude of TCRβ expansion. *: Clonotype was significantly expanded in recovered patients ($p<0.05$) (column J, right).

[FIG. 10-2]

FIG. 10 shows TCRα pairs of public Tfhs and epitopes they recognize. (B) TCR pairs for each clonotype listed in (A) were reconstituted in reporter cells and tested in the presence of shared HLA-expressing HEK293T cells or autologous APCs. Expression of paired TCRs on reporter cells indicated by surface CD3 expression is shown in histograms. Coloring: reporter cells reconstituted with TCR pairs. Empty: parent cell. GFP reporter activity was displayed as a heatmap. Clonotypes 1 and 6 did not respond to the S peptide pool. Clonotype 8 TCRαβ was not expressed on the cell surface. (C) The location of the epitope described in (B) is highlighted in red in the 3D structure of the SARS-Cov-2 S protein (PDB code: 6XR8). The frequency of mutations defined compared to Wuhan-Hu-1 (mutation rate) was calculated based on data from CoV-GLUE enabled by GISAID-derived data.

DESCRIPTION OF EMBODIMENTS

Figure 1:
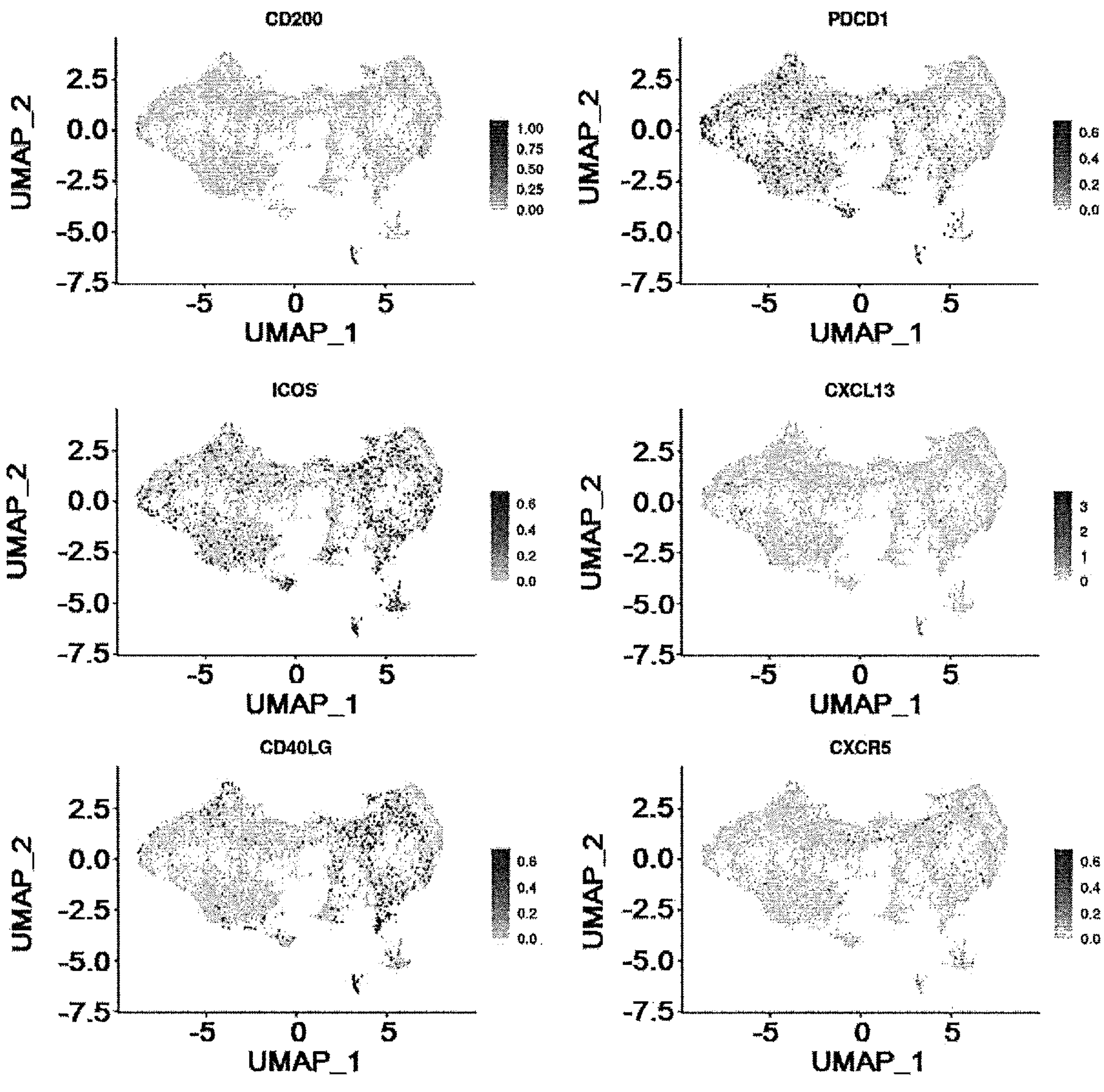
FIG. 1 is a diagram showing the identified TCR expressed in Tfh cells derived from COVID-19 patients. UMAP projection of 18661 T cells derived from patient-derived PBMC. Each dot corresponds to a single cell and is color-coded according to cell type. Standard Tfh cell markers CD200, ICOS, CD40LG, PDCD1, CXCL13, and CXCR5 were used to label Tfh clusters displayed in the UMAP plot.

The present disclosure is described hereinafter while showing the best mode thereof. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present disclosure pertains. In case of a contradiction, the present specification (including the definitions) takes precedence.

The definitions and/or basic technical contents of the terms that are particularly used in the present specification are described as appropriate in the following.

Definition, Etc.

In the present specification, the "follicular T cell" refers to a helper T cell with a shared TCR that regulates B cell maturation and activation, and antibody production. It is also referred to as a follicular helper T cell, and follicular T cell is used interchangeably in the present specification to mean the same as a follicular helper T cell.

In the present specification "SARS-CoV-2" refers to Severe Acute Respiratory Syndrome Coronavirus 2, which is a type of coronavirus and is the causative virus that causes COVID-19.

In the present specification, the "specific" means that an antibody or fragment thereof, or a cell containing same recognizes and binds a target with higher affinity than any other target.

In the present specification, the "sequence of a molecule expressed by SARS-CoV-2 or a part thereof" refers to a protein or a nucleic acid expressed from a nucleic acid possessed by severe acute respiratory syndrome coronavirus 2, which is a type of coronavirus, or a part thereof. The peptide of the present disclosure is a specific amino acid sequence contained in the SARS-CoV-2 genome and is a peptide composed of general amino acids. The induced T cell phenotype is unique because the T cell receptor of follicular T cells obtained from multiple patients recognizes the peptide. DRB15:01/02 is a relatively common HLA allele in Japanese (15-20%), and is also reported to be a SARS-CoV-2 infection risk allele. Therefore, when SARS-CoV-2-infected individuals are used as the population, a relatively large number of individuals are the targets for the SARS-CoV-2-specific follicular T cells of the present disclosure.

In the present specification, the "spike protein" is called an envelope protein, which is a type of protein expressed by viruses, and is sometimes abbreviated as S. Specifically, the "spike protein" refers to a protruding protein arranged on the surface of a virus envelope, is a viral glycoprotein, and sometimes exists as a multimer. It plays an essential role in adsorption and invasion of enveloped viruses into host cells. For example, in Sendaivirus, there are two kinds of spike proteins consisting of hemagglutinin-neuraminidase (HN) glycoprotein and fusion glycoprotein (F). Influenza viruses have two kinds of spike proteins, hemagglutinin (trimer) (HA) and neuraminidase (tetramer) (NA). In the SARS virus, the spike glycoprotein exists as the spike protein. Ebola hemorrhagic fever virus strain Zaire has a protruding EboZ envelope protein with a length of about 10 nm as a spike protein.

In the present specification, the "epitope" is a molecule or moiety, also known as an antigen determinant, that is recognized by the immune system, such as an antibody, B cell, or T cell. When used in the present specification, the "epitope" is a molecule capable of binding to a binding moiety (e.g., an antibody or antigen-binding fragment thereof) described in the present specification. Epitopes generally consist of chemically active surface groups of molecules such as amino acids or sugar side chains and generally have specific three-dimensional structural characteristics, and specific electric charge characteristics.

In the present specification, the "probe in which an epitope is presented to HLA" refers to a probe for presenting an epitope to HLA. By performing an assay using this probe, the establishment of an immune system can be examined by the presence or absence of a cell that binds to the probe. While being a probe, HLA and epitope peptide may be integrated as polypeptide in some cases, and they may not be integrated and peptide may be carried on HLA in some cases.

In the present specification, the "specifically binds to TCR" refers to specific binding to T cell receptor (TCR). In the present specification, the "enhancing acquisition of immunity" refers to promoting acquisition of immunity such as the innate immunity and acquired immunity, against antigens. For example, maturation and activation of B cells, promoted control of antibody production, and the like by follicular T cells can be mentioned.

In the present specification, the "protective antibody" refers to an antibody that is responsible for immunity against infectious pathogens, particularly the ability to inhibit viral infection, which is observed in active immunity or passive immunity.

In the present specification, the "public follicular T cell" refers to a helper T cell having a TCR shared between individuals that controls maturation and activation of B cells, and antibody production. It is interchangeably used to mean the same as public follicular helper T cells and public Tfh cells.

In the present specification, the "operably linked" means that a polypeptide encoded by a nucleic acid is linked to an element such that the polypeptide is expressed in a state exhibiting biological activity under the control of the element such as a promoter.

In the present specification, the "viral antigen" refers to a part or all of a virus to be a target to which an immune response is desired to be induced, and refers to an antigen that elicits an immune response when administered to a host. Peptides, the whole (lysates), and the like can be used. Alternatively, virus-like particles (VLP) may be formed and utilized. Examples of the viral antigen target include rhino virus, adenovirus, coronavirus, RS virus, influenza virus, parainfluenza virus, enterovirus, and the like.

The Coronaviridae, one of the targets of the present disclosure, is the largest virus family belonging to the Noroviruses, including the Coronaviridae, Arteriviridae, Mesoniviridae, and Roniviridae. Coronaviruses are further divided into α-, β-, γ-, and δ-coronaviruses, among which α- and β-coronaviruses cause 10-30% of human respiratory tract and intestinal infections.

Viruses of the genus coronavirus are enveloped RNA viruses. The diameter thereof is about 100-160 nm and its genetic material is the largest of all RNA viruses. There are three glycoproteins on the surface of virus particles: Spike (spinous sugar) protein (S, Spike Protein, receptor binding site, cell lysis and antigen); Vesicular Membrane Glycoprotein (E, Envelope Protein, small, protein that binds to the cell membrane); Membrane Glycoprotein (M, Membrane Protein, membrane transporter of nutrients, assembles new virus budding and virus envelope formation). A minority class is the hemoglobin glycoprotein (HE protein, Haemaglutinin-esterase). Viruses primarily invade through binding of viral spike protein (S protein) and host cell receptor, and determine the tissues or host. Both the N-terminal domain ($S_1$-NTD) and the C-terminal domain (S1-CTD) of the coronavirus S protein S1 subunit can be receptor binding domains (RBD). S1-NTD is considered to bind to sugar receptors, and S1-CTD to protein receptors.

Coronaviruses known as causative viruses of cold-like syndromes that infect humans include the following: HCoV-HKU1, HCoV-OC43, SARS-CoV, MERS-CoV, and SARS-CoV-2.

The nucleic acid of the coronavirus is a non-segmented, single-stranded (+) RNA with a size of 27-31 kDa, the longest ribonucleic acid RNA among RNA viruses, the RNA strand has 5' methylation "prevention", and the 3' has a Poly(A) "tail" structure. This structure is very similar to eukaryotic mRNA. Since the genomic RNA itself is an important structural base that plays a role in translation, the process of RNA-DNA-RNA transcription is omitted. Coronaviruses have a very high recombination rate between RNA and RNA, and it is this recombination rate that causes the virus to mutate. After recombination, the RNA sequence changes, resulting in a change in the amino acid sequence of the nucleic acid code, and the antigenicity changes due to changes in the amino acids constituting the protein, which is considered to limit the development of vaccine.

As the protein, in addition to spike (protrusion, S) protein, envelope (E) protein, nucleocapsid protein (N), integral membrane protein (M), and the like can be used. In addition, PLPro (encoding M protease, etc.), 3CLPro, RdRp (RNA-dependent RNA polymerase), and Hel (helicase), which are present in ORF1a, are also encoded (Lam, T. T., Shum, M. H., Zhu, H. et al. Identifying SARS-CoV-2 related coronaviruses in Malayan pangolins. Nature (2020); Andersen, K. G., Rambaut, A., Lipkin, W. I. et al. The proximal origin of SARS-CoV-2. Nat Med 26, 450-452 (2020)), and these can also be used. As the dendritic cells, dendritic cells in which ACE2, to which S protein binds, has been inactivated or removed may be used. Alternatively, the AI system "Cascade Eye" may be used to construct a pathway map of COVID-19 and the identified important molecules and genes involved in infectious diseases may be used. Alternatively, the thousands of SARS-CoV-2 genome sequences identified in the research results published on the website "bioRxiv" may be analyzed and epitopes (potential targets for vaccines) against 100 HLA alleles (various types of immunity) most commonly found in people around the world may also be used (Artificial intelligence predicts the immunogenic landscape of SARS-CoV-2: toward universal blueprints for vaccine designs; Brandon Malone, Boris Simovski, Clement Moline, Jun Cheng, Marius Gheorghe, Hugues Fontenelle, Ioannis Vardaxis, Simen Tennoe, Jenny-Ann Malmberg, Richard Stratford, Trevor Clancy; bioRxiv 2020.04.21.052084; doi: doi.org/10.1101/2020.04.21.052084).

HLA-binding properties should also be considered. Complexes of HLA class I molecules and SARS-CoV antigen-derived peptides that are recognized by cytotoxic (killer) T cells when the killer T cells recognize SARS coronavirus (SARS-CoV)-infected cells and eliminate them by damaging them have been identified and such class information can be used. For SARS-CoV, 26 types of peptides derived from S, M, and N antigens have been identified that bind to HLA-A2 (A*0201) molecules possessed by approximately 20-30% of humans. This approach can be used to identify antigenic peptides to be used in a Japanese people cohort for the dendritic cell preparation of the present disclosure. Six types of peptides have been identified that can induce an immune response in killer T cells in HLA-A2 (A*0201) transgenic mice after immunizing with these synthetic peptides, and they can be used. Using a similar method and HLA-A24 (A*2402) Tgm, 23 types of peptides derived from SARS-CoV antigens that bind to HLA-A24 (A*2402) molecules that are most frequent in the Japanese population and possessed by 60% thereof have been identified, and this approach can be used to identify antigen peptides to be used for a Japanese people cohort for the dendritic cell preparation of the present disclosure (Chen, Y.-Z., Liu, G., Senju, S., Wang, Q., Irie, A., Haruta, M., . . . . Nishimura, Y. (2010). Identification of SARS-CoV Spike Protein-Derived and HLA-A2-Restricted Human CTL Epitopes by Using a New Muramyl Dipeptide-Derivative Adjuvant. International Journal of Immunopathology and Pharmacology, 165-177. doi.org/10.1177/039463201002300115). Using such information, it is possible to identify viral antigens that bind to HLA-A2 (A*0201) or HLA-A24 (A*2402) recognized by killer T cells that contribute to the elimination of SARS-CoV-2 (as for HLA type in the case of non-Japanese, HLA type unique to the person other than Japanese). The dendritic cell vaccine of the present disclosure, which is produced by inducing differentiation of dendritic cells from human ES cells expressing these HLAs, is expected to activate killer T cells in an antigen-specific manner and prevent worsening into severe conditions caused by cytokine storm and the like. Representative antigen peptides used in the present disclosure may be HLA-binding or HLA-unbinding. For binding, a single peptide can also be used, but for non-binding, use of multiple overlapped peptides or electroporation of viral nucleic acid is preferred.

There are two major types of T cells: CD8+ T cells and CD4+ T cells. These two types of T cells are essentially different in the antigens they recognize. CD8+ T cells recognize a peptide, typically made up of nine amino acids, bound to a type of HLA (MHC) called class I. On the other hand CD4+ T cells recognize MHC-binding peptides called class II. The length of peptides that bind to HLA (MHC) class II is considered to be, for example, but not limited to, 15 to 24 amino acids. HLA (MHC) class I molecules are expressed in all somatic cells, and bind and present protein fragments produced by self-cells. HLA (MHC) class II molecules are expressed in limited cells such as antigen-presenting cells such as macrophages and dendritic cells, and B cells. Unlike normal somatic cells, antigen-presenting cells take in proteins from the outside world, degrade them, and then combine them with HLA (MHC) class I and II molecules and present them. Therefore, CD8+ T cells primarily recognize endogenous HLA (MHC) class I-restricted antigens on somatic cells, whereas CD4+ T cells recognize exogenous HLA (MHC) class II-restricted antigens on antigen-presenting cells. In humans, MHC class I is HLA A, B, C, and MHC class II is HLA DR, DQ, DP.

In the present specification, the dosage form of "pharmaceutical (composition)" is not particularly limited, and may be a solid, semi-solid, or liquid preparation, and can be selected according to the purpose of use, and the like. In the case of cellular preparations, they are generally provided as liquid preparations, but may also be provided as freezed or freeze-dried preparations. The dosage forms of pharmaceutical compositions are described, for example, in the General Rules for Pharmaceutical Preparations of the Japanese Pharmacopoeia, Seventeenth Edition or Eighteenth Edition, equivalents in other countries, or the like.

In the present specification, the "vaccine" refers to a factor containing antigens or cells and capable of, when administered in vivo, producing antibodies and enhancing cellular immunity, or a substance capable of producing such factors. Antigen means a selected substance and a composition for inducing an immune response to the substance in vertebrates such as human and the like.

In the present specification, the "therapy" refers to a cure or improvement of a disease or condition, or suppression of condition. Therapy can be judged using parameters as follows: period from hospitalization to discharge; 8-point ordinal scale at appropriate time point; early warning score at appropriate point (NEWS Score); average change in NEWS Score from the time of allocation (Day 1) to an appropriate time point; SOFA score at an appropriate time point; changes in the amount of COVID-19 virus RNA in the specimen (tested using nucleic acid amplification method) or changes in the amount of antibodies; oxygen supply (e.g., non-invasive ventilation or high-flow oxygen, invasive mechanical ventilation, or extracorporeal membrane oxygenation)

(ECMO) or other methods) (see Examples, etc.). Reducing the rate of severe disease also falls within the scope of therapy. It refers to the prevention of exacerbation, preferably maintaining the current condition, more preferably alleviation, further preferably disappearance of a disease or disorder, in case where such state occurs, including being capable of exerting an improving effect or preventing effect on a disease or one or more conditions accompanying the disease in a patient. A suitable therapy based on preliminary diagnosis may be referred to as "companion therapy" or "tailor made therapy" and a diagnostic agent therefor may be referred to as "companion diagnostic agent".

In the present specification, the "prophylaxis" means preventing the onset of a disease or condition.

In the present specification, the "treatment" means any treatment for a disease or condition and includes treatment and prophylaxis.

In the present specification, the "diagnosis" refers to identifying various parameters associated with a disease, disorder, or condition (e.g., COVID-19) or the like in a test subject to determine the current or future state of such a disease, disorder, or condition. The condition in the body can be investigated by using the method, device, or system of the present invention. Such information can be used to select various parameters of the disease, disorder, or condition of a test subject, a formulation to be administered for treatment or prevention or method and the like. In the present specification, the "diagnosis" when narrowly defined refers to diagnosis of the current state, but when broadly defined includes "early diagnosis", "predictive diagnosis", "prediagnosis" and the like. Since the diagnostic method of the present invention in principle can utilize what comes out from a body and can be conducted away from a medical practitioner such as a physician, the present disclosure is industrially useful. In order to clarify that the method can be conducted away from a medical practitioner such as a physician, "assisting" "predictive diagnosis, prediagnosis or diagnosis" may be particularly recited.

In the present specification, the "test subject" refers to an entity which is to be subjected to diagnosis, detection, or treatment, and the like in the present invention (e.g., an organism such as a human, a cell, blood, serum, etc. which has been taken out from an organism, or the like).

In the present specification, the "sample" refers to any substance obtained from a test subject or the like, and includes, for example, a serum or the like. Those skilled in the art can appropriately select a preferable sample based on the descriptions in the present specification.

In the present specification, the "kit" refers to a unit generally providing portions to be provided (e.g., inspection drug, diagnostic drug, therapeutic drug, antibody, label, manual and the like) into two or more separate sections. This form of a kit is preferred when a composition that should not be provided in a mixed state and is preferably mixed immediately before use for safety or the like is intended to be provided. Preferably, such a kit advantageously comprises an instruction or manual describing how the provided portions (e.g., inspection drug, diagnostic drug, or therapeutic drug are used or how a reagent should be handled. When the kit is used in the present specification as a reagent kit, the kit generally contains an instruction or the like describing how to use an inspection drug, diagnostic drug, therapeutic drug, antibody and the like.

In the present specification, the "instruction" is a document with an explanation of the method of use of the present invention for a physician or other users. The instruction has a description of the detection method of the present invention, method of use of a diagnostic agent, or a direction for administration of a medicament or the like. Further, an instruction may have a description instructing oral administration or administration to the esophagus (e.g., by injection or the like) as a site of administration. The instruction is prepared in accordance with a format defined by the regulatory agency of the country in which the present invention is practiced (e.g., the Ministry of Health, Labor and Welfare in Japan, Food and Drug Administration (FDA) in the U.S. or the like), with an explicit description showing approval by the regulatory agency. The instruction is a so-called package insert and is typically provided in, but not limited to, paper media. The instruction may also be provided in a form such as electronic media (e.g., web sites provided on the Internet or emails).

In the present specification, the "functional equivalent" is any entity that has the same target function but a different structure relative to the original entity of interest. Thus, it is understood that a functional equivalent of a "SARS-CoV-2 virus protein" or a part thereof includes one that is not the SARS-CoV-2 virus protein or a part thereof itself, but a mutant or variant (e.g., amino acid sequence variant, etc.) of the SARS-CoV-2 virus protein or a part thereof, which has the biological action of the SARS-CoV-2 virus protein or a part thereof, and one that, at the time of action, can be transformed into the SARS-CoV-2 virus protein or a part thereof itself, or a mutant or variant of the SARS-CoV-2 virus protein or a part thereof (e.g., nucleic acids encoding the SARS-CoV-2 virus protein or a part thereof itself or a mutant or variant of the SARS-CoV-2 virus protein or a part thereof, and vectors, cells, and the like containing the nucleic acids). It is understood that, in the present disclosure, the functional equivalent of a SARS-CoV-2 virus protein or a part thereof can be used in the same manner as the SARS-CoV-2 virus protein or a part thereof, even if not particularly mentioned. Functional equivalents can be found by searching databases and the like. In the present specification, the "search" refers to the use of a certain nucleic acid sequence to find other nucleic acid sequences having specific functions and/or properties, either electronically or by biological or other means. Examples of the electronic search include, but are not limited to, BLAST (Altschul et al., J. Mol. Biol. 215:403-410 (1990)), FASTA (Pearson & Lipman, Proc. Natl. Acad. Sci., USA 85:2444-2448 (1988)), Smith and Waterman method (Smith and Waterman, J. Mol. Biol. 147:195-197 (1981)), Needleman and Wunsch method (Needleman and Wunsch, J. Mol. Biol. 48:443-453 (1970)), and the like. Examples of the biological search include, but are not limited to, stringent hybridization, macroarrays in which genomic DNA is attached to a nylon membrane or the like or microarrays in which genomic DNA is attached to a glass plate (microarray assay), PCR, and in situ hybridization. In the present specification, the genes used in the present invention are intended to also include corresponding genes identified by such electronic search and biological search.

In the present specification, the "protein", "polypeptide", "oligopeptide" and "peptide" are used herein in the same meaning and refer to an amino acid polymer of any length. The polymer may be straight, branched or cyclic. An amino acid may be a naturally-occurring, non-naturally occurring or altered amino acid. The term may also encompass those assembled into a complex of multiple polypeptide chains. The term also encompasses naturally-occurring or artificially altered amino acid polymers. Examples of such modification include disulfide bond formation, glycosylation, lipidation, acetylation, phosphorylation, and any other manipulation or modification (e.g., conjugation with a labeling component). The definition also encompasses, for example, polypeptides comprising one or more analogs of an amino acid (e.g., including non-naturally occurring amino acids and the like), peptide-like compounds (e.g., peptoids) and other alterations known in the art. In the present specification, the "amino acid" is a general term for organic compounds having an amino group and a carboxyl group. When an antibody according to an embodiment of the present invention contains a "specific amino acid sequence", any amino acid in the amino acid sequence may be chemically modified. Also, any amino acid in the amino acid sequence may form a salt or solvate. Also, any amino acid in the amino acid sequence may be L-type or D-type. Even in such cases, it can be said that the protein according to the embodiment of the present invention contains the above-mentioned "specific amino acid sequence". Examples of chemical modifications that amino acids contained in proteins undergo in vivo include N-terminal modification (e.g., acetylation, myristoylation, etc.), C-terminal modification (e.g., amidation, glycosylphosphatidylinositol addition, etc.), side chain modification (e.g., phosphorylation, sugar chain addition etc.), and the like. Amino acids can be natural or non-natural as long as they fulfill the purposes of the present invention.

In the present specification, the "polynucleotide", "oligonucleotide", and "nucleic acid" are used herein to have the same meaning and refer to a polymer of nucleotides of any length. The terms also encompass "oligonucleotide derivative" or "polynucleotide derivative". The "oligonucleotide derivative" and "polynucleotide derivative" are interchangeably used and refer to an oligonucleotide or polynucleotide comprising a derivative of a nucleotide or having a bond between nucleotides that is different from ordinary bonds. Specific examples of such oligonucleotides include: 2'-O-methyl-ribonucleotide; oligonucleotide derivatives with a phosphodiester bond in an oligonucleotide converted into phosphorothioate bond; oligonucleotide derivatives with a phosphodiester bond in an oligonucleotide converted into an N3'-P5' phosphoramidate bond; oligonucleotide derivatives with a ribose and a phosphodiester bond in an oligonucleotide converted into a peptide nucleic acid bond; oligonucleotide derivatives with a uracil in an oligonucleotide substituted with a C-5 propynyl uracil; oligonucleotide derivatives with a uracil in an oligonucleotide substituted with a C-5 thiazole uracil; oligonucleotide derivatives with a cytosine in an oligonucleotide substituted with a C-5 propynyl cytosine; oligonucleotide derivatives with a cytosine in an oligonucleotide substituted with a phenoxathiine-modified cytosine; oligonucleotide derivatives with a ribose in DNA substituted with a 2'-O-propylribose; oligonucleotide derivatives with a ribose in an oligonucleotide substituted with a 2'-methoxyethoxy ribose; and the like. Unless noted otherwise, specific nucleic acid sequences are intended to encompass sequences that are explicitly set forth, as well as their conservatively altered variants (e.g., degenerate codon substitutes) and complementary sequences. Specifically, a degenerate codon substitute can be achieved by making a sequence in which the third position of one or more selected (or all) codons is substituted with a mixed base and/or deoxyinosine residue (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). In the present specification, the "nucleic acid" is also interchangeably used with gene, cDNA, mRNA, oligonucleotide, and polynucleotide. In the present specification, the "nucleotide" may be naturally-occurring or non-naturally-occurring.

In the present specification, the "gene" refers to a factor defining a genetic trait, and "gene" may refer to "polynucleotide", "oligonucleotide", and "nucleic acid".

In the present specification, the "homology" of genes refers to the degree of identity of two or more genetic sequences with respect to one another, and having "homology" generally refers to having a high degree of identity or similarity. Therefore, the identity or similarity of sequences is higher when homology of two genes is higher. Whether two types of genes have homology can be found by direct comparison of sequences or by a hybridization method under stringent conditions for nucleic acids. When two genetic sequences are directly compared, the genes are homologous typically if DNA sequences are at least 50% identical, preferably at least 70% identical, and more preferably at least 80%, 90%, 95%, 96%, 97%, 98%, or 99% identical between the genetic sequences. Thus, in the present specification, the "homolog" or "homologous gene product" refers to a protein in another species, preferably mammal, exerting the same biological function as a protein constituent of a complex which will be further described herein. Such a homolog may be also called "ortholog gene product". It is understood that such homolog, homologous gene product, ortholog gene product, and the like can also be used as long as they meet the purpose of the present invention.

Amino acids may be mentioned herein by either their commonly known three letter symbols or their one character symbols recommended by the IUPAC-IUB Biochemical Nomenclature Commission. Similarly, nucleotides may be mentioned by their commonly recognized one character codes. Comparison of similarity, identity, and homology of an amino acid sequence and a base sequence is calculated herein by using a sequence analysis tool BLAST with default parameters. For example, identity can be searched using BLAST 2.2.28 (published on Apr. 2, 2013 or may be more recent one) of the NCBI. Herein, values for identity generally refer to a value obtained when aligned under the default conditions using BLAST described above. However, when a higher value is obtained by changing a parameter, the highest value is considered the value of identity. When identity is evaluated in a plurality of regions, the highest value thereamong is considered the value of identity. Similarity is a value calculated by taking into consideration a similar amino acid in addition to identity.

In one embodiment of the present invention, "several" may be, for example, 8, 7, 6, 5, 4, 3, or 2, and may be not more than any of those values. It is known that polypeptides that have undergone deletion, addition, insertion, or substitution with other amino acids of one or several amino acid residues retain biological activity thereof (Mark et al., Proc Natl Acad Sci USA. 1984 September; 81 (18): 5662-5666., Zoller et al., Nucleic Acids Res. 1982 Oct. 25; 10 (20): 6487-6500., Wang et al., Science. 1984 Jun. 29; 224 (4656): 1431-1433.). It is possible to determine whether or not it is a functional equivalent by measuring the activity by an appropriate method by which deletion, etc., have been made.

In one embodiment of the present invention, "90% or more" may be, for example, 90, 95, 96, 97, 98, 99, or 100% or more, and may be within the range of any two of those values. The above-mentioned "homology" may be calculated as the percentage of the number of homologous amino acids between two or more amino acid sequences, according to methods known in the art. Before calculating the percentage, the amino acid sequences of the groups of amino acid sequences to be compared are aligned and gaps are introduced in part (s) of the amino acid sequences if necessary to maximize the percentage of the same amino acids. Methods for alignment, calculation method of percentage, comparison method, and computer programs related thereto are conventionally well known in the technique field (e.g., BLAST, GENETYX etc.). In the present specification, the "homology" can be expressed in terms of values measured by BLAST of NCBI unless otherwise specified. Blastp can be used as the default setting for the algorithm for comparison of amino acid sequences in BLAST. The measurement results are quantified as Positives or Identities.

The substance in the present disclosure may be purified. In the present specification, the "purified" substance or biological factor (e.g., nucleic acid, protein or the like) refers to a substance or a biological agent wherein at least a part of an agent naturally accompanying the substance or biological agent has been removed. Thus, the purity of a biological agent in a purified biological agent is generally higher than the purity in the normal state of the biological agent (i.e., concentrated). The term "purified" as used herein refers to the presence of preferably at least 75% by weight, more preferably at least 85% by weight, still more preferably at least 95% by weight, and most preferably at least 98% by weight of a biological agent of the same type. The substance or biological agent used in the present disclosure is preferably a "purified" substance. An "isolated" substance or biological agent (e.g., nucleic acid, protein or the like) used in the present invention refers to a substance or a biological agent wherein an agent naturally accompanying the substance or biological agent has substantially been removed. The term "isolated" used in the present specification varies according to the purpose thereof and thus is not necessarily shown in purity. Where necessary, it refers to the presence of preferably at least 75% by weight, more preferably at least 85% by weight, still more preferably at least 95% by weight, and most preferably at least 98% by weight of a biological agent of the same type. The substance used in the present invention is preferably an "isolated" substance or biological agent.

In the present specification, the "corresponding" amino acid, nucleic acid, or portion refers to an amino acid or a nucleotide which has or is expected to have, in a certain polypeptide molecule or polynucleotide molecule (e.g., polynucleotide encoding spike protein, etc.), similar action as a predetermined amino acid, nucleotide, or portion in a reference polypeptide or a polynucleotide for comparison, and particularly in the case of enzyme molecules, refers to an amino acid which is present at a similar position in an active site and makes a similar contribution to catalytic activity, and refers to the corresponding part (e.g., heparan sulfate, etc.) in the case of composite molecules. For example, for an antisense molecule, it can be a similar moiety in an ortholog corresponding to a specific moiety of the antisense molecule. A corresponding amino acid can be a specific amino acid subjected to, for example, cysteination, glutathionylation, S—S bond formation, oxidation (e.g., oxidation of methionine side chain), formylation, acetylation, phosphorylation, glycosylation, myristylation or the like. Alternatively, a corresponding amino acid can be an amino acid responsible for dimerization. Such a "corresponding" amino acid or nucleic acid may be a region or a domain over a certain range. Thus, it is referred herein as a "corresponding" region or domain in such a case. Such corresponding region or domain is useful in designing a composite molecule in the present specification.

For example, even in the case of a virus that mutates rapidly, such as SARS-CoV-2, if a mutation occurs in the corresponding portion of the viral protein, for example, the corresponding peptide sequence of SEQ ID NO: 13 of the present disclosure can be identified.

In the present specification, the "corresponding" gene (e.g., polynucleotide sequence or molecule) refers to a gene (e.g., polynucleotide sequence or molecule) in a certain species which has or is expected to have similar action as a predetermined gene in a reference species for comparison. When there is a plurality of genes having such action, the corresponding gene refers to a gene having the same evolutionary origin. Hence, a gene corresponding to a certain gene may be an ortholog of such a gene. Therefore, each S protein of SARS-CoV-2 before mutation can find a corresponding S protein in the mutant SARS-CoV-2. Such a corresponding gene can be identified by using a technique that is well known in the art. For example, a corresponding gene in a certain animal (e.g., mouse), or gene (e.g., S protein, etc.) to be the standard of the corresponding gene, can be found by search on a database containing the sequence for the animal using the sequence of SEQ ID NO: 1, or SEQ ID NO: 2 as a query sequence.

In the present specification, the "fragment" refers to a polypeptide or polynucleotide with a sequence length of 1 to n−1 with respect to the full length polypeptide or polynucleotide (with length n). The length of a fragment can be appropriately changed in accordance with the objective. Examples of the lower limit of such a length include 3, 4, 5, 6, 7, 8, 9, 10, 15, 20, 25, 30, 40, 50 and more amino acids for a polypeptide. Lengths represented by an integer that is not specifically listed herein (e.g., 11 and the like) also can be suitable as a lower limit. Further, examples of the length include 5, 6, 7, 8, 9, 10, 15, 20, 25, 30, 40, 50, 75, 100, and more nucleotides for a polynucleotide. Lengths represented by an integer that is not specifically listed herein (e.g., 11 and the like) also can be suitable as a lower limit. In the present specification, such a fragment is understood to be within the scope of the present invention, for example, when a full length version functions as a marker or a target molecule, as long as the fragment itself also functions as a marker or a target molecule.

According to the present invention, the term "activity" refers to the function of a molecule in its broadest sense and can be taken into account in evaluating functional equivalents. Not intended to be limitative, the activity generally includes a biological function, biochemical function, physical function, and chemical function of a molecule. Examples of activity include enzymatic activity, an ability to interact with other molecules, an ability to activate, promote, stabilize, inhibit, suppress, or destabilize functions of other molecules, stability, and an ability to localize at a specific position in a cell. When applicable, the term also relates to a function of a protein complex in the broadest sense.

In the present specification, the "biological function", when referring to a certain gene or a nucleic acid molecule or a polypeptide related thereto, refers to a specific function that the gene, the nucleic acid molecule or the polypeptide may have in a living body. Examples of such a function include, but are not limited to, production of a specific antibody, enzyme activity, impartation of resistance and the like.

In the present specification, biological function can be exerted by "biological activity". In the present specification, the "biological activity" refers to the activity possibly possessed by a certain agent (e.g., polynucleotide, protein or the like) in a living body. The biological activity encompasses an activity of exerting a variety of functions (e.g., follicular T cells inducing ability), and also encompasses, for example, an activity of activating or inactivating other molecule by an interaction with a certain molecule. When two agents interact, the biological activity thereof may be a bond between the two molecules and a biological change induced thereby, and for example, two molecules are considered to be bound together if precipitating one molecule using an antibody results in co-precipitation of the other molecule. Observation of such co-precipitation is one example of a determination approach. For example, when a certain agent is an enzyme, the biological activity thereof encompasses enzyme activity thereof. In another example, when a certain agent is a ligand binding to a receptor corresponding to the ligand is encompassed. Such biological activity can be measured by a technique that is well known in the art. Therefore, the "activity" refers to various measurable indicators that indicate or reveal binding (either directly or indirectly) or affect response (i.e., have a measurable effect in response to some exposure or stimulus), such as the affinity of a compound that binds directly to the polypeptide or polynucleotide of the present invention, or the amount of upstream or downstream protein or other similar measure of function after some stimulus or event.

In the present specification, the "expression" of a gene, a polynucleotide, a polypeptide, or the like refers to the gene or the like being subjected to a certain action in vivo to be converted into another form. Preferably, expression refers to a gene, a polynucleotide, or the like being transcribed and translated into a form of a polypeptide. However, transcription to make an mRNA also can be one embodiment of expression. Therefore, the "expression product" in the present specification includes such polypeptide or protein, or mRNA. More preferably, such a polypeptide form can be a form which has undergone post-translation processing.

Those with amino acid sequences with one or more amino acid insertions, substitutions or deletions, or addition to one or both ends in an amino acid sequence can be used as a functional equivalent in the present invention. In the present specification, "one or more amino acid insertions, substitutions or deletions, or addition to one or both ends in an amino acid sequence" refers to an modification with a substitution of a plurality of amino acids or the like to the extent that can occur naturally by a well-known technical method such as site-directed mutagenesis or by natural mutation. A modified amino acid sequence may include, for example, those with insertion, substitutions, deletion, or addition to one or both ends in an amino acid sequence of 1 to 30, preferably 1 to 20, more preferably 1 to 9, further preferably 1 to 5, particularly preferably 1 or 2, amino acids. The altered amino acid sequence may preferably be an amino acid sequence having one or more (preferably 1 or several, or 1, 2, 3, or 4) conservative substitutions in the amino acid sequence, such as S protein. The "conservative substitution" means the replacement of one or more amino acid residues with other chemically similar amino acid residue so as not to substantially alter the function of the protein. Examples include the substitution of one hydrophobic residue by another hydrophobic residue, and the substitution of one polar residue by another polar residue having the same charge. Functionally similar amino acids that can make such substitutions are known in the field for each amino acid. Specific examples of non-polar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, asparagine, and cysteine. Examples of positively charged (basic) amino acids include arginine, histidine, and lysine. Examples of negatively charged (acidic) amino acids include aspartic acid and glutamic acid.

In the present specification, the "antigen" refers to any substrate that can be specifically bound by an antibody molecule. In the present specification, the "immunogen" refers to an antigen capable of initiating lymphocyte activation resulting in an antigen-specific immune response. In the present specification, the "epitope" or "antigen determinant" refers to the site in an antigen molecule where an antibody or lymphocyte receptor binds. Methods for determining epitopes are well known in the art, and such epitopes can be determined by those skilled in the art by using such well-known and conventional techniques, once a primary sequence of nucleic acid or amino acid is provided.

In the present specification, the dosage form of "pharmaceutical (composition)" is not particularly limited, and may be a solid, semi-solid, or liquid preparation, and can be selected according to the purpose of use, and the like. In the case of cellular preparations, they are generally provided as liquid preparations, but may also be provided as freezed or freeze-dried preparations. The dosage forms of pharmaceutical compositions are described, for example, in the General Rules for Pharmaceutical Preparations of the Japanese Pharmacopoeia, Seventeenth Edition, equivalents in other countries, or the like. Examples of the effective amount include, but are not limited to, administration of $5\times10^6$ antigen peptide-pulsed dendritic cells subcutaneously near the axillary or inguinal lymph node, and $1\times10^6$ cells, $2\times10^6$ cells, $3\times10^6$ cells, $4\times10^6$ cells, $5\times10^6$ cells, $6\times10^6$ cells, $7\times10^6$ cells, $8\times10^6$ cells, $9\times10^6$ cells, $1\times10^7$ cells, and the like.

In the present specification, the "medicament", "agent", or "factor" (all corresponding to agent in English) is used broadly and may be any substance or other elements (e.g., light, radiation, heat, electricity and other forms of energy) as long as the intended objective can be achieved. Examples of such a substance include, but are not limited to, protein, polypeptide, oligopeptide, peptide, polynucleotide, oligonucleotide, nucleotide, nucleic acid (including for example, DNAs such as CDNA and genomic DNA, RNAs such as mRNA), polysaccharide, oligosaccharide, lipid, organic small molecule (e.g., hormone, ligand information transmitting substance, organic small molecule, molecule synthesized by combinatorial chemistry, small molecule that can be used as medicine (e.g., small molecule ligand and the like), and the like) and a composite molecule thereof.

The "active ingredient" in the present specification refers to an ingredient contained in the composition of the present disclosure in an amount necessary to achieve the desired effect of treatment, prevention, or inhibition of progression. Other ingredients may also be included as long as the effectiveness is not impaired below the desired level. In addition, the medicaments, compositions, etc. of the present disclosure may be formulated. In addition, the administration route of the medicament, composition, etc. of the present disclosure may be either oral or parenteral, and can be appropriately set according to the form of the preparation.

In the present specification, the "vaccine" refers to a factor containing antigens or cells and capable of, when administered in vivo, producing antibodies and enhancing cellular immunity, or a substance capable of producing such factors. Antigen means a selected substance and a composition for inducing an immune response to the substance in vertebrates such as human and the like.

In the present specification, the "adjuvant" refers to a substance that can enhance, hasten, or prolong the immune response induced by a vaccine immunogen.

In the present specification, the "conservative substitution" of amino acids refers to replacing an amino acid residue with a different amino acid residue having a side chain with similar physiochemical properties. For example, conservative substitution can be made between amino acid residues having hydrophobic side chains (e.g., alanine, valine, isoleucine, leucine, proline, tryptophan, phenylalanine, methionine, etc.); between amino acid residues having neutral hydrophilic side chains (e.g. glycine, serine, threonine, tyrosine, glutamine, asparagine, cysteine, etc.); between amino acid residues having acidic side chain (e.g. aspartic acid, glutamic acid, etc.); between amino acid residues having basic side chain (e.g. arginine, histidine, lysine, etc.), or between amino acid residues having aromatic side chain (e.g., tryptophan, phenylalanine, tyrosine, etc.). As is known in the art, conservative substitution generally does not cause remarkable changes in the steric structure of the protein and may therefore preserve the biological activity of the protein.

PREFERRED EMBODIMENTS

Preferred embodiments of the present disclosure are described below. Embodiments provided below are provided to facilitate the understanding of the present disclosure. The scope of the present disclosure should not be limited to the following descriptions. Thus, it is apparent that those skilled in the art can make appropriate modifications within the scope of the present disclosure by referring to the descriptions herein. The following embodiments of the present disclosure can be used alone or in combination.

The present disclosure relates generally to compositions containing SARS-CoV-2 protein or a part thereof, or a functional equivalent thereof or related techniques for inducing follicular T cells. Here, follicular T cells may be reactive with SARS-CoV-2.

Follicular T cells may also be reactive with coronaviruses other than SARS-CoV-2, may be specific to SARS-CoV-2, and may be specific only to SARS-CoV-2.

In one embodiment, the present disclosure provides a composition containing an epitope specific to the SARS-CoV-2 virus, for inducing follicular T cells. Here, the epitope may be reactive only with SARS-CoV-2 virus, or may be reactive with other viruses (e.g., other types of coronaviruses).

In one embodiment, the present disclosure provides a composition containing an epitope specific to the SARS-CoV-2 virus, for inducing follicular T cells. In some embodiment, the follicular T cell can be a public follicular T cell. Since V(D)J recombination is a random process, it has been considered difficult to share TCR between individuals. However, public T cell responses that share the same TCR have been widely observed at various points in the immune response when multiple individuals respond to the same antigenic epitope. The present disclosure identifies for the first time a public TCR specific to the SARS-CoV-2 virus and its MHC and antigenic epitopes to promote efficient immune responses, particularly those of B cells that produce neutralizing antibodies, and is very beneficial.

In one embodiment, an epitope specific to SARS-CoV-2 virus may contain a molecule or a part thereof expressed by the SARS-CoV-2 virus. In a certain embodiment, an epitope specific to SARS-CoV-2 virus may contain a spike protein expressed by SARS-CoV-2 virus or a part thereof. In some embodiment, an epitope specific to SARS-CoV-2 virus may contain the amino acid sequence shown in SEQ ID NO:1. In certain embodiments, in some embodiment, an epitope specific to SARS-CoV-2 virus consists of the amino acid sequence shown in SEQ ID NO:1. The epitope of the present disclosure preferably does not become a B cell antigen, and is about 20 mer at most. The epitope of the present disclosure preferably does not have a structure (secondary structure, tertiary structure, etc.).

In another embodiment, SARS-CoV-2 protein or a part thereof of the present disclosure may contain SEQ ID NO: 5 wherein $X_1$ may be any amino acid,
$X_2$ may be any amino acid,
$X_3$ may be Q or a conservatively substituted amino acid thereof,
$X_4$ may be any amino acid,
$X_5$ may be T or a conservatively substituted amino acid thereof,
$X_6$ may be any amino acid,
$X_7$ may be any amino acid,
$X_9$ may be any amino acid, and
$X_9$ may be any amino acid.

In some embodiment, the SARS-CoV-2 protein or a part thereof of the present disclosure may contain SEQ ID NO: 5 wherein $X_1$ may be any amino acid,
$X_2$ may be any amino acid,
$X_3$ may be Q,
$X_4$ may be any amino acid,
$X_5$ may be T,
$X_6$ may be any amino acid,
$X_7$ may be any amino acid,
$X_8$ may be any amino acid, and
$X_9$ may be any amino acid.

In other embodiment, the SARS-CoV-2 protein or a part thereof of the present disclosure may contain SEQ ID NO: 5 wherein $X_1$ may be I or a conservatively substituted amino acid thereof,
$X_2$ may be A or a conservatively substituted amino acid thereof,
$X_3$ may be Q or a conservatively substituted amino acid thereof,
$X_4$ may be Y or a conservatively substituted amino acid thereof,
$X_5$ may be T or a conservatively substituted amino acid thereof,
$X_6$ may be S or a conservatively substituted amino acid thereof,
$X_7$ may be A or a conservatively substituted amino acid thereof,
$X_8$ may be L or a conservatively substituted amino acid thereof, and
$X_9$ may be L or a conservatively substituted amino acid thereof.

In some embodiment, the SARS-CoV-2 protein or a part thereof of the present disclosure may contain SEQ ID NO: 5 wherein $X_1$ may be I or a conservatively substituted amino acid thereof,
$X_2$ may be A or a conservatively substituted amino acid thereof,
$X_3$ may be Q,
$X_4$ may be Y or a conservatively substituted amino acid thereof,
$X_5$ may be T,
$X_6$ may be S or a conservatively substituted amino acid thereof, $X_7$ may be A or a conservatively substituted amino acid thereof, $X_8$ may be L or a conservatively substituted amino acid thereof, and $X_9$ may be L or a conservatively substituted amino acid thereof.

In another embodiment, the SARS-CoV-2 protein or a part thereof of the present disclosure may contain SEQ ID NO: 5 wherein $X_1$ may be I, V, A, L, P, W, F, M or G, $X_2$ may be A, V, I, L, P, W, F, M or G, $X_3$ may be Q, $X_4$ may be Y, G, S, T, N, Q, C or F, $X_5$ may be T, $X_6$ may be S, Y, G, N, Q, C, F or T, $X_7$ may be A, L, I, V, P, W, F, M or G, $X_8$ may be L, A, I, V, P, W, F, M or G, and $X_9$ may be L, A, I, V, P, W, F, M or G.

In some embodiment, the SARS-CoV-2 protein or a part thereof of the present disclosure may contain SEQ ID NO: 5 wherein $X_1$ may be I, V, A, L or G, $X_2$ may be A, V, I, L or G, $X_3$ may be Q, $X_4$ may be Y or F, $X_5$ may be T, $X_6$ may be S or T, $X_7$ may be A, L, I, V or G, $X_8$ may be L, A, I, V or G, and $X_9$ may be L, A, I, V or G.

In some embodiment, preferred examples of the conservative substitution include substitution of amino acids within the following groups.

group A: leucine, isoleucine, norleucine, valine, norvaline, alanine, 2-aminobutanoic acid, methionine, o-methylserine, t-butylglycine, t-butylalanine, cyclohexylalanine;

group B: aspartic acid, glutamic acid, isoaspartic acid, isoglutamic acid, 2-aminoadipic acid, 2-aminosuberic acid;

group C: asparagine, glutamine;

group D: lysine, arginine, ornithine, 2,4-diaminobutanoic acid, 2,3-diaminopropionic acid;

group E: proline, 3-hydroxyproline, 4-hydroxyproline;

group F: serine, threonine, homoserine;

group G: phenylalanine, tyrosine

In some embodiment, the SARS-CoV-2 protein or a part thereof of the present disclosure contains SEQ ID NO: 6, SEQ ID NO: 7, SEQ ID NO: 8, SEQ ID NO: 9, SEQ ID NO: 10, SEQ ID NO: 11, or SEQ ID NO: 12.

In some embodiment, the SARS-CoV-2 protein or a part thereof of the present disclosure contains or consists of the amino acid sequence shown in SEQ ID NO: 13.

In some embodiment, the follicular T cell of the present disclosure may have a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: and SEQ ID NO: 31, SEQ ID NO: 32 and SEQ ID NO: 33, SEQ ID NO: 34 and SEQ ID NO: 35, or SEQ ID NO: 36 and SEQ ID NO: 37. These TCR pairs were found in clonotypes that remarkably increased in recovered COVID19 patients as compared with healthy individuals, and all were found in public follicular T cells. Therefore, these clonotypes and TCR pairs thereof, which increased during SARS-CoV-2 infection, contribute to the recovery from mild symptoms of SARS-CoV-2 infection.

In some embodiment, the SARS-CoV-2 protein or a part thereof of the present disclosure may contain the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43, and may be at least 9 amino acids long. These amino acid sequences are recognized by clonotypes that increased remarkably in recovered COVID19 patients as compared with healthy individuals. Therefore, targeting the amino acid sequences recognized by these clonotypes, which increased during SARS-CoV-2 infection, contributes to the recovery from mild symptoms of SARS-CoV-2 infection.

In some embodiment, the SARS-CoV-2 protein or a part thereof of the present disclosure may consist of the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43.

In a certain embodiment, the follicular T cells of the present disclosure can be public follicular T cells.

The peptide of the present disclosure may be a functional equivalent, which may be the original sequence added with an appropriate mutation.

In one aspect of the present disclosure, the composition or medicament of the present disclosure can also be provided as a nucleic acid medicament. In one embodiment, when performing gene therapy or genetic treatment using the nucleic acid medicament of the present disclosure, polynucleotides can be introduced into the genome of cells in order to restore or modify genes and/or gene expression. For example, a therapeutic method in which a normal gene is introduced by using a vector which can be introduced into human cells such as various viral vectors or another delivery system, or the like can be used. The method for introducing the vector can be appropriately selected according to the types of the vector and the host, and the like. When the expression vector is used as an active ingredient of the composition of the present disclosure, for example, the introduction can be performed by injecting an AAV vector or the like into the body.

In one aspect, the present disclosure provides a method for inducing a follicular T cell reactive with SARS-CoV-2, which includes a step of administering SARS-CoV-2 protein or a part thereof, or a functional equivalent thereof to a test subject.

In one aspect, the present disclosure provides a method for inducing a follicular T cell reactive with at least one coronavirus, which includes a step of administering SARS-CoV-2 protein or a part thereof, or a functional equivalent thereof to a test subject.

In one aspect, the present disclosure provides use of a SARS-CoV-2 protein or a part thereof, or a functional equivalent thereof in the production of a medicament for inducing follicular T cells reactive with SARS-CoV-2.

In one aspect, the present disclosure provides use of a SARS-CoV-2 protein or a part thereof, or a functional equivalent thereof in the production of a medicament for inducing a follicular T cell reactive with at least one coronavirus.

In one aspect, the present disclosure provides a SARS-CoV-2 protein or a part thereof, or a functional equivalent thereof for inducing a follicular T cell reactive with SARS-CoV-2.

In one aspect, the present disclosure provides a SARS-CoV-2 protein or a part thereof, or a functional equivalent thereof for inducing a follicular T cell reactive with at least one coronavirus.

<Probe>

In other aspect, the present disclosure provides a polypeptide for presenting to HLA an epitope specific to SARS-CoV-2 virus. These polypeptides can be used as probes. HLA and epitope peptide may be integrated as polypeptide in some cases, and they may not be integrated and peptide may be carried on HLA in some cases.

In one embodiment, an epitope specific to SARS-CoV-2 virus may contain a molecule or a part thereof expressed by the SARS-CoV-2 virus. In a certain embodiment, an epitope specific to SARS-CoV-2 virus may contain a spike protein expressed by SARS-CoV-2 virus or a part thereof. In some embodiment, an epitope specific to SARS-CoV-2 virus may contain the amino acid sequence shown in SEQ ID NO:1. In certain embodiments, in some embodiment, an epitope specific to SARS-CoV-2 virus consists of the amino acid sequence shown in SEQ ID NO:1.

In another aspect, the present disclosure provides an antibody that specifically binds to TCR that interacts with an epitope specific to SARS-CoV-2 virus. In one embodiment, an epitope specific to SARS-CoV-2 virus may contain a molecule or a part thereof expressed by the SARS-CoV-2 virus. In a certain embodiment, an epitope specific to SARS-CoV-2 virus may contain a spike protein expressed by SARS-CoV-2 virus or a part thereof. In some embodiment, an epitope specific to SARS-CoV-2 virus may contain the amino acid sequence shown in SEQ ID NO:1. In certain embodiments, in some embodiment, an epitope specific to SARS-CoV-2 virus consists of the amino acid sequence shown in SEQ ID NO:1.

<TCR-T Cell Therapy>

In a certain embodiment, the present disclosure provides a composition for enhancing immunity acquisition against SARS-CoV-2 virus, containing a follicular T cell specific to SARS-CoV-2 virus. In one embodiment, an epitope specific to SARS-CoV-2 virus may contain a molecule or a part thereof expressed by SARS-CoV-2 virus. In a certain embodiment, an epitope specific to SARS-CoV-2 virus may contain a spike protein or a part thereof expressed by SARS-CoV-2 virus. In some embodiment, an epitope specific to SARS-CoV-2 virus may contain the amino acid sequence shown in SEQ ID NO: 1. In a certain embodiment, in some embodiment, an epitope specific to SARS-CoV-2 virus consists of the amino acid sequence shown in SEQ ID NO: 1.

In one aspect, the present disclosure provides a method for enhancing immunity acquisition against SARS-CoV-2, which includes a step of administering a follicular T cell reactive with SARS-CoV-2.

In one aspect, the present disclosure provides use of a follicular T cell reactive with SARS-CoV-2 in the production of a medicament for enhancing immunity acquisition against SARS-CoV-2.

In one aspect, the present disclosure provides a follicular T cell reactive with SARS-CoV-2, for enhancing immunity acquisition against SARS-CoV-2.

The peptides and the like of the present disclosure can be produced using various methods such as chemical synthesis, genetic engineering, and production using microorganisms.

Those skilled in the art will understand from this disclosure and their knowledge in the art that there are a variety of ways to generate antigens. In general, antigens can be generated either in vitro or in vivo. An antigen may be produced in vitro as a peptide or polypeptide, which may then be formulated into a personalized neoplastic vaccine or immunogenic composition and administered to a subject. As described in further detail in the present specification, such in vitro production can be carried out by various methods known to those skilled in the art, for example, peptide synthesis or expression of peptides/polypeptides from DNA or RNA molecules in any of a variety of bacterial, eukaryotic, or viral recombinant expression systems, followed by purification of the expressed peptides/polypeptides. Alternatively, the antigen may be produced in vivo by introducing an antigen-encoding molecule (e.g., DNA, RNA, viral expression system, etc.) into a subject, followed by expression of the encoded antigen. Methods of in vitro and in vivo production of antigens are also further described herein when they relate to methods of delivery of pharmaceutical compositions and combination therapies.

In Vitro Synthesis of Peptide/Polypeptide

Proteins or peptides can be made by any technique known to those of skill in the art, including expression of proteins, polypeptides or peptides by standard molecular biology techniques, proteins from natural supply source, translation in vitro from natural sources, or isolation of peptides, or chemical synthesis of proteins or peptides. Nucleotide and protein, polypeptide and peptide sequences corresponding to various genes have been previously disclosed and can be consulted in computerized databases known to those skilled in the art. One such database is the National Center for Biotechnology Information's Genbank and GenPept databases located on the National Institutes of Health website. Coding regions of known genes can be amplified and/or expressed using the techniques disclosed in the present specification or as known to those of skill in the art. Alternatively, various commercially available protein, polypeptide and peptide preparations are known to those skilled in the art.

Peptides can be easily chemically synthesized using reagents that do not contain contaminating bacteria or animal substances (Merrifield R B: "Solid phase peptide synthesis I. Synthesis of tetrapeptides". J. Am. Chem. Soc. 85:2149-54, 1963). In specific embodiments, the preparation of antigen peptides is performed by (1) parallel solid-phase synthesis on a multichannel instrument using homogeneous synthesis and cleavage conditions; (2) purification by column stripping on a RP-HPLC column; and rewashing between peptides, but without exchange; followed by (3) analysis by the most informative and limited set of assays. For an individual patient set of peptides, a good manufacturing practice (GMP) footprint can be defined, thus requiring a suite switching procedure only between different patient peptide syntheses.

Alternatively, antigen peptides may be produced in vitro using nucleic acids (e.g., polynucleotides) encoding antigen peptides of the present invention. Polynucleotides may be, for example, DNA, CDNA, PNA, CNA, RNA, either single-stranded and/or double-stranded, or in natural or stabilized form, a polynucleotide having a phosphorothioate backbone, etc., or a combination thereof, and may or may not contain introns, as long as it encodes a peptide. In one embodiment, peptides are produced using in vitro translation. The re are many exemplary systems available to those skilled in the art (e.g., Retic Lysate IVT Kit, Life Technologies, Waltham, MA).

Expression vectors capable of expressing polypeptides can also be prepared. Expression vectors for various cell types are well known in the art and can be selected without undue experimentation. Generally, the DNA is inserted into an expression vector, such as a plasmid, in the proper orientation and correct reading frame for expression. If desired, the DNA may be ligated to appropriate transcriptional and translational regulatory control nucleotide sequences recognized by the desired host (e.g., bacteria). However, such control is generally available in expression vectors. Next, the vector is introduced to cloning host bacteria using standard techniques (e.g., see Sambrook et al. (1989) Molecular Cloning, A Laboratory Manual, Cold Spring Harbor Laboratory, Cold Spring Harbor, N.Y.).

Expression vectors containing the isolated polynucleotides, as well as host cells containing the expression vectors are also contemplated. Antigen peptides may be provided in the form of RNA or cDNA molecules that encode the desired antigen peptide. One or more antigen peptides of the present invention may be provided by a single expression vector.

(Medicament)

The present disclosure can be provided as a medicament. The components contained in the medicament or pharmaceutical composition can be referred to as a medicine and the like.

When the composition, polypeptide and the like of the present disclosure is administered, in the case of oral administration, it may be formulated into various forms such as tablets, granules, fine granules, powders, capsules, and the like. Additives commonly used in formulations such as binders, encapsulating agents, excipients, lubricants, disintegrants and wetting agents may be contained. In addition to these, preparations for oral administration may be formulated as liquids such as oral solutions, suspensions, emulsions, syrups, and the like, or as dry formulations that are redissolved at the time of use.

For parenteral administration, the formulation may be formulated in unit-dose ampoules or multi-dose containers or tubes, and may also contain additives such as stabilizers, buffers, preservatives, and tonicity agents. In addition, the preparation for parenteral administration may be formulated into a powder that can be redissolved in a suitable carrier (sterile water, etc.) at the time of use.

The composition of the present disclosure may contain a pharmaceutically acceptable salt. As the pharmaceutically acceptable salt, for example, inorganic acid salts (such as hydrochlorides, hydrobromides, phosphates, and sulfates), or salts of organic acids (such as acetates, propionates, malonates, and benzoate) may be used.

Pharmaceutically acceptable salts in pharmaceutical compositions further include liquids (water, saline, glycerol and ethanol). Additionally, auxiliary agents (wetting agents, emulsifying agents or pH buffering agents) may be present in the composition. The carrier allows the pharmaceutical composition to be formulated as tablets, pills, sugar-coated tablets, solutions, gels, syrups, slurries, or suspensions for ingestion by a test subject.

The scope of the present invention is compositions present in some forms of administration; such forms include, but are not limited to, suitable forms for parenteral administration, such as injection or transfusion (e.g., bolus or continuous transfusion). When the products are injected or infused, they may take the form of suspensions, solutions or emulsions in oily or aqueous vehicles, and may contain formulatory agents (suspending agents, stabilizing agents, and/or dispersing agents). Alternatively, it may be in dry form, for reconstitution prior to use with a suitable sterile liquid.

Once formulated, the compositions of the present invention can be administered directly to a test subject. In one embodiment, the composition is adapted for administration to a mammal (e.g., a human test subject).

The pharmaceutical compositions of the present invention disclosure can be administered by any number of routes (including but not limited to oral, intravenous, intramuscular, intraarterial, intramedullary, intraperitoneal, intrathecal, intraventricular, transdermal, transdermal, topical, subcutaneous, intranasal, enteral, sublingual, intravaginal, and rectal routes). A hypospray can also be used to administer the pharmaceutical compositions of the present disclosure. Typically, the therapeutic compositions are prepared as injectables, either as liquid solutions or suspensions. Solid forms suitable for solution in, or suspension in, liquid vehicles prior to injection can be prepared.

Direct delivery of the composition is generally accomplished by subcutaneous, intraperitoneal, intravenous, intramuscular injection, or delivered to the interstitial space of the tissue. The composition can be administered to the lesion. The administration treatment can be a single dose regimen or a multiple dose regimen. The medication provides instructions related to the frequency of administration (e.g., whether it should be delivered daily, weekly, monthly, etc.). The number and dosage may also depend on the severity of the symptoms.

The composition of the present invention can be prepared in a variety of forms. For example, the composition can be prepared as an injectable, either as a liquid solution or suspension. Solid forms suitable for solution in, or suspension in, liquid vehicles prior to injection can be prepared (lyophilized compositions (such as Synagis (trademark) and Herceptin (trademark)) for reconstitution with sterile water containing preservatives). The composition may be prepared for topical administration, for example, as an ointment, cream or powder. The compositions can be prepared for oral administration, for example, as tablets or capsules, sprays, or syrups (optionally flavored). The composition may be prepared for pulmonary administration as an inhaler, for example, using a fine powder or spray. The composition may be prepared as a suppository or pessary. The compositions may be prepared for nasal, aural, or ocular administration, for example, as drops. The composition may be in the form of a kit, designed such that a combined composition is reconstituted immediately prior to administration to a test subject. For example, lyophilized antibodies can be provided in the form of a kit with sterile water or sterile buffer.

(Prophylactic Method, Vaccine)

The present disclosure can be provided as a vaccine.

In some embodiments, the pharmaceutical compositions of the present disclosure can be vaccine compositions for administration to humans to enhance immunity. The vaccine composition may further include one or more adjuvants. Examples of adjuvants that may be included in vaccine compositions are provided in the present disclosure below. In some embodiments, vaccine compositions can include cellular vaccines. In exemplary embodiments, examples of suitable adjuvants include:

(1) oil-in-water emulsion formulations (with or without muramyl polypeptides or other specific immunostimulatory substances such as bacterial cell wall components), such as MF59 (trademark) (containing 5% squalene, 0.5% Tween 80, and 0.5% sorbitan trioleate) and SAF (containing 10% squalene, 0.4% Tween 80, 5% Pluronic (trademark) block polymer L121, and threonyl (thr−)MDP), (2) saponin adjuvant, for example, QS21, STIMULON (trademark) (CambridgeBiosciente, Workester, MA), ABISCO (registered trademark) (Isconova, Sweden), or Iscomatrux Signs) (registered trademark) (CommonwealthSerum-Laboratories, Australia), (3) complete Freund's adjuvant (CFA) and incomplete Freund's adjuvant (IFA), (4) oligonucleotides containing a CpG motif in which the cytosine is unmethylated, i.e., containing at least one CG dinucleotide (e.g., Krieg, Vaccine (2000) 19: 618-622; Krieg, CurrOpinMolTher (2001) 3:15-24; WO98/40100, WO98/55495, WO98/37919, and WO98/52581), and (5) metal salts, including aluminum salts (alum, aluminum phosphate, aluminum hydroxide, etc.); (6) saponins and oil-in-water emulsions (e.g. WO99/11241).

General Technology

Any molecular biological methods, biochemical methods, and microbiological methods used in the present specification are well known and conventionally used in the art. For example, they are described in Current Protocols in Molecular Biology (onlinelibrary.wiley.com/book/10.1002/0471142727) and Molecular Cloning: A Laboratory Manual (Fourth Edition) (www.molecularcloning.com) and the like, and relevant portions of these (which may be all of them) are incorporated herein by reference.

In the present specification, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present disclosure has been described while showing preferred embodiments to facilitate understanding. The present disclosure is described hereinafter based on Examples. The above descriptions and the following Examples are not provided to limit the present disclosure, but for the sole purpose of exemplification. Thus, the scope of the present invention is not limited to the embodiments and Examples specifically described herein and is limited only by the scope of claims.

EXAMPLE

In the present Examples, based on the Declaration of Helsinki, necessary informed consent was obtained from the test subjects and the following experiments were conducted in compliance with the ethical regulations stipulated by the university. In addition to the reagents described in Examples, those obtained from other pharmaceutical companies such as Wako Pure Chemical Industries, Sigma-Aldrich, etc. can also be used.

Example 1: Determination of Public Tfh and Epitope-1

In this Example, a single cell-based RNA sequencing platform (Chromium from 10× Genomics) was used to analyze SARS-CoV-2 specific T cell subsets and their clonotypes.

(Separation of Peripheral Blood Mononuclear Cell (PBMC) and Plasma Collection)

Peripheral blood mononuclear cells (PBMCs) were prepared from six individuals, including healthy donors and convalescent COVID-19 patients. Participant information and severity classification used are shown in Tables 1 and 2. Preparation was carried out as follows. Whole blood was collected into heparin-coated tubes and centrifuged at 1500 rpm for 10 min to separate the cellular fraction and plasma. The plasma was removed from the cell pellet and store at −80° C. Next, PBMCs separated by density gradient sedimentation and red blood cells were lysed using ACK lysis buffer. The separated PBMCs are stored frozen at −80° C. in STEM-CELLBANKER (Zenoaq Resource).

TABLE 1

Participant characteristics

| | COVID19 Patients N = 5 | Unexposed N = 1 |
|---|---|---|
| Age (years) | A-B (Median = C, IQR = D) | 31 |
| Gender | | |
| Male (%) | E % (F/G) | 100% (1/1) |
| Female (%) | | N/A |
| Nationality | | |
| Japanese (%) | | 100% (1/1) |
| Others (%) | | N/A |
| Peak Disease Severity[a] | | |
| Mild | N/A | N/A |
| Moderate I | 20% (1/5) | N/A |
| Moderate II | 20% (1/5) | N/A |
| Severe | 60% (3/5) | N/A |

[a]Japanese COVID-19 clinical practice guideline ver. 2.2

TABLE 2

COVID-19 disease severity classifications in Japan

| | Saturation of Percutaneous Oxygen ($SpO_2$) | Clinical Symptoms and Conditions |
|---|---|---|
| Mild | $SpO_2 \geq 96\%$ | No respiratory symptoms. Only cough but no dyspnea. |
| Moderate I | $93\% < SpO_2 < 96\%$ | Dyspnea or abnormal shadow on chest X-ray or computed tomography. |
| Moderate II | $SpO_2 \leq 93\%$ | Oxygenation is necessary. |
| Severe | | Intensive Care Unit level care or Mechanical ventilation is necessary. |

Cryopreserved PBMC was thawed and washed with RPMI1640 medium supplemented with 5% human AB serum. $5\times10^5$ PBMCs were stimulated with inactivated SARS-CoV-2 containing 1 μg/ml S protein, recombinant S protein (1 μg/ml), S peptide pool (1 μg/ml/peptide), or M+N peptide pool (1 μg/ml). (Inactivated SARS-CoV-2 virus was provided by Mr. Shioda and Mr. Nakayama (Research Institute of Microbial Diseases, Osaka University). Recombinant SARS-CoV-2S protein was prepared as described in Amanat F, et al. bioRxiv.2020. PepMix SARS-CoV-2 (spike glycoprotein) (including pools #1 and #2) was purchased from JPT Peptide Technologies. PepTivator SARS-CoV-2 Prot_M and _N were purchased from MiltenyiBiotec.). 20 hr at 37° C., followed by staining with anti-human CD3 (HIT3a), CD69 (FN50), CD137 (4B4-1) and TotalSeq (trademark)-C Hashtag (all purchased from BioLegend). CD3+CD69+ or CD3+CD137+ cells were sorted by cell sorter SH-800S cells (SONY) and analyzed for TCR sequences along with RNA expression by single cell VDJ-RNA-seq analysis as described below.

(Single-Cell-Based Transcriptome and TCR Repertoire Analysis)

The following reagents were used for single cell capture and library preparation. Chromium Single Cell 5'Library&Gel Bead Kit, PN-1000165; Chromium Next GEM Chip G Single Cell Kit, PN-1000120; Chromium Single Index Kit T Set A, PN-1000213; Chromium Single Cell 5'Feature Barcode Library Kit, PN-1000080; Single Index Kit N Set A, PN-1000212; Chromium single cell V(D)J concentration kit, human T cells, PN-1000005. A single cell suspension containing about $2\times10^4$ cells were loaded onto a Chromium microfluidic chip to generate single-cell gel-bead-in-emulsions using a Chromium controller (10× Genomics) according to the manufacturer's instructions. Barcoded cell-derived RNA for each sample was then reverse transcribed in the gel-bead-in-emulsion using the Veriti Thermal Cycler (Thermo Fisher Scientific), and all subsequent steps to generate single-cell libraries were performed according to the manufacturer's protocol, with 14 cycles for cDNA amplification. Approximately 50 ng of cDNA was then used for 14 cycles of gene expression library amplification in parallel with TCR library cDNA enrichment and library construction. The library fragment size was confirmed using the Agilent 2100 Bioanalyzer (Agilent). The library was sequenced on an Illumina NovaSeq6000 in paired-end mode (read1: 28 bp; read2: 91 bp). Raw reads were processed by Cell Ranger 3.1.0 (10× Genomics). Gene expression-based clustering was performed using the Seurat R package (v3.1, Hafemeister, C., Satija, R. Normalization and variance stabilization of single-cell RNA-seq data using regularized negative binomial regression. Genome Biol 20, 296 (2019). doi.org/10.1186/s13059-019-1874-1). Briefly, cells with more than 10% mitochondrial content, less than 200 detected genes, or more than 4000 genes were considered outliers (dying cells, empty droplets and doublets, respectively) and filtered out. Since the SeuratSCTransform function was used for normalization and all samples were processed simultaneously, the data were integrated without performing batch effect correction. HashTag oligo demultiplexing was performed on CLR-normalized HashTagUMI counts and clonotypes were matched to gene expression data via droplet barcodes using a Python script. Only cells assigned a single hashtag and beta chain clonotype were retained for downstream analysis.

(Bulk TCR Sequence)

1-$3\times10^5$ PBMCs were lysed with QIAzol, then full-length cDNA was synthesized using SMARTer technology (Takara Bio) and variable regions of TCRα and β genes were amplified using TRAC/TRBC specific primers. After sequencing the variable region amplicons, each pair of reads was assigned clonotype (defined as TR(A/B)V and TR(A/B)J genes and complementarity determining region (CDR) 3) using MiXCR software (Bolotin, D., Poslavsky, S., Mitrophanov, I. et al. MiXCR: software for comprehensive adaptive immunity profiling. Nat Methods 12, 380-381 (2015). doi.org/10.1038/nmeth.3364). For each alpha/beta clonotype, expansion was defined as the proportion of reads for that clone divided by the total number of reads for the alpha/beta chain, respectively, and the proportions were log 10 transformed for plotting and statistical analysis.

By UMAP plots and single-cell gene expression, it was confirmed that the circulating Tfh cluster is composed of cells expressing Tfh-related genes such as CD200, PDCD1, ICOS, CXCL13, and CD40LG (FIG. 1A). Furthermore, 120 pairs of TCRs were identified within the Tfh cluster (Table 3).

TABLE 3

| TRBV | CDR3β amino acid | TRBJ | TRAV | CDR3α amino acid | TRAJ | CLUSTER | Patient | Stimu-lation | 4-1BB. 1v1 | IFNG. 1v1 | CD69. 1v1 | Seurat.barcode |
|---|---|---|---|---|---|---|---|---|---|---|---|---|
| TRBV20-1 | CSASPGLNTDTQYF | TRBJ2-3 | TRAV8-3 | CAVLTGGYNKLIF | TRAJ4 | 47605 | HC | recomb-inant S protein | Low/Nega | Low/Nega | Low/Nega | DB1_TGGTTAGAGCGCCTTG |
| TRBV20-1 | CSASGTGEVGELFF | TRBJ2-2 | TRAV4 | CLVARGGYQKVTE | TRAJ13 | 48063 | HC | Peptide pool M + N | Low/Nega | Low/Nega | High | DB1_AACTGCCGTCCTGCTT |
| TRBV30 | CAWKQGWTEAFF | TRBJ1-1 | TRAV8-4 | CAVSDLYGNNRLAF | TRAJ7 | 25270 | HC | Peptide pool S | Low/Nega | Low/Nega | Low/Nega | DB1_AGCGTCGTCAGCTCTC |
| TRBV7-7 | CASSTSGNTGELFF | TRBJ2-2 | TRAV8-4 | CAVSDSGAGSYQLTF | TRAJ28 | 35098 | HC | in-activated virus | High | Medium | Medium | DB1_ATGTGTGAGGAGTACC |
| TRBV7-6 | CASSLTGLPIYNEQFF | TRBJ2-1 | TRAV25 | CAGLGAGNMLTF | TRAJ39 | 22074 | HC | recomb-inant S protein | Low/Nega | Low/Nega | Low/Nega | DB1_TTGCCGTCATGTCCTC |
| TRBV20-1 | CSATDRANYGYTF | TRBJ1-2 | TRAV35 | CAASGINAGKSTF | TRAJ27 | 47996 | HC | Peptide pool M + N | Low/Nega | Low/Nega | Low/Nega | DB1_TGTTCGGGTGCTCCAT |
| TRBV27 | CASSSPGQGAYNEQFF | TRBJ2-1 | TRAV2 | CAVGPPGFNKFYF | TRAJ21 | 22783 | HC | Peptide pool M + N | Low/Nega | Low/Nega | Low/Nega | DB1_CATCGAACACGGTAGA |
| TRBV6-5 | CASRTVNTEAFF | TRBJ1-1 | TRAV25 | CAISGNARLMF | TRAJ31 | 27505 | HC | recomb-inant S protein | Low/Nega | Low/Nega | Medium | DB1_CGAATCCAGTGGTAGC |
| TRBV18 | CASSLGQVYEQY:F | TRBJ2-7 | TRAV26-2 | CILRESKAGNMLTF | TRAJ39 | 45929 | HC | Peptide pool S | Low/Nega | Low/Nega | Low/Nega | DB1_CCAGCGATCTATCCCG |
| TRBV2 | CATEAGETQYF | TRBJ2-5 | TRAV1-2 | CAVRALTGGGNKLTF | TRAJ10 | 28997 | HC | Peptide pool S | Medium | Low/Nega | Low/Nega | DB1_TGCGCAGGTTGCTCCT |
| TRBV5-1 | CASSLVSDYEQYF | TRBJ2:7 | TRAV17 | CATDEGDYKLSF | TRAJ20 | 43708 | HC | Peptide pool M + N | Low/Nega | High | Low/Nega | DB1_CTCCTAGCACTCCCAG |
| TRBV6-5 | CASSQTTGVVEQYF | TRBJ2-7 | TRAV8- | CAVSDRIKAAGNKLTF | TRAJ17 | 37974 | HC | recomb-inant S protein | Low/Nega | Low/Nega | Low/Nega | DB1_GCTTCCATCGTAGGAG |
| TRBV20-1 | CSARAFEGELFF | TRBJ1-4 | TRAV12-2 | CAVRRTDYKLSF | TRAJ20 | 26900 | HC | Peptide pool M + N | Medium | Low/Nega | Low/Nega | DB1_TCGGGACCACTTACGA |

TABLE 3-continued

| TRBV | CDR3β amino acid | TRBJ | TRAV | CDR3α amino acid | TRAJ | CLUSTER | Patient | Stimulation | 4-1BB.1v1 | IFNG.1v1 | CD69.1v1 | Seurat.barcode |
|---|---|---|---|---|---|---|---|---|---|---|---|---|
| TRBV9 | CASSVWGSGGNEQFF | TRBJ2-1 | TRAV17 | CATEGSGYSTLTF | TRAJ11 | 11503 | patient #1 | Peptide pool S | Low/Nega | Low/Nega | High | DB1_TGAGAGGTCCGCATCT |
| TRBV12-4 | CASSLGLQGNQPQHF | TRBJ1-5 | TRAV17 | CASRASGSRLTF | TRAJ58 | 20367 | patient #1 | Peptide pool S | High | Low/Nega | Low/Nega | DB1_AACGTTGCACAAGACG |
| TRBV20-1 | CSAKTSGRGETQYF | TRBJ2-5 | TRAV13-2 | CAENSGGSNYKLTF | TRAJ53 | 47690 | patient #1 | Peptide pool S | High | Low/Nega | Low/Nega | DB1_GGGTCGACACCTATCC |
| TRBV6-5 | CASSSISGLNQPQHF | TRBJ1-5 | TRAV 12-3 | CAMSAGSGTYKYIF | TRAJ40 | 20204 | patient #1 | Peptide pool S | Medium | Low/Nega | Low/Nega | DB1_CGCGTTTGTAAACCTC |
| TRBV19 | CASSIRSSYEQYF | TRBJ2-7 | TRAV27 | CAGVGGGSQGNLIF | TRAJ42 | 46110 | patient #1 | Peptide pool M + N | Low/Nega | High | Low/Nega | DB1_CACATTTGTAGCTCCG |
| TRBV2 | CASSPGQGNSPLHF | TRBJ1-6 | TRAV8-4 | CAVSAASARQLTF | TRAJ22 | 30803 | patient #1 | Peptide pool S | Low/Nega | Low/Nega | Low/Nega | DB1_ATTGGACGTAGCGCAA |
| TRBV11-2 | CASSWDGDNSPLHF | TRBJ1-6 | TRAV3 | CAVRDKTGRRALTF | TRJ5A | 30866 | patient #1 | Peptide pool S | High | Low/Nega | Low/Nega | DB1_TAAGAGAGTGTAATGA |
| TRBV7-7 | CASSLRYGGELFF | TRBJ2-2 | TRAV36/DV7 | CAVDSGTYKYIF | TRAJ40 | 40982 | patient #2 | recombinant S protein | Medium | Low/Nega | Low/Nega | DB2_GTAGGCCCAATGGTCT |
| TRBV3-1 | CASSHDRAEQYF | TRBJ2-7 | TRAV30 | CGTEIGTDKLIF | TRAJ34 | 26138 | patient #2 | inactivated virus | Low/Nega | Low/Nega | Low/Nega | DB2_CACTCCAGTATAGGGC |
| TRBV9 | CASSERTSGNGEQFF | TRBJ2-1 | TRAV12-2 | CAVSPPGGSYIPTF | TRAJ6 | 11505 | patient #2 | recombinant S protein | Low/Nega | Low/Nega | Low/Nega | DB2_GATCTAGCATTCCTGC |
| TRBV3-1 | CASSPRAGAGGELFF | TRBJ2-2 | TRAV38-1 | CAFMKYNNNDMRF | TRAJ43 | 14496 | patient #2 | Peptide pool M + N | Low/Nega | High | Low/Nega | DB2_AGCTCTCGTTGACGTT |
| TRBV24-1 | CATSRTGGGTAEQYE | TRBJ2-7 | TRAV5 | CAERGAAGNKLTF | TRAJ17 | 8497 | patient #2 | recombinant S protein | Low/Nega | Low/Nega | Low/Nega | DB2_CGTGTCTTCTTGTACT |
| TRBV5-4 | CASSLGAGGPYNEQFF | TRBJ2-1 | TRAV9-2 | CALTLTGNQFYF | TRAJ49 | 22442 | patient #2 | recombinant S protein | Medium | Low/Nega | High | DB2_ACCGTAATCGCTAGCG |
| TRBV20-1 | CSASRGAGWMETQYE | TRBJ2-5 | TRAV12-1 | CVVNRGSNYKLTF | TRAJ53 | 48660 | patient #2 | inactivated virus | Low/Nega | Medium | Medium | DB2_CTAATGGTCGCGTAGC |

TABLE 3-continued

| TRBV | CDR3β amino acid | TRBJ | TRAV | CDR3α amino acid | TRAJ | CLUSTER | Patient | Stimu-lation | 4-1BB. 1v1 | IFNG. 1v1 | CD69. 1v1 | Seurat.barcode |
|---|---|---|---|---|---|---|---|---|---|---|---|---|
| TRBV28 | CASSLSPPRQGSESPLHF | TRBJ1-6 | TRAV14/DV4 | CAMREGRTGGFKTIF | TRAJ9 | 7178 | patient #2 | Peptide pool S | Low/Nega | Low Nega | Low/Nega | DB2_GAAGCAGCAAGCGCTC |
| TRBV5-1 | CASSSSSVSYEQYF | TRBJ2-7 | TRAV38-1 | CAFVSTGANSKLTF | TRAJ56 | 36273 | patient #2 | in-activated virus | Low/Nega | High | Low Nega | DB2_GACGTGCTCAGCTGGC |
| TRBV19 | CASSIAGAGKQFF | TRBJ2-1 | TRAV12-2 | CAFEHGSSNTGKLIF | TRAJ37 | 45762 | patient #3 | Peptide pool M + N | High | Low/Nega | Low/Nega | DB2_GAGCAGAAGGCATTGG |
| TRBV11-2 | CASSRTYEQYF | TRBJ2-7 | TRAV12-1 | CVVNMNYGGSQGNLIF | TRAJ42 | 29298 | patient #3 | Peptide pool S | Medium | Low/Nega | Medium | DB2_GAGCAGACATGCATGT |
| TRBV5-1 | CASSSSVQMNTEAFF | TRBJ1-1 | | | | 14219 | patient #3 | recomb-inant S protein | High | Low/Nega | Low/Nega | DB2_GCATACAGTGTGAATA |
| TRBV27 | CASSSVTGVSLREQFF | TRBJ2-1 | TRAV22 | CAVEGSGTYKYIF | TRAJ40 | 21747 | patient #3 | in-activated virus | Low/Nega | Low/Nega | Low/Nega | DB2_GCCAAATAGTTGTCGT |
| TRBV6-6 | CASNNRAGNTIYF | TRBJ1-3 | TRAV21 | CAVNQRSYDKVIF | TRAJ50 | 39348 | patient #3 | in-activated virus | Medium | High | Low/Nega | DB2_GCGACCATCAAACCGT |
| TRBV5-1 | CASSLPGAWNTEAFF | TRBJ1-1 | TRAV3 | CAVRDPSGSARQLTF | TRAJ22 | 14278 | patient #3 | recomb-inant S protein | Low/Nega | Low/Nega | Low/Nega | DB2_GCTTGAATCCCGACTT |
| TRBV5-6 | CASSQAYEQYF | TRBJ2-7 | TRAV23/DV6 | CAASYGGATNKLIF | TRAJ32 | 29063 | patient #3 | in-activated virus | Low/Nega | High | Medium | DB2_TGTATTCAGGTGACCA |
| TRBV9 | CASSVGVGSDTQYF | TRBJ2-8 | TRAV36/DV7 | CAVAVQGAQKLVF | TRAJ54 | 36451 | patient #3 | Peptide pool S | Medium | Medium | Low/Nega | DB2_GGCTGGTAGTATGACA |
| TRBV10-3 | CAISESGVNLGGNQPQHF | TRBJ1-5 | TRAV12-2 | CAVRAVGDKIIF | TRAJ30 | 1470 | patient #3 | recomb-inant S protein | Low/Nega | Low/Nega | Low/Nega | DB2_GGTGAAGGTTAAGAAC |
| TRBV12-5 | CASGLVASPGAGELFF | TRBJ2-2 | TRAV35 | CAGGVTGTASKLTF | TRAJ44 | 8006 | patient #3 | recomb-inant S protein | High | Low/Nega | Low/Nega | DB2_GTCATTTGTCTGCCAG |
| TRBV30 | CAWSVLSGRPFGGGANVLTF | TRBJ2-6 | TRAV12-2 | CAVKKSWASYDKVIF | TRAJ50 | 1261 | patient #3 | in-activated virus | Medium | Low/Nega | Medium | DB2_GTGCAGCCAGTCTTCC |

TABLE 3-continued

| TRBV | CDR3β amino acid | TRBJ | TRAV | CDR3α amino acid | TRAJ | CLUSTER | Patient | Stimu-lation | 4-1BB. 1v1 | IFNG. 1v1 | CD69. 1v1 | Seurat.barcode |
|---|---|---|---|---|---|---|---|---|---|---|---|---|
| TRBV24-1 | CATSDLSGNQPQHF | TRBJ1-6 | | | | 30566 | patient #3 | in-activated virus | Low/Nega | Low/Nega | Low/Nega | DB2_GTTAAGCGTGAACCTT |
| TRBV18 | CASSPDSTDTQYF | TRBJ2-3 | TRAV23/DV6 | CAASKYNTDKLIF | TRAJ34 | 45926 | patient #3 | in-activated virus | Low/Nega | High | Medium | DB2_TCATTAGAGAAGGTTT |
| TRBV25-1 | CASSESGDNYGYTF | TRBJ1-2 | TRAV21 | CALKGSDYKLSF | TRAJ20 | 40481 | patient #3 | Peptide pool S | Medium | High | Low/Nega | DB2 TGAGCCGGTAGAGCTG |
| TRBV5-1 | CASSLTGVRDGEQFF | TRBJ2-1 | TRAV25 | CAGPLGSNFGNEKLTF | TRAJ48 | 10652 | patient #3 | in-activated virus | Low/Nega | Low/Nega | Low/Nega | DB2_CTGTTTACAAGTCTAC |
| TRBV7-6 | CASSSITEGGYTF | TRBJ1-2 | | | | 31840 | patient #3 | recomb-inant S protein | Low/Nega | Low/Nega | Low/Nega | DB2_TTAACTCCAAGTTCTG |
| TRBV7-8 | CASSLGGVRADTQYF | TRBJ2-3 | TRAV9-2 | CASDPSAGNNRKLIW | TRAJ38 | 18009 | patient #3 | recomb-inant S protein | Low/Nega | Low/Nega | High | DB2_TTCTTAGAGTTCGCAT |
| TRBV15 | CATSQDRVGSPLHF | TRBJ1-6 | TRAV9-2 | CALSGSGSARQLTF | TRAJ22 | 30315 | patient #3 | recomb-inant S protein | High | Low/Nega | Low Nega | DB2_TTTGGTTCATCGGTTA |
| TRBV5-1 | CASSLPGAWNTEAFF | TRBJ1-1 | TRAV3 | CAVRDPSGSARQLTF | TRAJ22 | 14278 | patient #3 | recomb-inant S protein | Low/Nega | Low/Nega | Low/Nega | DB2_GGAATAATCAGCGATT |
| TRBV11-3 | CASSLVQVGRRYNEQFF | TRBJ2-1 | | | | 5459 | patient #3 | in-activated virus | Low/Nega | Low/Nega | High | DB2_CTGAAACCATGTCGAT |
| TRBV20-1 | CSASLARGQGNSPLHF | TRBJ1-6 | TRAV12 | CVVNYNFNKFYF | TRAJ21 | 48327 | patient #3 | in-activated virus | Low/Nega | Low/Nega | Low/Nega | DB2_GCTCTGTAGGTTACCT |
| TRBV7-3 | CASSRAGGTVDTQYF | TRBJ2-3 | TRAV2 | CAANNAGNMLTF | TRAJ39 | 17392 | patient #3 | Peptide pool S | Low/Nega | High | Low/Nega | DB2_CTCGTACTCGCTTAGA |
| TRBV7-8 | CASSSDRGPGTGELFF | TRBJ2-2 | TRAV12 | CAMKRGGSQGNLIF | TRAJ42 | 23585 | patient #3 | in-activated virus | Low Nega | Low/Nega | Medium | DB2_GTCTACGGATGCATGT |
| TRBV12-3 | CASSIWDILAKNIQYF | TRBJ2-4 | TRAV29/IDV5 | CAAPGYQKVTF | TRAJ13 | 22111 | patient #3 | Peptide pool M + N | Low/Nega | Medium | Low/Nega | DB2_AAAGTAGGAATAACGA |

TABLE 3-continued

| TRBV | CDR3β amino acid | TRBJ | TRAV | CDR3α amino acid | TRAJ | CLUSTER | Patient | Stimu-lation | 4-1BB. 1v1 | IFNG. 1v1 | CD69. 1v1 | Seurat.barcode |
|---|---|---|---|---|---|---|---|---|---|---|---|---|
| TRBV18 | CASSPPGLMNTEAFF | TRBJ1-1 | TRAV8-1 | CAVNAGGNNRLAF | TRAJ7 | 39092 | patient #3 | Peptide pool S | Low/Nega | Low/Nega | Low/Nega | DB2_AAAGTAGGTACGAAAT |
| TRBV12-5 | CASGLFRTGSLEKLFF | TRBJ1-4 | TRAV6 | CALGSNARLMF | TRAJ31 | 14643 | patient #3 | Peptide pool M + N | Low/Nega | Low/Nega | Low/Nega | DB2_ACGGAGAGTAATCACC |
| TRBV18 | CASSPGQGDTQYF | TRBJ2-3 | TRAV13-1 | CASLRSNNARLMF | TRAJ31 | 46925 | patient #3 | recomb-inant S protein | Medium | Low/Nega | Low/Nega | DB2_ATAAGAGGTGTCCTCT |
| TRBV5-6 | CASSPLGRSYGYTF | TRBJ1-2 | TRAV5 | CAESLLDGQKLLF | TRAJ16 | 40230 | patient #3 | Peptide pool S | Low/Nega | Low/Nega | High | DB2_ATTGGACTGGCCATAA |
| TRBV15 | CATSRDPGIQETQYF | TRBJ2-5 | TRAV3 | CAVSALYNTDKLIF | TRAJ34 | 9815 | patient #3 | in-activated virus | Low/Nega | Low/Nega | Low/Nega | DB2_CAACCAAGTATGAAAC |
| TRBV5-1 | CASSRMTGSTDTQYF | TRBJ2-3 | TRAV12-1 | CVVNPHARLMF | TRAJ31 | 16197 | patient #3 | Peptide pool S | High | High | Low/Nega | DB2_CAAGAAAGTGCGGTAA |
| TRBV20-1 | CSADRGLAGSTDTQYF | TRBJ2-3 | TRAV9-2 | CALIPNNARLMF | TRAJ31 | 47295 | patient #3 | in-activated virus | High | High | Low/Nega | DB2_CACACTCGTGAGGGTT |
| TRBV5-1 | CASNLQGAGDTEAFF | TRBJ1-1 | TRAV13-1 | CAASKQGTGEQKLVF | TRAJ8 | 14285 | patient #3 | in-activated virus | Low/Nega | Low/Nega | Low/Nega | DB2_CAGATCATCTGACCTC |
| TRBV11-2 | CASSQTYEQYF | TRBJ2-7 | TRAV12-1 | CVVNRGSSYKLIF | TRAJ12 | 29298 | patient #3 | recomb-inant S protein | Low/Nega | Medium | Low/Nega | DB2_GAGGTGCTCTCCGGTT |
| TRBV11-3 | CASSLIRGYEQYF | TRBJ2-7 | TRAV38-1 | CAFMKHVDSGAGSYQLTF | TRAJ28 | 31105 | patient #3 | Peptide pool M + N | Low/Nega | Medium | Low/Nega | DB2_ACGCCGATCTCGTATT |
| TRBV11-2 | CASSLRGRNIQYF | TRBJ2-4 | TRAV26-1 | CIVKKLTGGGNKLTF | TRAJ10 | 44828 | patient #3 | in-activated virus | Low/Nega | Low/Nega | Low/Nega | DB2_CATTCGCAGTCATCCA |
| TRBV6-2 | CASSSTSGSTYPTEQFF | TRBJ2-1 | TRAV13-1 | CAASISNTGNQFYF | TRAJ49 | 2571 | patient #3 | in-activated virus | Low/Nega | Medium | High | DB2_CATTCGCAGTACGCCC |
| TRBV11-2 | CASSLDPVSETQY | TRBJ2-5 | TRAV26-1 | GIVKKLTGGGNKLTF | TRAJ10 | 38007 | patient #3 | in-activated virus | Low/Nega | Low/Nega | Low/Nega | DB2_CGTTCTGTCATCTGTT |

TABLE 3-continued

| TRBV | CDR3β amino acid | TRBJ | TRAV | CDR3α amino acid | TRAJ | CLUSTER | Patient | Stimu-lation | 4-1BB. 1v1 | IFNG. 1v1 | CD69. 1v1 | Seurat.barcode |
|---|---|---|---|---|---|---|---|---|---|---|---|---|
| TRBV7-9 | CASSLGDSGNTIYF | TRBJ1-3 | TRAV8-4 | CAVINSGGYQKVTF | TRAJ13 | 36754 | patient #3 | Peptide pool M + N | Medium | Low/Nega | Low/Nega | DB2_CTCGTACCAGGGTAGA |
| TRBV28 | CASSLAEGGHGNTIYF | TRBJ1-3 | TRAV8-4 | CAVRAGTASKLTF | TRAJ44 | 50955 | patient #3 | in-activated virus | Low/Nega | Low/Nega | Low/Nega | DB2_CGGAGTCTCGGCGGTT |
| TRBV6-1 | CASSVYYGYTF | TRBJ1-2 | TRAV29/DV5 | CAASRLGTASKLTF | TRAJ44 | 26565 | patient #3 | in-activated virus | Medium | Low/Nega | Low/Nega | DB2_CGGAGTCCAGCCAGAA |
| TRBV7-9 | CASSLVGEQYF | TRBJ2-7 | | | | 29162 | patient #3 | recomb-inant S protein | Low/Nega | Low/Nega | Low/Nega | DB2_CGTCTACAGAGTACCG |
| TRBV18 | CASSRSLGLMNTEAFF | TRBJ1-1 | | | | 15086 | patient #3 | in-activated virus | Low/Nega | Low/Nega | Low/Nega | DB2_CCCTCCTAGAGGAATT |
| TRBV4-2 | CASSQADRGESPLHF | TRBJ1-6 | TRAV8-4 | CAVSDRGSARQLTF | TRAJ22 | 19609 | patient #3 | in-activated virus | Low/Nega | Low/Nega | Low/Nega | DB2_CCAGGGAAGCTAACTC |
| TRBV14 | CASSRTSGWTDTQYF | TRBJ2-3 | TRAV8-3 | GAVGARTGRRALTF | TRAJ5 | 8189 | patient #3 | in-activated virus | Low/Nega | Low/Nega | Low/Nega | DB2_CGAATCCGTTCACGGC |
| TRBV28 | CASSTMSGVETQYF | TRBJ2-5 | TRAV19 | CALSANTGRRALTF | TRAJ5 | 37164 | patient #3 | Peptide pool S | Medium | Low/Nega | Low/Nega | DB2_CGCGAAGCATATACGC |
| TRBV5-4 | CASRAAGTGAWGYTF | TRBJ1-2 | TRAV38-1 | CAFMKYNNNDMRF | TRAJ43 | 20875 | patient #3 | in-activated virus | Low/Nega | Low/Nega | Low/Nega | DB3_GCTTGAAAGGCTAGCA |
| TRBV5-5 | CASSRGLAGIPTGELFF | TRBJ2-2 | TRAV29/DV5 | CAASPMNRDDKIIF | TRAJ30 | 5395 | patient #4 | Peptide pool M + N | High | Medium | Low/Nega | DB3_GCACATACATAGGATA |
| TRBV20-1 | CSARLLGQGASYEQYF | TRBJ2-7 | TRAV8-3 | CQKLLF | TRAJ16 | 47226 | patient #4 | Peptide pool M + N | Medium | Medium | Low/Nega | DB3_GGAGCAACAAACGTGG |
| TRBV6-1 | CASSEFGTGEQFF | TRBJ2-1 | TRAV26-1 | CIVRVKGGGSNYKLTF | TRAJ53 | 42080 | patient #4 | in-activated virus | Low/Nega | Low/Nega | Low/Nega | DB3_GGCCGATCAGATCGAA |

TABLE 3-continued

| TRBV | CDR3β amino acid | TRBJ | TRAV | CDR3α amino acid | TRAJ | CLUSTER | Patient | Stimu-lation | 4-1BB. 1v1 | IFNG. 1v1 | CD69. 1v1 | Seurat.barcode |
|---|---|---|---|---|---|---|---|---|---|---|---|---|
| TRBV6-2 | CASTRGVTDTQYF | TRBJ2-3 | TRAV36/DV7 | CADLTQGGSEKLVF | TRAJ57 | 45445 | patient #4 | Peptide pool M + N | Low/Nega | Low/Nega | High | DB3_GGCTGGTGTAGTGAAT |
| TRBV2 | CASSPHDYEQFF | TRBJ2-1 | TRAV22 | CAVKGLGSTGNQFYF | TRAJ49 | 27381 | patient #4 | Peptide pool M + N | Low/Nega | Low/Nega | Medium | DB3_GGGTTGCTCCGTAGAA |
| TRBV20-1 | CSALPAGGRNEQYF | TRBJ2-7 | TRAV36/DV7 | CAVASQGGSEKLVF | TRAJ57 | 47821 | patient #4 | in-activated virus | Low/Nega | Low Nega | High | DB3_GTAGGCCAGATTGTTAG |
| TRBV11-2 | CASSPTYEQYF | TRBJ2-7 | TRAV12-1 | CVVNRGSSYKLIF | TRAJ12 | 29298 | patient #4 | Peptide pool S | Low/Nega | High | Low/Nega | DB3_GTCACAAGTGAAAGAG |
| TRBV7-2 | CASSLDGARSYNEQFF | TRBJ2-1 | TRAV21 | CAVGSNYQLIW | TRAJ33 | 23764 | patient #4 | recomb-inant S protein | Low/Nega | Low/Nega | Medium | DB3_TAGTGGTCAGCGATCC |
| TRBV5-1 | CASAVGGLTNEKLFF | TRBJ1-4 | TRAV20 | CAVGFQGGSEKLVF | TRAJ57 | 10942 | patient #4 | recomb-inant S protein | Low/Nega | Low/Nega | Low/Nega | DB3_TACGGTAAGGAGCGAG |
| TRBV10-3 | CAITRDTDGYTF | TRBJ1-2 | TRAV12-1 | CVVNNARLMF | TRAJ31 | 41543 | patient #4 | in-activated virus | Low/Nega | Low/Nega | Low/Nega | DB3_TACTTGTGTAGTACCT |
| TRBV12-3 | CASSLVTGSTEAFF | TRBJ1-1 | TRAV12-3 | CAMSRPGAGSYQLTF | TRAJ28 | 34575 | patient #4 | recomb-inant S protein | High | Low/Nega | Low/Nega | DB3_TAGCCGGCATGGGACA |
| TRBV7-8 | CASSLAGGSTDTQYF | TRBJ2-3 | TRAV2 | CASHNAGNMLTF | TRAJ39 | 17390 | patient #4 | Peptide pool S | Low/Nega | Low/Nega | Low/Nega | DB3_TCAGGTAGTGGCAAAC |
| TRBV7-2 | CASSPMGDSADTQYF | TRBJ2-3 | TRAV8-1 | CAVNAGRRALTF | TRAJ5 | 17435 | patient #4 | Peptide pool S | Low/Nega | Low/Nega | Medium | DB3_TCCAGACGTGATGGCC |
| TRBV2 5-1 | CASSPGSGHNEQFF | TRBJ2-1 | TRAV9-2 | CALSGGWDSGYSTLTF | TRAJ11 | 84790 | patient #4 | recomb-inant S protein | Low/Nega | High | Low/Nega | DB3_TGACGGCCAAGTACCT |
| TRBV11-2 | CASSLGIDEQFF | TRBJ2-1 | TRAV23/DV6 | CAAKGGSQGNLIF | TRAJ42 | 27964 | patient #4 | Peptide pool M + N | Medium | High | Low/Nega | DB3_TGGACGTAGGAATATG |
| TRBV4-3 | CASSQERVSGYEQYF | TRBJ2-7 | TRAV13 | CAASISGSARQLTF | TRAJ22 | 16803 | patient #4 | Peptide pool S | Medium | Low/Nega | Low/Nega | DB3_GCACATACAGACGCAA |

TABLE 3-continued

| TRBV | CDR3β amino acid | TRBJ | TRAV | CDR3α amino acid | TRAJ | CLUSTER | Patient | Stimu-lation | 4-1BB.1v1 | IFNG.1v1 | CD69.1v1 | Seurat.barcode |
|---|---|---|---|---|---|---|---|---|---|---|---|---|
| TRBV20-1 | CSARDIGGGTSPLHF | TRBJ1-6 | TRAV23/DV6 | CAATSATSGTYKYIF | TRAJ40 | 19940 | patient #4 | Peptide pool S | Medium | Low/Nega | Low/Nega | DB3_TTCTACAAGTAGATGT |
| TRBV11-2 | CASSPTYEQYF | TRBJ2-7 | TRAV12-1 | CVVNRGSSYKLIF | TRAJ12 | 29298 | patient #4 | Peptide pool S | Low/Nega | High | Low/Nega | DB3_TACAGTGCAGGAATCG |
| TRBV5-1 | CASSAMVGQETQYF | TRBJ2-5 | TRAV18-1 | CALGDSGYALNF | TRAJ41 | 35856 | patient #4 | in-activated virus | Low/Nega | Low/Nega | Low/Nega | DB3_GAGTCCGCAGACGCAA |
| TRBV2 | CASRKADRRQGLIRSYEQYF | TRBJ2-7 | TRAV1-2 | CARGKPGANNLFF | TRAJ36 | 1220 | patient #4 | Peptide pool S | Low/Nega | Low/Nega | High | DB3_CGATTGAAGGATATAC |
| TRBV6-5 | CASRPEKRSGNTIYF | TRBJ1-3 | TRAV9-2 | CALSPSILYYGQNFVF | TRAJ26 | 15305 | patient #4 | Peptide pool S | Medium | High | Medium | DB3_GAAGCAGCACCAGCAG |
| TRBV11-3 | CASSLGGQETQYF | TRBJ2-5 | TRAV9-2 | CAPHTGGTSYGKLTF | TRAJ52 | 31107 | patient #4 | Peptide pool S | Low/Nega | Low/Nega | High | DB3_TTTGGTTGTTCGCGAC |
| TRBV2 | CASSAHRGDEKLFF | TRBJ1-4 | TRAV12-1 | CVVNNPNAGNMLTF | TRAJ39 | 32292 | patient #4 | recomb-inant S protein | Low/Nega | Low/Nega | Low/Nega | DB3_ACGAGGAGTAGCGTGA |
| TRBV4-3 | CASSQERVSGYEQYF | TRBJ2-7 | TRAV13-1 | CAASISGSARQLTF | TRAJ22 | 16803 | patient #4 | Peptide pool S | High | Low/Nega | Low/Nega | DB3_AGCATACAGTTAACGA |
| TRBV4-3 | CASSQDIGESPLHF | TRBJ1-6 | TRAV8-3 | CAVTSGTYKYIF | TRAJ40 | 30270 | patient #4 | in-activated virus | Low/Nega | High | Low/Nega | DB3_AGTGTCACAGCTTAAC |
| TRBV11-2 | CASSSSPGTSGTGTGELFF | TRBJ2-2 | TRAV8-3 | CAVGARWTGNQFYF | TRAJ49 | 781 | patient #4 | Peptide pool S | Medium | High | Low/Nega | DB3_CAACTAGCATTCCTCG |
| TRBV4-2 | CASSAQGEGTEAFF | TRBJ1-1 | TRAV17 | CATGSGYSTLTF | TRAJ11 | 32454 | patient#4 | recomb-inant S protein | Low/Nega | High | Low/Nega | DB3_CATGGCGAGCAGCGTA |
| TRBV20-1 | CSARSPRGGAYEQYF | TRBJ2-7 | | | | 48449 | patient #4 | Peptide pool S | Low/Nega | Low/Nega | High | DB3_CGATGGCTCAGCGATT |
| TRBV5-4 | CASSFGGPTSYEQYF | TRBJ2-7 | TRAV12-1 | CVVEDTGRRALTF | TRAJ5 | 15992 | patient #4 | in-activated virus | Low/Nega | Low/Nega | High | DB3_CGCCAAGAGCCAGTTT |
| TRBV6-1 | CASTPDKEYNQPQHF | TRBJ1-5 | TRAV10 | CVVSANTGGFKTIF | TRAJ9 | 19544 | patient #4 | Peptide pool M + N | Low/Nega | Low/Nega | High | DB3_CCTCAGTGTTCAGTAC |

TABLE 3-continued

| TRBV | CDR3β amino acid | TRBJ | TRAV | CDR3α amino acid | TRAJ | CLUSTER | Patient | Stimu-lation | 4-1BB. 1v1 | IFNG. 1v1 | CD69. 1v1 | Seurat.barcode |
|---|---|---|---|---|---|---|---|---|---|---|---|---|
| TRBV19 | CASSMRAGEGGE TQYF | TRBJ2-5 | | | | 51817 | patient #4 | in-activated virus | Low/Nega | Low/Nega | Low/Nega | DB3_CGCGTTTTCT GGAGCC |
| TRBV2 | CASRPQGNGGYT F | TRBJ1-2 | | | | 31602 | patient #4 | Peptide pool S | High | Low/Nega | Low/Nega | DB3_CGGAGCTAGA TCCCAT |
| TRBV12-4 | CASRPRDRSNSPL HF | TRBJ1-6 | TRAV9-2 | CALSQNTGGFK TIF | TRAJ9 | 20424 | patient #4 | in-activated virus | Low/Nega | Low/Nega | High | DB3_CGTAGCGGTT TGGCGC |
| TRBV30 | CAWSPLGSGDEK LFF | TRBJ1-4 | TRAV9-2 | CALSGQAGTALI F | TRAJ15 | 24920 | patient #4 | Peptide pool S | Medium | Low/Nega | Low/Nega | DB3_CGTCCATTCG TACGGC |
| TRBV5-1 | CASSLRQGGTGE LFF | TRBJ2-2 | | | | 13710 | patient #4 | recomb-inant S protein | Low/Nega | Low/Nega | Low/Nega | DB3_CTACACCTCG TTTAGG |
| TRBV11-2 | CASSLGTEETQYF | TRBJ2-5 | TRAV30 | CGTERTGGTSY GKLTF | TRAJ52 | 44725 | patient #4 | Peptide pool M + N | High | High | Low/Nega | DB3_CTACGTCCAT CTCCCA |
| TRBV6-5 | CASSYSGQGRSPL HF | TRBJ1-6 | TRAV1-2 | CAVKMDSSYKLI F | TRAJ12 | 20677 | patient #4 | Peptide pool M + N | Medium | Low/Nega | Low/Nega | DB3_TTTGTCACAT GCCTTC |

TABLE 3-continued

| TRBV | CDR3β amino acid | TRBJ | TRAV | CDR3α amino acid | TRAJ | CLUSTER | Patient | Stimu-lation | 4-1BB. 1v1 | IFNG. 1v1 | CD69. 1v1 | Seurat.barcode |
|---|---|---|---|---|---|---|---|---|---|---|---|---|
| TRBV28 | CASSSGQKLAKNIQYF | TRBJ2-4 | TRAV27 | CAGPRGSNYKLTF | TRAJ53 | 21951 | patient #5 | Peptide pool S | Low/Nega | Low/Nega | Low/Nega | DB3_GAGCAGAGTACTTAGC |
| TRBV4-1 | CASSPGGQGRYQPQHF | TRBJ1-5 | TRAV9-2 | CALSTNAGKSTF | TRAJ27 | 50390 | patient #5 | recomb-inant S protein | Low/Nega | Low/Nega | Low/Nega | DB3_CAGCGACGTTATTCTC |
| TRBV7-3 | CASSSTGGQETQYF | TRBJ2-5 | TRAV18-1 | CAAFQGAQKLVF | TRAJ54 | 38135 | patient #5 | in-activated virus | Low/Nega | High | Low/Nega | DB3_AGTCTTTCACCGAAAG |
| TRBV19 | CASSSPGRQVEAFF | TRBJ1-1 | TRAV8-3 | CARIGYSTLTF | TRAJ11 | 34375 | patient #5 | in-activated virus | Medium | High | Low/Nega | DB3_GCAGCCATCATGTCCC |
| TRBV3-1 | CASSPTLGGASYEQYF | TRBJ2-7 | TRAV29/DV5 | CAARATYSGAGSYQLTF | TRAJ28 | 51305 | patient #5 | Peptide pool M + N | High | Low/Nega | Low/Nega | DB3_ACTGCTCGTCTGCACT |
| TRBV11-3 | CASSLHPGQGYEEQYF | TRBJ2-7 | TRAV13-1 | CAASRAGTALIF | TRAJ15 | 31056 | patient #5 | in-activated virus | Low/Nega | Low/Nega | Low/Nega | DB3_TGCCCTAAGAGTAATC |
| TRBV6-1 | CASTTDSAARPQHF | TRBJ1-5 | TRAV12-1 | CVVNMRSSNTGKLIF | TRAJ37 | 38619 | patient #5 | recomb-inant S protein | Low/Nega | Medium | Low/Nega | DB3_CTGCGGATCTATCCTA |
| TRBV5-4 | CASSRTSLADPNEQFF | TRBJ2-1 | TRAV5 | CAAEADAGNMLTF | TRAJ39 | 22454 | patient #5 | Peptide pool S | Low/Nega | Low/Nega | Low/Nega | DB3_GGTGAAGGAAGAGGCT |

Figure 2:
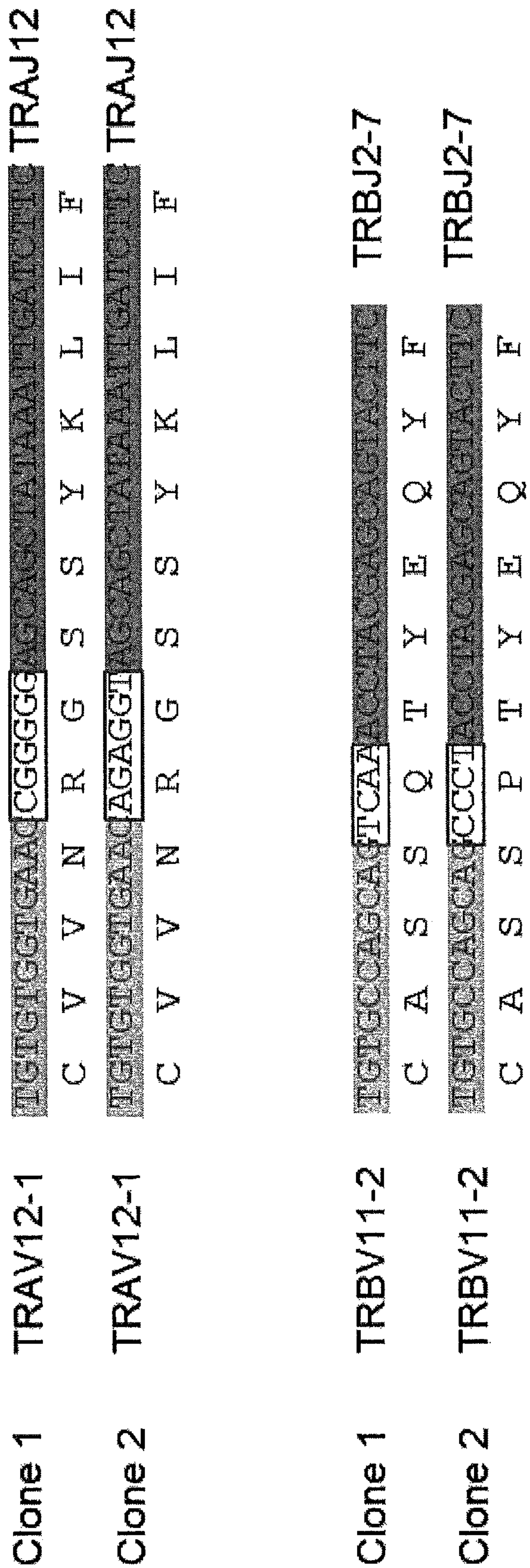
FIG. 2 is a diagram showing the alignment of TCR CDR3 sequences of clone 1 and clone 2.

Among these, TCRαβ pairs shared between patients were detected. These TCRαβ pairs were designated as clones 1 and 2, derived from patients Ts-017 and Ts-018, respectively, sharing identical Vα, Jα, Vβ, and Jβ usage. Furthermore, it was found that the CDR3α sequences of clones 1 and 2 were identical, and that CDR3β was identical except for one amino acid (Table 4 and FIG. 2). Although clones 1 and 2 were derived from different subjects, they were presumed to recognize the same epitope based on sequence similarity. Furthermore, both were identified from the Tfh cluster, and it was expected that the epitope would be an epitope that easily induces Tfh.

Figure 5:
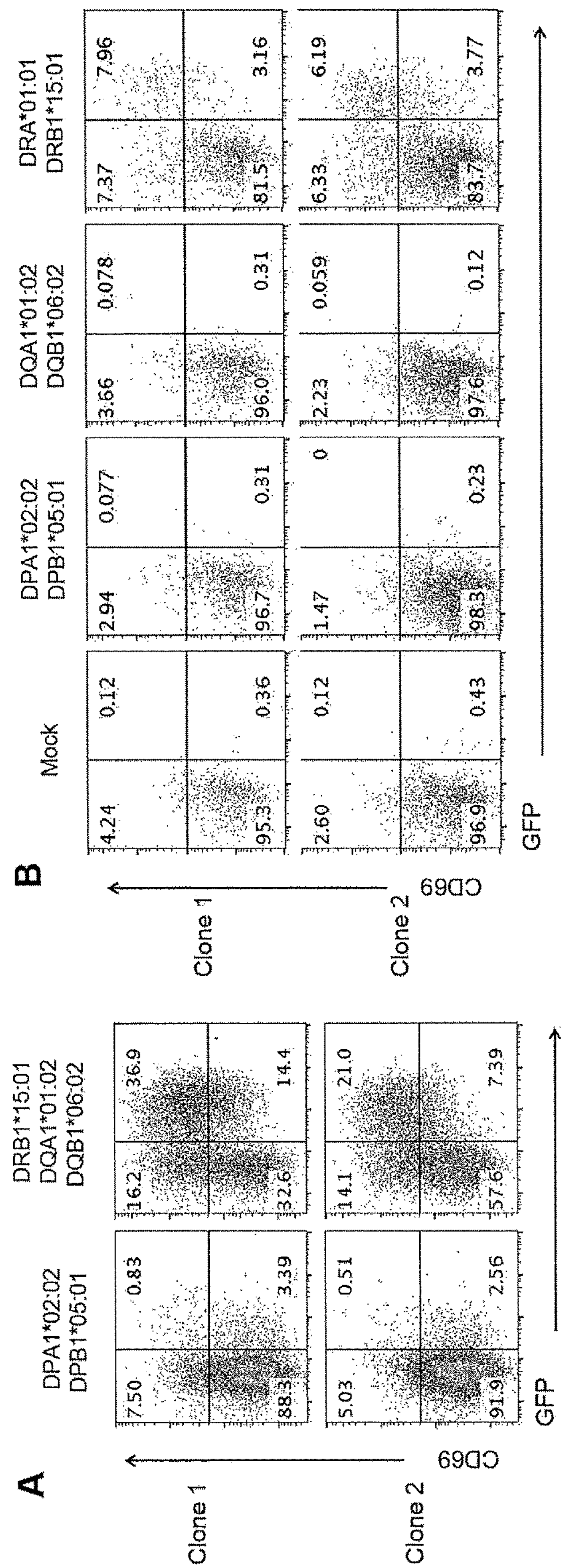
FIG. 5 is a diagram showing the identified HLA and S protein peptides recognized by S protein-responsive TCRs. T-cell hybridomas expressing TCRs of clonotype 1/2 (clone 1 and clone 2, respectively) were stimulated with S peptide pool #2 (0.3 μg/ml per peptide) in the presence of APCs derived from the same DP or other donor PBMCs having DR/DQ alleles with the original individual (FIG. 5A). Clones 1 and 2 were stimulated with S peptide pool #2 (0.3 μg/ml per peptide) in the presence of HEK293T cells expressing the indicated HLA (FIG. 5B).

Both clones 1 and 2 respond to S peptide pool #2 only in the presence of DRA*01:01 and DRB1*15:01, and DRA is monomorphic, suggesting that the responsiveness is determined by DRB1*15:01 (FIG. 5B).

Therefore, NetMHC server software (www.cbs.dtu.dk/services/NetMHCIIpan/) was used to search for candidate peptides predicted to bind to DRA-DRB1*15:01 (FIG. 5C).

Two strong binders ($S_{828-846}$ and $S_{864-882}$) were predicted as candidates within narrowed regions of S proteins (FIG. 5D). Then, by synthesizing two peptides and stimulating clones 1 and 2, peptide $S_{864-882}$ was determined as an epitope for both clones 1 and 2 (FIG. 5E).

TABLE 4

| | TRBV | CDR3β | TRBJ | TRAV | CDR3α | TRAJ | donor |
|---|---|---|---|---|---|---|---|
| Clone 1 | TRBV11-2 | CASSQTYEQYF | TRBJ2-7 | TRAV12-1 | CVVNRGSSYKLIF | TRAJ12 | patient #3 |
| Clone 2 | TRBV11-2 | CASSPTYEQYF | TRBJ2-7 | TRAV12-1 | CVVNRGSSYKLIF | TRAJ12 | patient #4 |
| Clone 2 | TRBV11-2 | CASSPTYEQYF | TRBJ2-7 | TRAV12-1 | CVVNRGSSYKLIF | TRAJ12 | patient #4 |

In patient Ts-018, clone 2 was detected as two different barcoded cells that share exactly the same TCR sequence. To examine the antigen-specificity of TCR, clonotypes 1 and 2, the respective TCR α and β chains were transfected into TCR-deficient T-cell hybridomas and TCR-reconstituted CD3+ cells were established (FIG. 1B).

These TCR transfectants were stimulated with various antigens in the presence of Epstein-Barr virus (EBV)-transformed B cells derived from each corresponding patient. Clones 1 and 2 responded to the recombinant S protein and S peptide pools, but not to the M+N peptide pool. This was consistent with the initial antigen-specificity revealed by single cell analysis (FIG. 3A).

Figure 3:
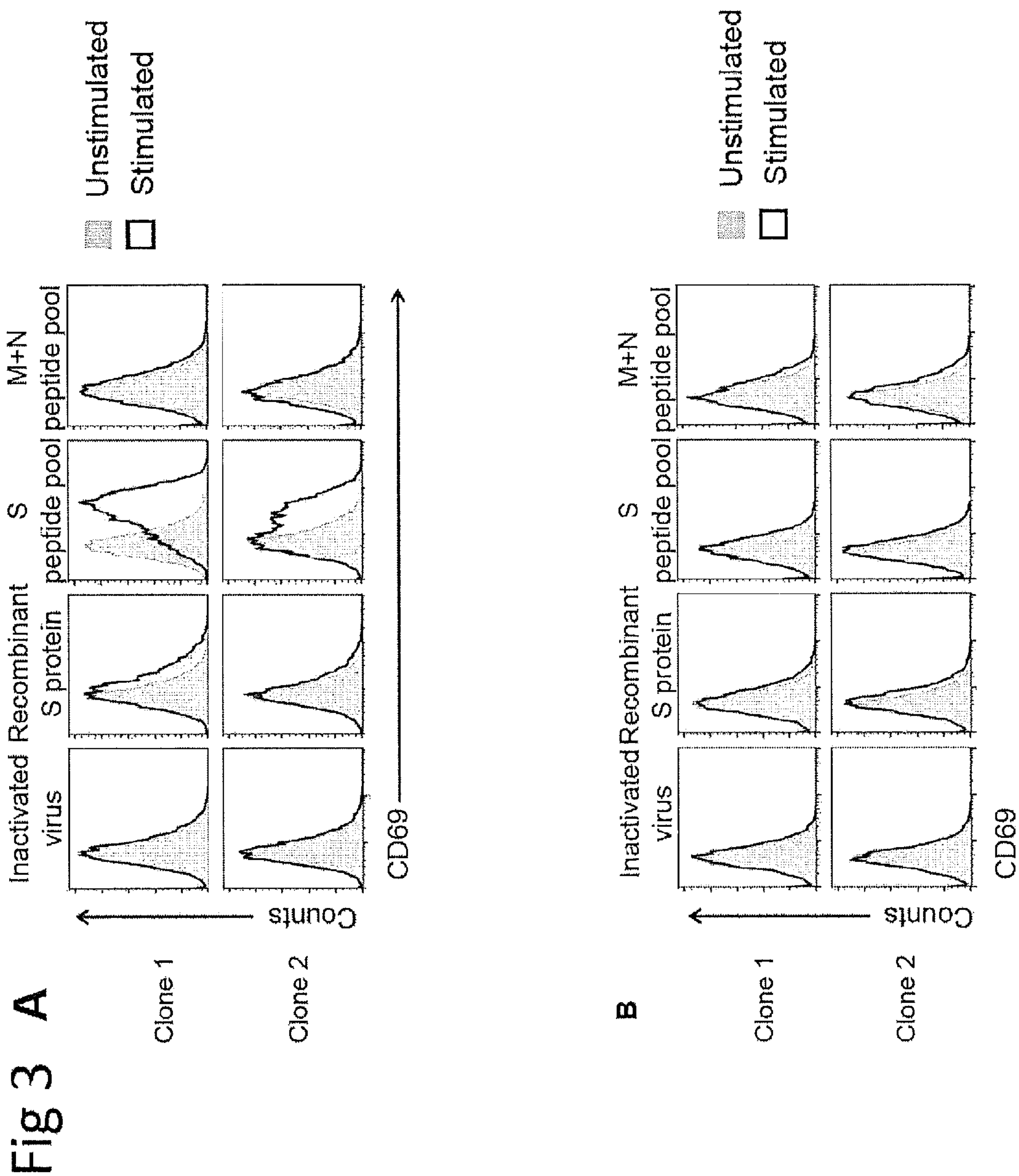
FIG. 3 is a diagram showing that TCR cloned from Tfh cells of patients is reactive with peptides derived from the SARS-CoV-2 S protein. T-cell hybridomas expressing TCRs of clonotype 1/2 (clone 1 and clone 2, respectively) were left unstimulated (filled histograms) or stimulated with inactivated virus (equivalent to 1 μg/ml S protein), recombinant S protein (1 μg/ml), or S peptide pool and M+N peptide pool (both 1 μg/ml per peptide) (open histograms), each for 20 hr in the presence (A) or absence (B) of the corresponding donor-derived APCs, and analyzed for CD69 expression (FIGS. 3A and 3B).
Figure 3:
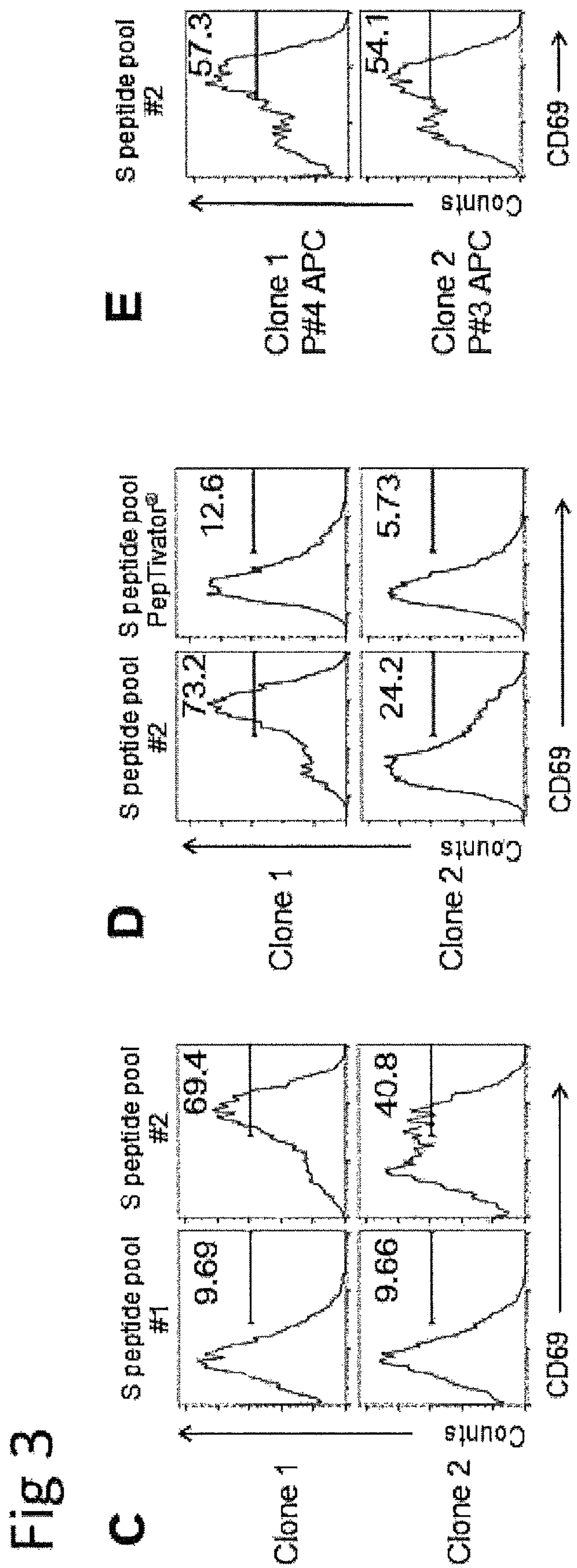

Since activation was excluded in the absence of antigen-presenting cells, it was confirmed that activation is mediated by MHC molecules (FIG. 3 B).

Of the two vials #1 ($S_{1-643}$) and #2 ($S_{633-1273}$) in which peptides $S_{1-643}$ and $S_{633-1273}$ were pooled, only the latter pool stimulated clones 1 and 2. It was found that the antigenic peptide was contained at positions 633-1273 of the S protein (FIG. 3C).

However, another available SARS-CoV-2 S peptide pool (PepTivator (registered trademark)) (FIG. 4) containing 175 peptides corresponding to positions 304-338, 421-475, 492-519, 683-707, 741-770, 785-802, and 885-1273 did not activate clones 1 and 2 (FIG. 3D).

Figure 4:
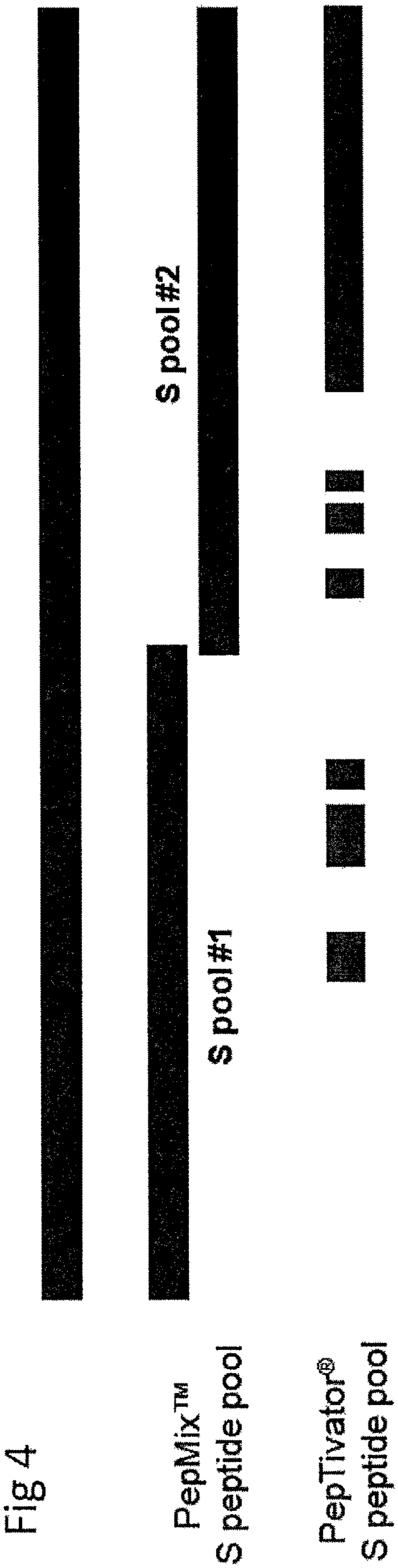
FIG. 4 is a diagram showing the relative positions of the coverage areas of peptide pools.

These results suggested that the antigenic epitopes of clone 1 and clone 2 were located at amino acids 633-682, 708-740, 771-784, or 803-884 of the S protein (FIG. 4).

The HLA alleles constraining clones 1 and 2 were then determined to further reduce the number of peptide candidates for the epitope.

It was found that antigen-presenting cells (APCs) collected from both patients Ts-017 and Ts-018 can activate clones 1 and 2. This indicates that APCs are interchangeable (FIG. 3 E). Therefore, each of the MHC class II alleles shared between Ts-017 and Ts-018, such as DRB1*15:01, DPA1*02:02-DPB1*05:01, DQA1*01:02-DQB1*06, and the like, was considered an HLA candidate. These alleles were then individually transfected to examine recognition of the S peptide by clones 1 and 2.

TCRs of clones 1 and 2 differ by one amino acid within CDR3 (Pro and Gln at position 89). Since both TCRs recognize the same epitope presented by the same MHC molecule and are from different donors, it was suggested that clones 1 and 2 are public clones. This epitope has low homology with the corresponding amino acid sequence of human coronavirus (HCoV)-OC43.

Figure 6:
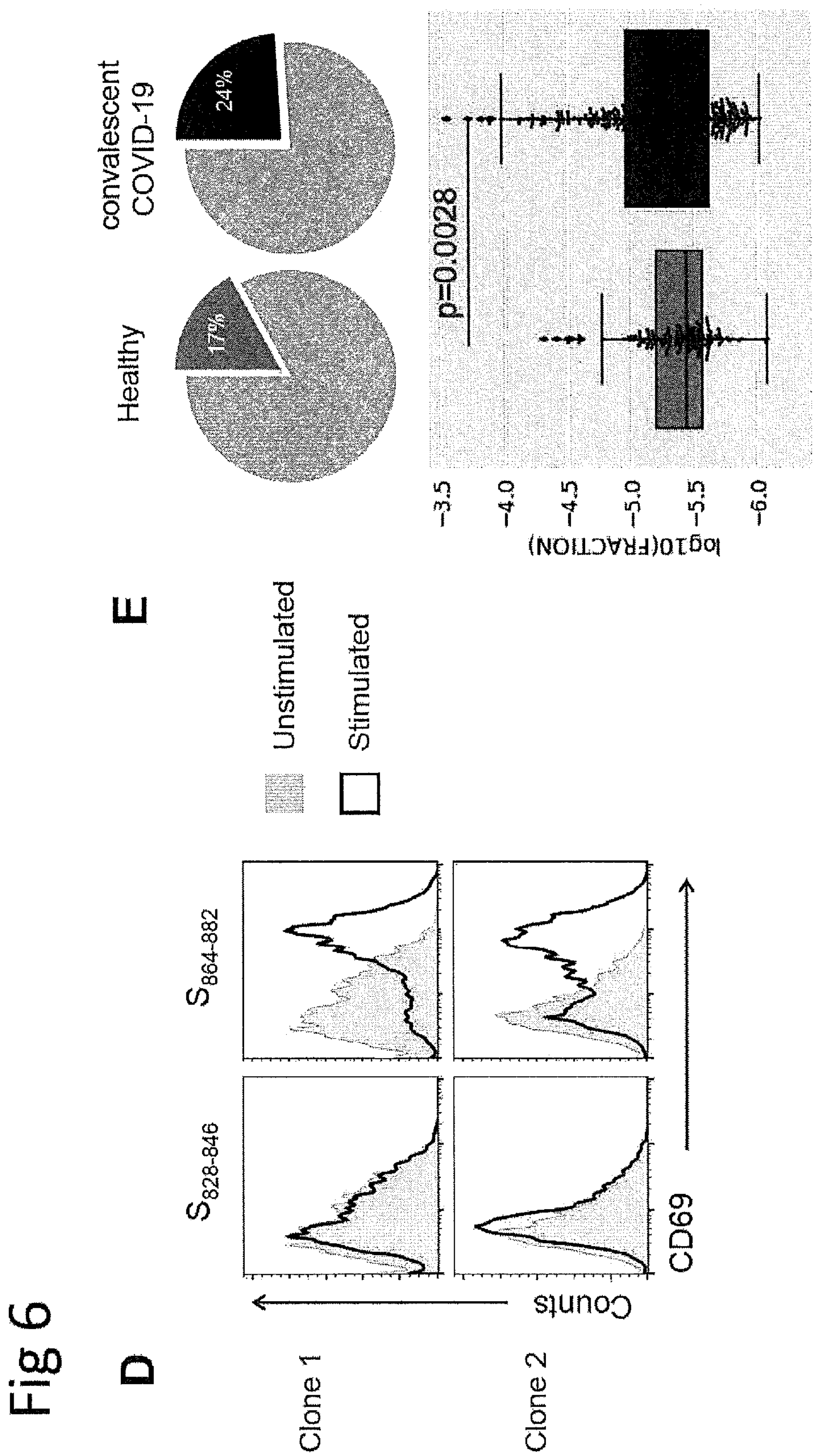

Indeed, neither clone 1 nor 2 responded at all to peptide pools and total proteins derived from HCoV-OC43S protein in the presence of APC expressing DRA-DRB1*15:01 (FIG. 6A). Furthermore, since none of the other HCoVs, including severe acute respiratory syndrome coronavirus (SARS-CoV) and Middle East respiratory syndrome-associated coronavirus (MERS-CoV), have similar epitopes (FIG. 6B), it was suggested that clone 1/2 is unlikely to cross-react with related human coronaviruses.

It was next examined whether MHC class II alleles other than DRB1*15:01 can present this antigenic peptide recognized by clone 1/2.

As a result, $S_{864-882}$ also was predicted as strong binders to DRB1*15:02 and 15:01 (FIG. 6C). Furthermore, the amino acid sequence identity between DRB1*15:01 and *15:02 is 99.6%. Therefore, it was speculated that DRB1*15:02 is also the allele responsible for epitope recognition, and APC from another individual who has DRB1*15:02 but not DRB1*15:01 was tested. As a result, DRB1*15:02 was identified as being able to stimulate both clones 1 and 2 in the presence of this particular peptide (FIG. 6D).

Example 2: Identification of Epitopes

Figure 9:
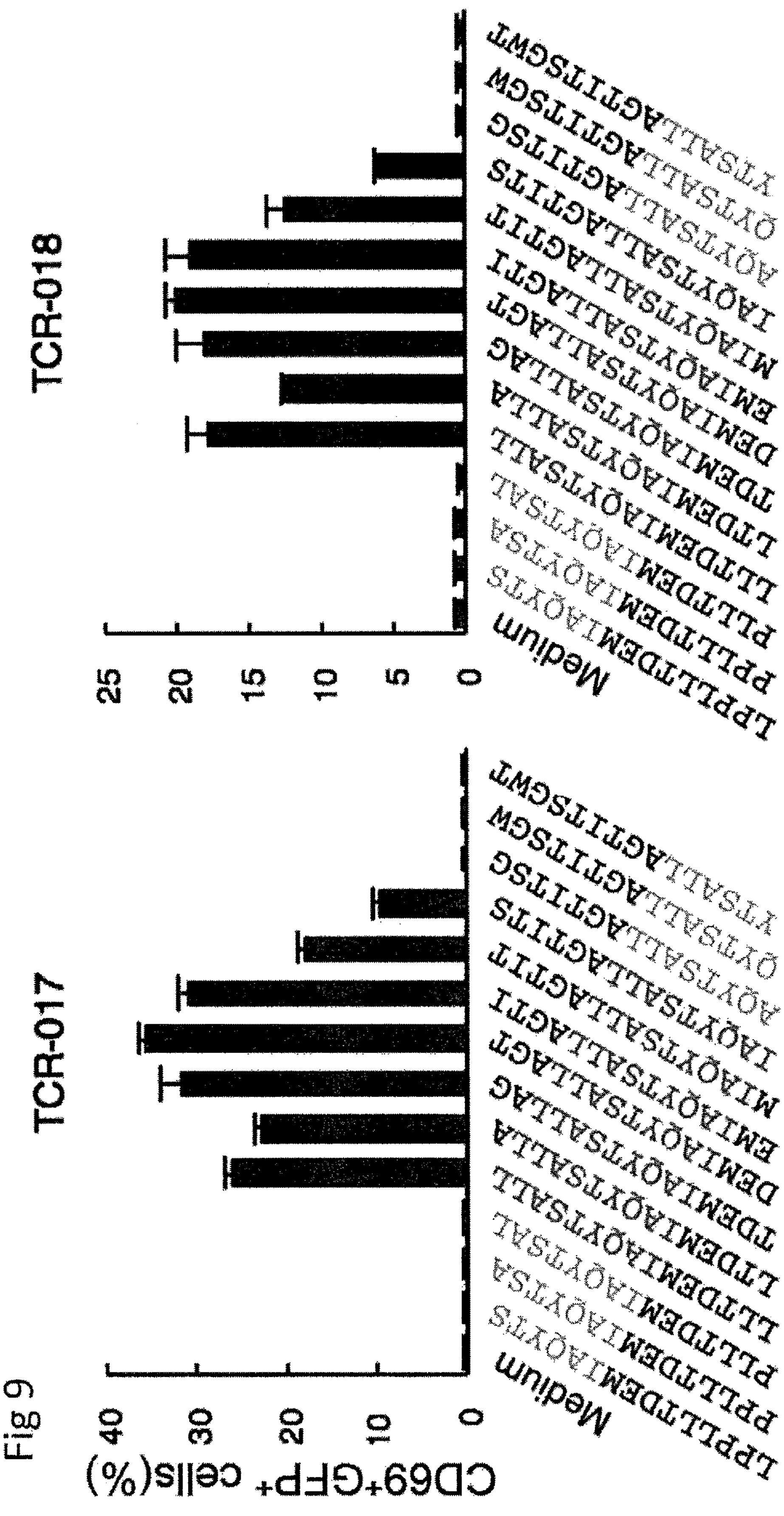
[FIG. 9]

In order to further identify the sequence of epitope, 13 polypeptides (SEQ ID NOS: 44-56) including $S_{864-882}$ peptide and the surrounding peptides were synthesized. Whether they are recognized by Clone 1/2 was investigated. Specifically, the details are as follows. Cells expressing clone 1/2 (TCR-017 or TCR-018) found in Example 1 were produced as follows. Clone 1/2 (TCR-017 or TCR-018) cDNA sequences were synthesized and cloned into the retroviral vectors pMX-IRES-rat CD2 and pMX-IRES-human CD8, respectively. The two vectors were co-transfected into Phoenix packaging cells by using PEI MAX (Polysciences). Supernatants containing the retrovirus were used to infect mouse T-cell hybridomas harboring the NFAT-GFP reporter gene to reconstitute the TCRαβ pair. The cells were stimulated with 1 μg/ml of the synthesized peptide in the presence of APC derived from patient Ts-018, and 20 hr after stimulation, T cell activation was evaluated by the expression of GFP or CD69. As a result, as shown in FIG. 9, the sequence of SEQ ID NO: 13 was found to be essential for activation.

Example 3: Determination of Public Tfh and Epitope-2

Considering the frequency of DRB1*15:02 (10.6%) and *15:01 (7.7%) in the Japanese population (hla.or.jp/), if these clonotypes are present, clones 1 and 2 were expected to respond to this peptide in 18.3% of the population. In this Example, clone 1/2 was confirmed in 2 out of 6 patients (33%).

Next, the occurrence of the clone 2/3 clonotype in Japanese blood donor samples before the SARS-CoV-2 pandemic was examined. It was found that 9 out of 27 individuals had the clone 1/2 TCRβ clonotype. This is similar to the ratio in this Example.

Next, considering that clone 1/2 is SARS-CoV-2-specific T cell exhibiting a Tfh profile, it was hypothesized that clone 1/2 was clonally expanded during infection to promote defensive humoral immunity and the following examination was performed.

DRB1*15:01/15:02 is not a minor allele in the world (see www.allelefrequencies.net/tools/Report.aspx). Thus, frequency of clone 1/2 clonotypes in healthy individuals (n=786) and individuals (n=1,413) who have recovered from COVID-19 was examined in a public database of US citizens (immune response actions to COVID-19 events; ImmuneRace, immunerace.adaptivebiotech.com/). Clonotypes were detected in approximately 17% and 24% of the healthy and COVID-19 recovered groups, respectively (FIG. 5E, top). Notably, the frequency of this clonotype among each individual was significantly increased (p=0.0028) in the COVID-19 recovered group compared to healthy controls, suggesting that this S protein-specific clone was clonally expanded in different individuals during infection (FIG. 4E, bottom). Interestingly, the frequency of clonotype 1/2 in recovered patients is greater than the allele frequency of DRB1*15:01 or 15:02 worldwide (11.3%). Thus, it was possible that clone 1/2 recognized other epitopes derived from SARS-CoV-2 presented by other HLA alleles.

Figure 10:
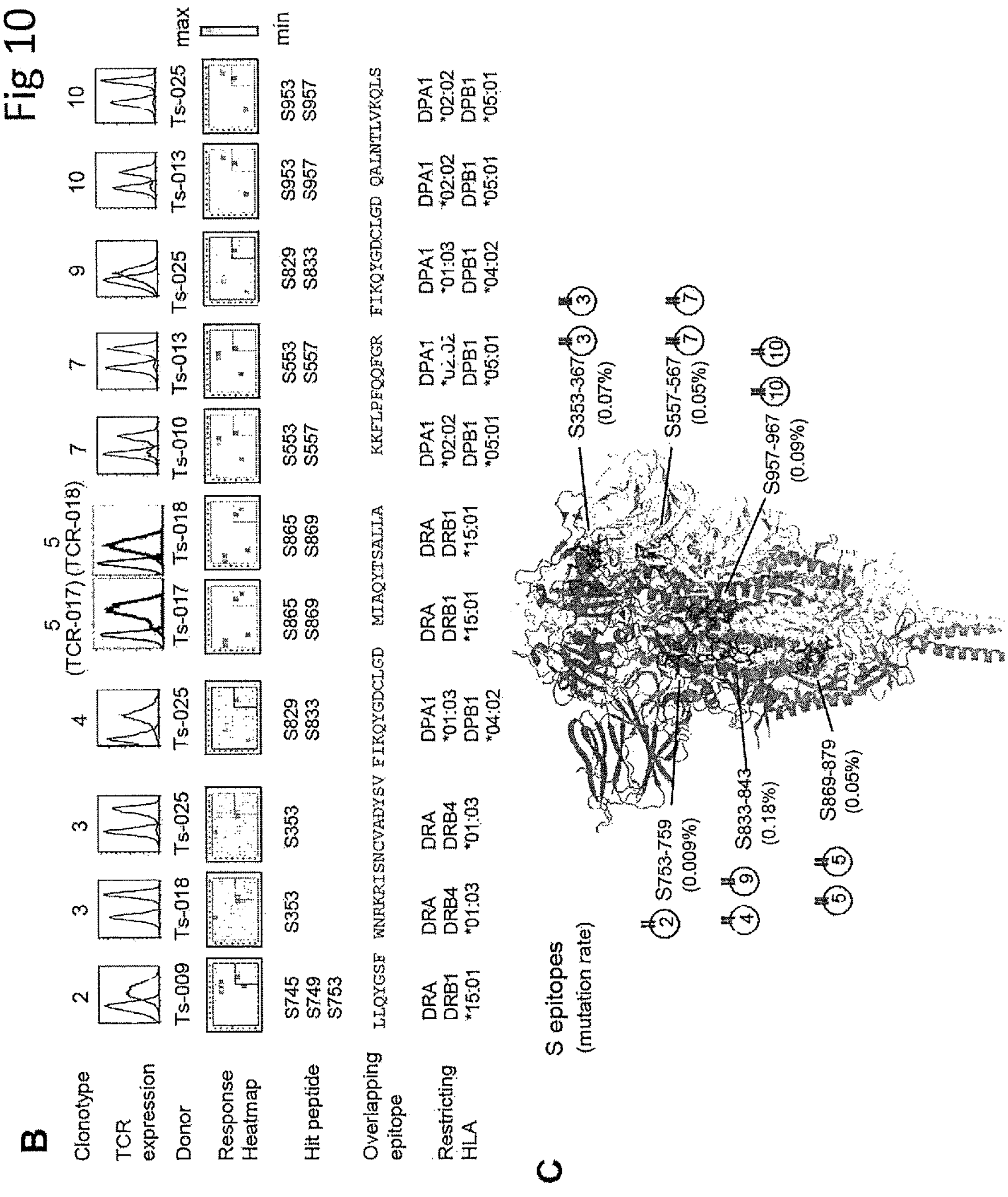

Then activated marker-positive T cells were selected from peripheral blood isolated from healthy donors and recovered COVID patients stimulated with SARS-CoV-2-derived antigens to produce Tfh clusters. Of the 1735 TCR pairs identified by of the present inventors in this Tfh cluster, 10 Tfh clonotypes that were significantly increased in recovered COVID-19 patients as compared with a healthy cohort were identified (FIG. 10). Notably, half of such clonotypes were actually detected in multiple patients in the sample pool by single-cell TCR sequencing, and TCR-017/018, found in Example 1, was found to be a clonotype with the fifth largest increase.

In order to efficiently determine the epitopes of these clone types, a rapid epitope determination platform was established (FIG. 10B).

The scheme of the rapid epitope determination platform for identifying T cell clonal epitopes is as follows. Approximately 300 types of 15-mer peptides with overlapping 11 amino acids, covering the entire length of the S protein of SARS-CoV-2, were synthesized and pooled in multiple 96-well plates. Epitopes for each clone type are determined by examining which peptide activates the clone type.

By using this platform, the epitopes of other Tfh clones that have increased due to COVID-19 were determined (FIG. 10B). As a result, it was found that the public Tfh clonotype, which increased significantly in recovered patients, preferentially recognizes the S epitope (FIG. 10A, B). All epitopes identified were located in two major hotspots within the conserved trimerization interface of S protein with low mutation rates (FIG. 10C). Moreover, these clonal donors had anti-RBD and neutralizing antibodies. These results suggest that public Tfh clonotype specific to conserved S protein epitopes spread during SARS-CoV-2 infection and contributed to the recovery from mild symptoms.

Example 4: Restimulation Assay of Peripheral Blood Mononuclear Cell (PBMC) by SARS-CoV-2 $S_{864-882}$ Peptide PBMC $1.0\times10^5$ cells obtained from experiment participants were suspended of RPMI1640 medium (supplemented with 5% human serum and penicillin/streptomycin), SARS-CoV-2 $S_{864-882}$ peptide was added at 1 μg/ml, and the cells were cultured in a 96-well plate (U bottom) (Day 0).

Next, human IL-2 was added at 10 IU/ml on Day 4 and Day 7. Passage of the medium was performed as appropriate.

On Day 10, the cells were sorted as follows using cell sorter SH-800S (SONY). The cells were stained using CD3, CD4 antibodies and PI, and sorted in the order of FSC SSC gating, PI negative gating, CD3 positive gating, and CD4 positive cells. At that time, staining was performed using CXCR5, CD45RA, and PD-1 antibodies, and FCM analysis was also performed.

CD4 positive cells ($2.0\times10^4$ cells) obtained by sorting and B cells ($3.0\times10^3$ cells) derived from a patient immortalized by EBV infection were suspended in 50 μl of RPMI1640 medium (5% human serum) and cultured in multiple wells using a 96-well plate (U bottom). To half of them, the SARS-CoV-2 $S_{864-882}$ peptide was added to the medium at 1 μg/ml.

Figure 7:
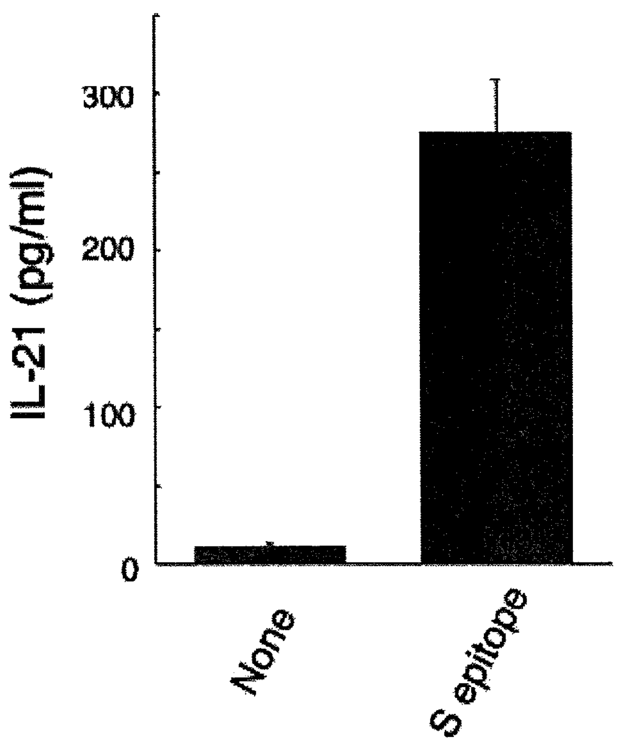
[FIG. 7]

After 24 hr, the supernatant of the medium was collected and human IL-21 was measured using ELISA. The measurement results are shown in FIG. 7.

The measurement results showed that when stimulated with SARS-CoV-2 $S_{864-882}$ peptide, the concentration of IL-21 in the medium was higher than when it was not stimulated. IL-21 is a characteristic cytokine produced by follicular T cells. This result suggests preferential induction of follicular T cells from the starting sample PBMC.

Example 5: Close Examination of Amino Acid Sequence Using Alanine Scan

Figure 8:
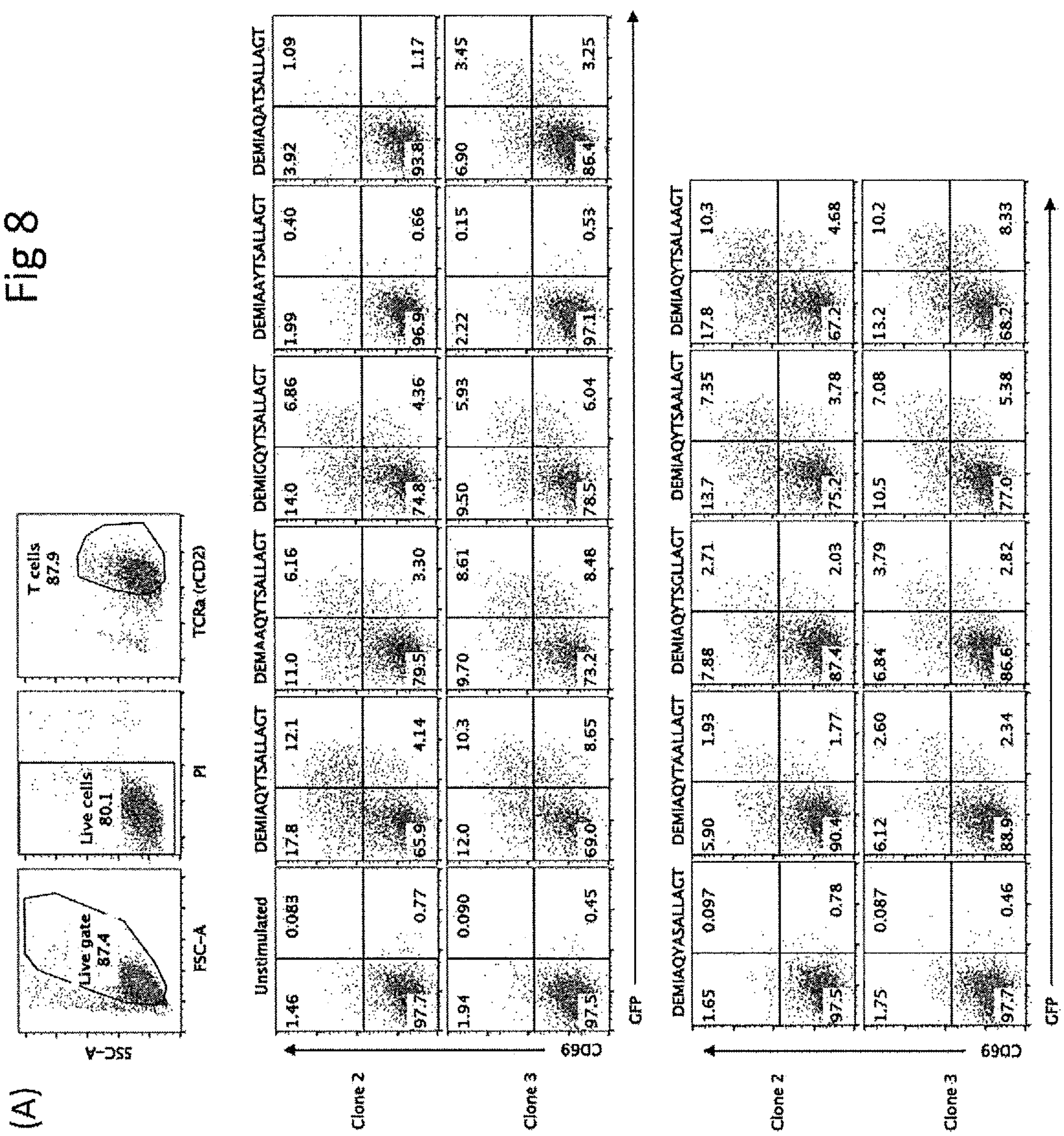
Figure 8:
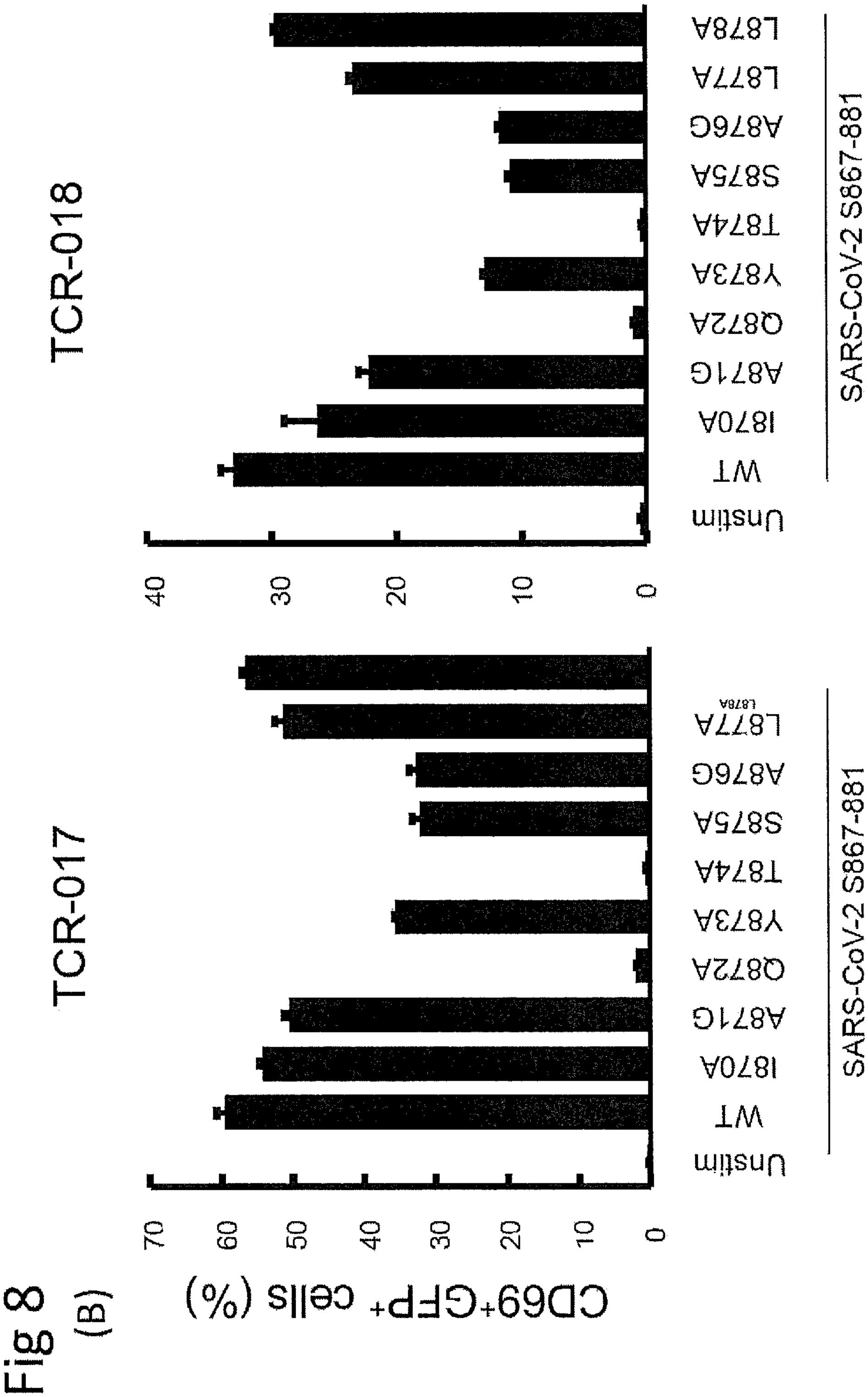

An amino acid sequence was produced by replacing each amino acid in the amino acid sequence of SEQ ID NO: 13 with alanine (amino acid sequence in which when the original was alanine, it was replaced with glycine), and whether it was recognized by clone 1/2 was examined. Specifically, the details are as follows. TCRαβ-reconstituted cells produced in Example 2 were stimulated with 1 μg/ml of $S_{867-881}$ peptide containing the indicated mutation in the presence of APC derived from patient Ts-018, and 20 hr after stimulation, T cell activation was evaluated by the expression of GFP or CD69. As a result, as shown in FIG. 8, it was found that when Q and T were replaced, it was no longer recognized.

Note that the present invention is not limited to the above Examples, and various modifications can be made within the scope of the gist of the present invention.

Note

As described above, while the present invention has been illustrated using the preferred embodiments of the present invention, the present invention should not be construed as being limited to those embodiments. It is understood that the present invention is to be construed in scope only by the claims. It is understood that a person skilled in the art can implement an equivalent range from the description of specific preferred embodiments of the present invention based on the description of the present invention and common general technical knowledge. It is also understood that any patent, any patent application, and any references cited herein should be incorporated herein by reference in the same manner as the contents are specifically described herein. This application claims priority based on a patent application No. 2021-42666 filed in Japan (filing date: Mar. 16, 2021), the contents of which are incorporated in full herein by reference.

INDUSTRIAL APPLICABILITY

The present invention can be used in fields such as vaccine development, cell therapy, and the like.

[Sequence Listing Free Text]

SEQ ID NO: 1 (amino acid sequence of specific epitope site of $S_{864-882}$)

SEQ ID NO: 2 (amino acid sequence of CDR3a of clones 1 and 2)

SEQ ID NO: 3 (amino acid sequence of CDR3β of clone 1)

SEQ ID NO: 4 (amino acid sequence of CDR3β of clone 2)

SEQ ID NO: 5 (amino acid sequence of follicular T cell epitope)

SEQ ID NO: 6 (amino acid sequence of follicular T cell epitope)

SEQ ID NO: 7 (amino acid sequence of follicular T cell epitope)

SEQ ID NO: 8 (amino acid sequence of follicular T cell epitope)

SEQ ID NO: 9 (amino acid sequence of follicular T cell epitope)

SEQ ID NO: 10 (amino acid sequence of follicular T cell epitope)

SEQ ID NO: 11 (amino acid sequence of follicular T cell epitope)

SEQ ID NO: 12 (amino acid sequence of follicular T cell epitope)

SEQ ID NO: 13 (amino acid sequence of follicular T cell epitope)

SEQ ID NO: 14 (amino acid sequence of CDR3α of clone 1-1 in FIG. 10A)

SEQ ID NO: 16 (amino acid sequence of CDR3α of clone 1-2 in FIG. 10A)

SEQ ID NO: 15 (amino acid sequence of CDR3β of clone 1-2 in FIG. 10A)

SEQ ID NO: 17 (amino acid sequence of CDR3α of clone 2 in FIG. 10A)

SEQ ID NO: 18 (amino acid sequence of CDR3β of clone 2 in FIG. 10A)

SEQ ID NO: 19 (amino acid sequence of CDR3α of clone 3-1 in FIG. 10A)

SEQ ID NO: 20 (amino acid sequence of CDR3β of clone 3-1 in FIG. 10A)

SEQ ID NO: 21 (amino acid sequence of CDR3α of clone 3-2 in FIG. 10A)

SEQ ID NO: 22 (amino acid sequence of CDR3α of clone 4 in FIG. 10A)

SEQ ID NO: 23 (amino acid sequence of CDR3β of clone 4 in FIG. 10A)

SEQ ID NO: 24 (amino acid sequence of CDR3β of clone 5-2 in FIG. 10A)

SEQ ID NO: 25 (amino acid sequence of CDR3α of clone 6 in FIG. 10A)

SEQ ID NO: 26 (amino acid sequence of CDR3β of clone 6 in FIG. 10A)

SEQ ID NO: 27 (amino acid sequence of CDR3α of clone 7-1 in FIG. 10A)

SEQ ID NO: 28 (amino acid sequence of CDR3β of clone 7-1 in FIG. 10A)

SEQ ID NO: 29 (amino acid sequence of CDR3α of clone 7-2 in FIG. 10A)

SEQ ID NO: 30 (amino acid sequence of CDR3α of clone 8 in FIG. 10A)

SEQ ID NO: 31 (amino acid sequence of CDR3β of clone 8 in FIG. 10A)

SEQ ID NO: 32 (amino acid sequence of CDR3α of clone 9 in FIG. 10A)

SEQ ID NO: 33 (amino acid sequence of CDR3β of clone 9 in FIG. 10A)

SEQ ID NO: 34 (amino acid sequence of CDR3α of clone 10-1 in FIG. 10A)

SEQ ID NO: 35 (amino acid sequence of CDR3β of clone 10-1 in FIG. 10A)

SEQ ID NO: 36 (amino acid sequence of CDR3α of clone 10-2 in FIG. 10A)

SEQ ID NO: 37 (amino acid sequence of CDR3β of clone 10-2 in FIG. 10A)

SEQ ID NO: 38 (amino acid sequence of follicular T cell epitope)

SEQ ID NO: 39 (amino acid sequence of follicular T cell epitope)

SEQ ID NO: 40 (amino acid sequence of follicular T cell epitope)

SEQ ID NO: 41 (amino acid sequence of follicular T cell epitope)

SEQ ID NO: 42 (amino acid sequence of follicular T cell epitope)

SEQ ID NO: 43 (amino acid sequence of follicular T cell epitope)

SEQ ID NO: 44 (amino acid sequence of part of protein of SARS-CoV-2)

SEQ ID NO: 45 (Amino acid sequence of part of protein of SARS-CoV-2)

SEQ ID NO: 46 (amino acid sequence of part of protein of SARS-CoV-2)

SEQ ID NO: 47 (amino acid sequence of part of protein of SARS-CoV-2)

SEQ ID NO: 48 (amino acid sequence of part of protein of SARS-CoV-2)

SEQ ID NO: 49 (amino acid sequence of part of protein of SARS-CoV-2)

SEQ ID NO: 50 (amino acid sequence of part of protein of SARS-CoV-2)

SEQ ID NO: 51 (amino acid sequence of part of protein of SARS-CoV-2)
SEQ ID NO: 52 (amino acid sequence of part of protein of SARS-CoV-2)
SEQ ID NO: 53 (amino acid sequence of part of protein of SARS-CoV-2)
SEQ ID NO: 54 (amino acid sequence of part of protein of SARS-CoV-2)
SEQ ID NO: 55 (amino acid sequence of part of protein of SARS-CoV-2)
SEQ ID NO: 56 (Amino acid sequence of part of protein of SARS-CoV-2)

The invention claimed is:

1. A method for inducing a follicular T cell reactive with SARS-CoV-2, comprising a step of administering SARS-CoV-2 protein or a part thereof to a test subject, wherein said follicular T cell has a TCRαβ pair selected from the group consisting of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEO ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

2. The method of claim 1, wherein said follicular T cell is also reactive with a coronavirus other than SARS-CoV-2.

3. The method of claim 1, wherein said follicular T cell is specific to SARS-CoV-2.

4. A method for inducing a follicular T cell reactive with at least one coronavirus, comprising a step of administering a SARS-CoV-2 protein or a part thereof to a test subject, wherein said follicular T cell is a public follicular T cell.

5. The method of claim 4, wherein said SARS-CoV-2 protein or a part thereof preferentially induces follicular T cell s as compared to other T cell types when recognizing the same SARS-CoV-2 epitopes.

6. The method of claim 4, wherein said SARS-CoV-2 protein or a part thereof induces a follicular T cell in an HLA type-specific manner.

7. The method of claim 4, wherein said SARS-CoV-2 protein or a part thereof comprises the sequence of the spike protein expressed by SARS-CoV-2 or a part thereof.

8. The method of claim 4, wherein said SARS-CoV-2 protein or a part thereof comprises SEQ ID NO: 5, $X_1$ is I, V, A, L, P, W, F, M or G,
$X_2$ is A, V, I, L, P, W, F, M or G,
$X_3$ is Q,
$X_4$ is Y, G, S, T, N, Q, C or F,
$X_5$ is T,
$X_6$ is S, Y, G, N, Q, C, F or T,
$X_7$ is A, L, I, V, P, W, F, M or G,
$X_8$ is L, A, I, V, P, W, F, M or G, and
$X_9$ is L, A, I, V, P, W, F, M or G.

9. The method of claim 4, wherein said SARS-CoV-2 protein or a part thereof comprises SEQ ID NO: 5, $X_1$ is I, V, A, L or G,
$X_2$ is A, V, I, L or G,
$X_3$ is Q,
$X_4$ is Y or F,
$X_5$ is T,
$X_6$ is S or T,
$X_7$ is A, L, I, V or G,
$X_8$ is L, A, I, V or G, and
$X_9$ is L, A, I, V or G.

10. The method of claim 6, wherein said SARS-CoV-2 protein or a part thereof comprises SEQ ID NO: 6, SEQ ID NO: 7, SEQ ID NO: 8, SEQ ID NO: 9, SEQ ID NO: 10, SEQ ID NO: 11, or SEQ ID NO: 12.

11. The method of claim 4, wherein said SARS-CoV-2 protein or a part thereof comprises the amino acid sequence shown in SEQ ID NO:1.

12. The method of claim 4, wherein said SARS-CoV-2 protein or a part thereof consists of the amino acid sequence shown in SEQ ID NO:1.

13. The method of claim 4, wherein said SARS-CoV-2 protein or a part thereof comprises the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43, and is at least 9 amino acids long.

14. The method of claim 4, wherein said SARS-CoV-2 protein or a part thereof consists of the amino acid sequence shown in SEQ ID NO: 13, SEQ ID NO: 38, SEQ ID NO: 39, SEQ ID NO: 40, SEQ ID NO: 41, SEQ ID NO: 42, or SEQ ID NO: 43.

15. The method of claim 4, wherein said follicular T cell is a public follicular T cell, and/or wherein said follicular T cell has a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

16. A method for enhancing immunity acquisition against SARS-CoV-2, comprising: (a) obtaining a biological sample from a subject: (b) isolating, follicular T cells from said biological sample: (c) contacting said follicular T cells with a SARS-CoV-2 protein or a part thereof ex vivo; (d) expanding said follicular T cells reactive with SARS-CoV-2 ex vivo under conditions suitable for T cell proliferation; and (e) administering said expanded follicular T cells to the subject via intravenous injection.

17. The method of claim 16, wherein said follicular T cells are also reactive with a coronavirus other than SARS-Cov-2.

18. The method of claim 16, wherein said follicular T cells are specific to SARS-CoV-2.

19. The method of claim 16, wherein said follicular T cells are public follicular T cells having a TCRαβ pair of SEQ ID NO: 2 and SEQ ID NO: 3, SEQ ID NO: 2 and SEQ ID NO: 4, SEQ ID NO: 14 and SEQ ID NO: 15, SEQ ID NO: 16 and SEQ ID NO: 15, SEQ ID NO: 17 and SEQ ID NO: 18, SEQ ID NO: 19 and SEQ ID NO: 20, SEQ ID NO: 21 and SEQ ID NO: 20, SEQ ID NO: 22 and SEQ ID NO: 23, SEQ ID NO: 2 and SEQ ID NO: 24, SEQ ID NO: 25 and SEQ ID NO: 26, SEQ ID NO: 27 and SEQ ID NO: 28, SEQ ID NO: 29 and SEQ ID NO: 28, SEQ ID NO: 30 and SEQ ID NO: 31, SEQ ID NO: 32 and SEQ ID NO: 33, SEQ ID NO: 34 and SEQ ID NO: 35, or SEQ ID NO: 36 and SEQ ID NO: 37.

* * * * *

SEQUENCE LISTING

```
<160> NUMBER OF SEQ ID NOS: 56

<210> SEQ ID NO 1
<211> LENGTH: 19
<212> TYPE: PRT
<213> ORGANISM: artificial sequence
<220> FEATURE:
<223> OTHER INFORMATION: amino acid sequence of S864 - S882 of
      SARS-CoV-2

<400> SEQUENCE: 1

Leu Leu Thr Asp Glu Met Ile Ala Gln Tyr Thr Ser Ala Leu Leu Ala
1               5                   10                  15

Gly Thr Ile


<210> SEQ ID NO 2
<211> LENGTH: 13
<212> TYPE: PRT
<213> ORGANISM: artificial sequence
<220> FEATURE:
<223> OTHER INFORMATION: amino acid sequence of CDR3 alpha of clone 1
      and 2

<400> SEQUENCE: 2

Cys Val Val Asn Arg Gly Ser Ser Tyr Lys Leu Ile Phe
1               5                   10


<210> SEQ ID NO 3
<211> LENGTH: 11
<212> TYPE: PRT
<213> ORGANISM: artificial sequence
<220> FEATURE:
<223> OTHER INFORMATION: amino acid sequence of CDR3 beta of clone 1

<400> SEQUENCE: 3

Cys Ala Ser Ser Gln Thr Tyr Glu Gln Tyr Phe
1               5                   10


<210> SEQ ID NO 4
<211> LENGTH: 10
<212> TYPE: PRT
<213> ORGANISM: artificial sequence
<220> FEATURE:
<223> OTHER INFORMATION: amino acid sequence of CDR3 beta of clone 2

<400> SEQUENCE: 4

Cys Ala Ser Ser Pro Thr Tyr Glu Gln Tyr
1               5                   10


<210> SEQ ID NO 5
<211> LENGTH: 9
<212> TYPE: PRT
<213> ORGANISM: artificial sequence
<220> FEATURE:
<223> OTHER INFORMATION: amino acid sequence of epitope of SARS-CoV-2
      for focillar helper T cell
<220> FEATURE:
<221> NAME/KEY: misc_feature
<222> LOCATION: (1)..(9)
<223> OTHER INFORMATION: Xaa can be any naturally occurring amino acid
```

<400> SEQUENCE: 5

Xaa Xaa Xaa Xaa Xaa Xaa Xaa Xaa Xaa
1 5

<210> SEQ ID NO 6
<211> LENGTH: 9
<212> TYPE: PRT
<213> ORGANISM: artificial sequence
<220> FEATURE:
<223> OTHER INFORMATION: amino acid sequence of epitope of SARS-CoV-2 for focillar helper T cell
<220> FEATURE:
<221> NAME/KEY: misc_feature
<222> LOCATION: (1)..(1)
<223> OTHER INFORMATION: Xaa can be any naturally occurring amino acid

<400> SEQUENCE: 6

Xaa Ala Gln Tyr Thr Ser Ala Leu Leu
1 5

<210> SEQ ID NO 7
<211> LENGTH: 9
<212> TYPE: PRT
<213> ORGANISM: artificial sequence
<220> FEATURE:
<223> OTHER INFORMATION: amino acid sequence of epitope of SARS-CoV-2 for focillar helper T cell
<220> FEATURE:
<221> NAME/KEY: misc_feature
<222> LOCATION: (2)..(2)
<223> OTHER INFORMATION: Xaa can be any naturally occurring amino acid

<400> SEQUENCE: 7

Ile Xaa Gln Tyr Thr Ser Ala Leu Leu
1 5

<210> SEQ ID NO 8
<211> LENGTH: 10
<212> TYPE: PRT
<213> ORGANISM: artificial sequence
<220> FEATURE:
<223> OTHER INFORMATION: amino acid sequence of epitope of SARS-CoV-2 for focillar helper T cell
<220> FEATURE:
<221> NAME/KEY: misc_feature
<222> LOCATION: (4)..(4)
<223> OTHER INFORMATION: Xaa can be any naturally occurring amino acid

<400> SEQUENCE: 8

Ile Ala Gln Xaa Tyr Thr Ser Ala Leu Leu
1 5 10

<210> SEQ ID NO 9
<211> LENGTH: 9
<212> TYPE: PRT
<213> ORGANISM: artificial sequence
<220> FEATURE:
<223> OTHER INFORMATION: amino acid sequence of epitope of SARS-CoV-2 for focillar helper T cell
<220> FEATURE:
<221> NAME/KEY: misc_feature
<222> LOCATION: (6)..(6)
<223> OTHER INFORMATION: Xaa can be any naturally occurring amino acid

<400> SEQUENCE: 9

Ile Ala Gln Tyr Thr Xaa Ala Leu Leu
1 5

<210> SEQ ID NO 10

```
<211> LENGTH: 9
<212> TYPE: PRT
<213> ORGANISM: artificial sequence
<220> FEATURE:
<223> OTHER INFORMATION: amino acid sequence of epitope of SARS-CoV-2
      for focillar helper T cell
<220> FEATURE:
<221> NAME/KEY: misc_feature
<222> LOCATION: (7)..(7)
<223> OTHER INFORMATION: Xaa can be any naturally occurring amino acid

<400> SEQUENCE: 10

Ile Ala Gln Tyr Thr Ser Xaa Leu Leu
1               5


<210> SEQ ID NO 11
<211> LENGTH: 9
<212> TYPE: PRT
<213> ORGANISM: artificial sequence
<220> FEATURE:
<223> OTHER INFORMATION: amino acid sequence of epitope of SARS-CoV-2
      for focillar helper T cell
<220> FEATURE:
<221> NAME/KEY: misc_feature
<222> LOCATION: (8)..(8)
<223> OTHER INFORMATION: Xaa can be any naturally occurring amino acid

<400> SEQUENCE: 11

Ile Ala Gln Tyr Thr Ser Ala Xaa Leu
1               5


<210> SEQ ID NO 12
<211> LENGTH: 9
<212> TYPE: PRT
<213> ORGANISM: artificial sequence
<220> FEATURE:
<223> OTHER INFORMATION: amino acid sequence of epitope of SARS-CoV-2
      for focillar helper T cell
<220> FEATURE:
<221> NAME/KEY: misc_feature
<222> LOCATION: (9)..(9)
<223> OTHER INFORMATION: Xaa can be any naturally occurring amino acid

<400> SEQUENCE: 12

Ile Ala Gln Tyr Thr Ser Ala Leu Xaa
1               5


<210> SEQ ID NO 13
<211> LENGTH: 9
<212> TYPE: PRT
<213> ORGANISM: artificial sequence
<220> FEATURE:
<223> OTHER INFORMATION: amino acid sequence of epitope of SARS-CoV-2
      for focillar helper T cell

<400> SEQUENCE: 13

Ile Ala Gln Tyr Thr Ser Ala Leu Leu
1               5


<210> SEQ ID NO 14
<211> LENGTH: 14
<212> TYPE: PRT
<213> ORGANISM: artificial sequence
<220> FEATURE:
<223> OTHER INFORMATION: amino acid sequence of CDR3 alpha of clone 1-1

<400> SEQUENCE: 14

Cys Val Val Ser Arg Thr Gly Gly Gly Asn Lys Leu Thr Phe
1               5                   10
```

<210> SEQ ID NO 15
<211> LENGTH: 15
<212> TYPE: PRT
<213> ORGANISM: artificial sequence
<220> FEATURE:
<223> OTHER INFORMATION: amino acid sequence of CDR3 beta of clone 1-1

<400> SEQUENCE: 15

```
Cys Ala Ser Ser Gln Ala Gly Gly Ser Thr Asp Thr Gln Tyr Phe
1               5                   10                  15
```

<210> SEQ ID NO 16
<211> LENGTH: 12
<212> TYPE: PRT
<213> ORGANISM: artificial sequence
<220> FEATURE:
<223> OTHER INFORMATION: amino acid sequence of CDR3 alpha of clone 1-2

<400> SEQUENCE: 16

```
Cys Ala Ala Leu Asn Ala Gly Asn Met Leu Thr Phe
1               5                   10
```

<210> SEQ ID NO 17
<211> LENGTH: 14
<212> TYPE: PRT
<213> ORGANISM: artificial sequence
<220> FEATURE:
<223> OTHER INFORMATION: amino acid sequence of CDR3 alpha of clone 2

<400> SEQUENCE: 17

```
Cys Val Val Asn Lys Gly Ser Ser Ala Ser Lys Ile Ile Phe
1               5                   10
```

<210> SEQ ID NO 18
<211> LENGTH: 14
<212> TYPE: PRT
<213> ORGANISM: artificial sequence
<220> FEATURE:
<223> OTHER INFORMATION: amino acid sequence of CDR3 beta of clone 2

<400> SEQUENCE: 18

```
Cys Ala Ser Ser Glu Gly Ala Ser Asn Gln Pro Gln His Phe
1               5                   10
```

<210> SEQ ID NO 19
<211> LENGTH: 14
<212> TYPE: PRT
<213> ORGANISM: artificial sequence
<220> FEATURE:
<223> OTHER INFORMATION: amino acid sequence of CDR3 alpha of clone 3-1

<400> SEQUENCE: 19

```
Cys Ala Met Thr Tyr Ser Gly Gly Tyr Gln Lys Val Thr Phe
1               5                   10
```

<210> SEQ ID NO 20
<211> LENGTH: 13
<212> TYPE: PRT
<213> ORGANISM: artificial sequence
<220> FEATURE:
<223> OTHER INFORMATION: amino acid sequence of CDR3 brta of clone 3-1

<400> SEQUENCE: 20

```
Cys Ser Ala Arg Ala Gly Val Gln Glu Thr Gln Tyr Phe
1               5                   10
```

```
<210> SEQ ID NO 21
<211> LENGTH: 14
<212> TYPE: PRT
<213> ORGANISM: artificial sequence
<220> FEATURE:
<223> OTHER INFORMATION: amino acid sequence of CDR3 alpha of clone 3-2

<400> SEQUENCE: 21

Cys Ala Met Thr Pro Ser Gly Gly Tyr Gln Lys Val Thr Phe
1               5                   10


<210> SEQ ID NO 22
<211> LENGTH: 14
<212> TYPE: PRT
<213> ORGANISM: artificial sequence
<220> FEATURE:
<223> OTHER INFORMATION: amino acid sequence of CDR3 alpha of clone 4

<400> SEQUENCE: 22

Cys Ala Val Ser Asp Gln Gly Arg Asp Asp Lys Ile Ile Phe
1               5                   10


<210> SEQ ID NO 23
<211> LENGTH: 13
<212> TYPE: PRT
<213> ORGANISM: artificial sequence
<220> FEATURE:
<223> OTHER INFORMATION: amino acid sequence of CDR3 beta of clone 4

<400> SEQUENCE: 23

Cys Ser Ala Arg Asp Trp Arg Glu Glu Thr Gln Tyr Phe
1               5                   10


<210> SEQ ID NO 24
<211> LENGTH: 11
<212> TYPE: PRT
<213> ORGANISM: artificial sequence
<220> FEATURE:
<223> OTHER INFORMATION: amino acid sequence of CDR3 beta of clone 5-2

<400> SEQUENCE: 24

Cys Ala Ser Ser Pro Thr Tyr Glu Gln Tyr Phe
1               5                   10


<210> SEQ ID NO 25
<211> LENGTH: 14
<212> TYPE: PRT
<213> ORGANISM: artificial sequence
<220> FEATURE:
<223> OTHER INFORMATION: amino acid sequence of CDR3 alpha of clone 6

<400> SEQUENCE: 25

Cys Ala Glu Asn Ser Gly Gly Ser Asn Tyr Lys Leu Thr Phe
1               5                   10


<210> SEQ ID NO 26
<211> LENGTH: 14
<212> TYPE: PRT
<213> ORGANISM: artificial sequence
<220> FEATURE:
<223> OTHER INFORMATION: amino acid sequence of CDR3 beta of clone 6

<400> SEQUENCE: 26

Cys Ser Ala Lys Thr Ser Gly Arg Gly Glu Thr Gln Tyr Phe
1               5                   10


<210> SEQ ID NO 27
```

-continued

<211> LENGTH: 16
<212> TYPE: PRT
<213> ORGANISM: artificial sequence
<220> FEATURE:
<223> OTHER INFORMATION: amino acid sequence of CDR3 alpha of clone 7-1

<400> SEQUENCE: 27

Cys Ala Ala Thr Leu Tyr Ser Gly Ala Gly Ser Tyr Gln Leu Thr Phe
1 5 10 15

<210> SEQ ID NO 28
<211> LENGTH: 12
<212> TYPE: PRT
<213> ORGANISM: artificial sequence
<220> FEATURE:
<223> OTHER INFORMATION: amino acid sequence of CDR3 beta of clone 7-1

<400> SEQUENCE: 28

Cys Ala Ser Ser Ser Arg Glu Asp Thr Gln Tyr Phe
1 5 10

<210> SEQ ID NO 29
<211> LENGTH: 16
<212> TYPE: PRT
<213> ORGANISM: artificial sequence
<220> FEATURE:
<223> OTHER INFORMATION: amino acid sequence of CDR3 alpha of clone 7-2

<400> SEQUENCE: 29

Cys Ala Ala Thr Ser Tyr Ser Gly Ala Gly Ser Tyr Gln Leu Thr Phe
1 5 10 15

<210> SEQ ID NO 30
<211> LENGTH: 17
<212> TYPE: PRT
<213> ORGANISM: artificial sequence
<220> FEATURE:
<223> OTHER INFORMATION: amino acid sequence of CDR3 alpha of clone 8

<400> SEQUENCE: 30

Cys Ala Ala Ser Pro Pro Ser Tyr Gly Gly Ser Gln Gly Asn Leu Ile
1 5 10 15

Phe

<210> SEQ ID NO 31
<211> LENGTH: 13
<212> TYPE: PRT
<213> ORGANISM: artificial sequence
<220> FEATURE:
<223> OTHER INFORMATION: amino acid sequence of CDR3 beta of clone 8

<400> SEQUENCE: 31

Cys Ser Val Tyr Arg Gly Leu Asp Glu Lys Leu Phe Phe
1 5 10

<210> SEQ ID NO 32
<211> LENGTH: 14
<212> TYPE: PRT
<213> ORGANISM: artificial sequence
<220> FEATURE:
<223> OTHER INFORMATION: amino acid sequence of CDR3 alpha of clone 9

<400> SEQUENCE: 32

Cys Ala Leu Ser Gly Gly Asn Arg Asp Asp Lys Ile Ile Phe
1 5 10

```
<210> SEQ ID NO 33
<211> LENGTH: 13
<212> TYPE: PRT
<213> ORGANISM: artificial sequence
<220> FEATURE:
<223> OTHER INFORMATION: amino acid sequence of CDR3 beta of clone 9

<400> SEQUENCE: 33

Cys Ser Ala Arg Asp Trp Arg Gly Glu Thr Gln Tyr Phe
1               5                   10


<210> SEQ ID NO 34
<211> LENGTH: 9
<212> TYPE: PRT
<213> ORGANISM: artificial sequence
<220> FEATURE:
<223> OTHER INFORMATION: amino acid sequence of CDR3 alpha of clone 10-1

<400> SEQUENCE: 34

Cys Ala Ala Gln Tyr Ala Leu Asn Phe
1               5


<210> SEQ ID NO 35
<211> LENGTH: 15
<212> TYPE: PRT
<213> ORGANISM: artificial sequence
<220> FEATURE:
<223> OTHER INFORMATION: amino acid sequence of CDR3 beta of clone 10-2

<400> SEQUENCE: 35

Cys Ala Ser Ser His Gly Thr Gly Gly Arg Tyr Glu Gln Tyr Phe
1               5                   10                  15


<210> SEQ ID NO 36
<211> LENGTH: 9
<212> TYPE: PRT
<213> ORGANISM: artificial sequence
<220> FEATURE:
<223> OTHER INFORMATION: amino acid sequence of CDR3 alpha of clone 10-2

<400> SEQUENCE: 36

Cys Ala Ala Gly Tyr Ala Leu Asn Phe
1               5


<210> SEQ ID NO 37
<211> LENGTH: 15
<212> TYPE: PRT
<213> ORGANISM: artificial sequence
<220> FEATURE:
<223> OTHER INFORMATION: amino acid sequence of CDR3 beta of clone 10-2

<400> SEQUENCE: 37

Cys Ala Ser Ser Leu Gly Thr Ser Gly Arg Tyr Glu Gln Tyr Phe
1               5                   10                  15


<210> SEQ ID NO 38
<211> LENGTH: 7
<212> TYPE: PRT
<213> ORGANISM: artificial sequence
<220> FEATURE:
<223> OTHER INFORMATION: amino acid sequence of epitope of SARS-CoV-2
      for focillar helper T cell

<400> SEQUENCE: 38

Leu Leu Gln Tyr Gly Ser Phe
1               5
```

```
<210> SEQ ID NO 39
<211> LENGTH: 15
<212> TYPE: PRT
<213> ORGANISM: artificial sequence
<220> FEATURE:
<223> OTHER INFORMATION: amino acid sequence of epitope of SARS-CoV-2
      for focillar helper T cell

<400> SEQUENCE: 39

Trp Asn Arg Lys Arg Ile Ser Asn Cys Val Ala Asp Tyr Ser Val
1               5                   10                  15


<210> SEQ ID NO 40
<211> LENGTH: 11
<212> TYPE: PRT
<213> ORGANISM: artificial sequence
<220> FEATURE:
<223> OTHER INFORMATION: amino acid sequence of epitope of SARS-CoV-2
      for focillar helper T cell

<400> SEQUENCE: 40

Phe Ile Lys Gln Tyr Gly Asp Cys Leu Gly Asp
1               5                   10


<210> SEQ ID NO 41
<211> LENGTH: 11
<212> TYPE: PRT
<213> ORGANISM: artificial sequence
<220> FEATURE:
<223> OTHER INFORMATION: amino acid sequence of epitope of SARS-CoV-2
      for focillar helper T cell

<400> SEQUENCE: 41

Met Ile Ala Gln Tyr Thr Ser Ala Leu Leu Ala
1               5                   10


<210> SEQ ID NO 42
<211> LENGTH: 11
<212> TYPE: PRT
<213> ORGANISM: artificial sequence
<220> FEATURE:
<223> OTHER INFORMATION: amino acid sequence of epitope of SARS-CoV-2
      for focillar helper T cell

<400> SEQUENCE: 42

Lys Lys Phe Leu Pro Phe Gln Gln Phe Gly Arg
1               5                   10


<210> SEQ ID NO 43
<211> LENGTH: 11
<212> TYPE: PRT
<213> ORGANISM: artificial sequence
<220> FEATURE:
<223> OTHER INFORMATION: amino acid sequence of epitope of SARS-CoV-2
      for focillar helper T cell

<400> SEQUENCE: 43

Gln Ala Leu Asn Thr Leu Val Lys Gln Leu Ser
1               5                   10


<210> SEQ ID NO 44
<211> LENGTH: 15
<212> TYPE: PRT
<213> ORGANISM: artificial sequence
<220> FEATURE:
<223> OTHER INFORMATION: amino acid sequence of a part of SARS-CoV-2
      protein

<400> SEQUENCE: 44
```

```
Leu Pro Pro Leu Leu Thr Asp Glu Met Ile Ala Gln Tyr Thr Ser
1               5                   10                  15


<210> SEQ ID NO 45
<211> LENGTH: 15
<212> TYPE: PRT
<213> ORGANISM: artificial sequence
<220> FEATURE:
<223> OTHER INFORMATION: amino acid sequence of a part of SARS-CoV-2
      protein

<400> SEQUENCE: 45

Pro Pro Leu Leu Thr Asp Glu Met Ile Ala Gln Tyr Thr Ser Ala
1               5                   10                  15


<210> SEQ ID NO 46
<211> LENGTH: 15
<212> TYPE: PRT
<213> ORGANISM: artificial sequence
<220> FEATURE:
<223> OTHER INFORMATION: amino acid sequence of a part of SARS-CoV-2
      protein

<400> SEQUENCE: 46

Pro Leu Leu Thr Asp Glu Met Ile Ala Gln Tyr Thr Ser Ala Leu
1               5                   10                  15


<210> SEQ ID NO 47
<211> LENGTH: 15
<212> TYPE: PRT
<213> ORGANISM: artificial sequence
<220> FEATURE:
<223> OTHER INFORMATION: amino acid sequence of a part of SARS-CoV-2
      protein

<400> SEQUENCE: 47

Leu Leu Thr Asp Glu Met Ile Ala Gln Tyr Thr Ser Ala Leu Leu
1               5                   10                  15


<210> SEQ ID NO 48
<211> LENGTH: 15
<212> TYPE: PRT
<213> ORGANISM: artificial sequence
<220> FEATURE:
<223> OTHER INFORMATION: amino acid sequence of a part of SARS-CoV-2
      protein

<400> SEQUENCE: 48

Leu Thr Asp Glu Met Ile Ala Gln Tyr Thr Ser Ala Leu Leu Ala
1               5                   10                  15


<210> SEQ ID NO 49
<211> LENGTH: 15
<212> TYPE: PRT
<213> ORGANISM: artificial sequence
<220> FEATURE:
<223> OTHER INFORMATION: amino acid sequence of a part of SARS-CoV-2
      protein

<400> SEQUENCE: 49

Thr Asp Glu Met Ile Ala Gln Tyr Thr Ser Ala Leu Leu Ala Gly
1               5                   10                  15


<210> SEQ ID NO 50
<211> LENGTH: 15
<212> TYPE: PRT
<213> ORGANISM: artificial sequence
```

<220> FEATURE:
<223> OTHER INFORMATION: amino acid sequence of a part of SARS-CoV-2 protein

<400> SEQUENCE: 50

Asp Glu Met Ile Ala Gln Tyr Thr Ser Ala Leu Leu Ala Gly Thr
1 5 10 15

<210> SEQ ID NO 51
<211> LENGTH: 15
<212> TYPE: PRT
<213> ORGANISM: artificial sequence
<220> FEATURE:
<223> OTHER INFORMATION: amino acid sequence of a part of SARS-CoV-2 protein

<400> SEQUENCE: 51

Glu Met Ile Ala Gln Tyr Thr Ser Ala Leu Leu Ala Gly Thr Ile
1 5 10 15

<210> SEQ ID NO 52
<211> LENGTH: 15
<212> TYPE: PRT
<213> ORGANISM: artificial sequence
<220> FEATURE:
<223> OTHER INFORMATION: amino acid sequence of a part of SARS-CoV-2 protein

<400> SEQUENCE: 52

Met Ile Ala Gln Tyr Thr Ser Ala Leu Leu Ala Gly Thr Ile Thr
1 5 10 15

<210> SEQ ID NO 53
<211> LENGTH: 15
<212> TYPE: PRT
<213> ORGANISM: artificial sequence
<220> FEATURE:
<223> OTHER INFORMATION: amino acid sequence of a part of SARS-CoV-2 protein

<400> SEQUENCE: 53

Ile Ala Gln Tyr Thr Ser Ala Leu Leu Ala Gly Thr Ile Thr Ser
1 5 10 15

<210> SEQ ID NO 54
<211> LENGTH: 15
<212> TYPE: PRT
<213> ORGANISM: artificial sequence
<220> FEATURE:
<223> OTHER INFORMATION: amino acid sequence of a part of SARS-CoV-2 protein

<400> SEQUENCE: 54

Ala Gln Tyr Thr Ser Ala Leu Leu Ala Gly Thr Ile Thr Ser Gly
1 5 10 15

<210> SEQ ID NO 55
<211> LENGTH: 15
<212> TYPE: PRT
<213> ORGANISM: artificial sequence
<220> FEATURE:
<223> OTHER INFORMATION: amino acid sequence of a part of SARS-CoV-2 protein

<400> SEQUENCE: 55

Gln Tyr Thr Ser Ala Leu Leu Ala Gly Thr Ile Thr Ser Gly Trp
1 5 10 15

-continued

```
<210> SEQ ID NO 56
<211> LENGTH: 15
<212> TYPE: PRT
<213> ORGANISM: artificial sequence
<220> FEATURE:
<223> OTHER INFORMATION: amino acid sequence of a part of SARS-CoV-2
      protein

<400> SEQUENCE: 56

Tyr Thr Ser Ala Leu Leu Ala Gly Thr Ile Thr Ser Gly Trp Thr
1               5                   10                  15
```